US010450611B2

(12) United States Patent
West et al.

(10) Patent No.: US 10,450,611 B2
(45) Date of Patent: Oct. 22, 2019

(54) PERSONALIZED GENETIC TESTING

(71) Applicant: Personalis, Inc., Menlo Park, CA (US)

(72) Inventors: John West, Menlo Park, CA (US);
Christian Haudenschild, Menlo Park,
CA (US); Richard Chen, Menlo Park,
CA (US)

(73) Assignee: Personalis, Inc., Menlo Park, CA (US)

( * ) Notice: Subject to any disclaimer, the term of this patent is extended or adjusted under 35 U.S.C. 154(b) by 0 days.

(21) Appl. No.: 15/793,845

(22) Filed: Oct. 25, 2017

(65) Prior Publication Data

US 2018/0051338 A1 Feb. 22, 2018

Related U.S. Application Data

(63) Continuation of application No. PCT/US2017/034823, filed on May 26, 2017.

(60) Provisional application No. 62/342,674, filed on May 27, 2016.

(51) Int. Cl.

| | | |
|---|---|---|
| C12Q 1/68 | (2018.01) | |
| C12Q 1/6883 | (2018.01) | |
| G16B 30/00 | (2019.01) | |
| G06N 3/12 | (2006.01) | |
| C12Q 1/6853 | (2018.01) | |
| C12Q 1/6869 | (2018.01) | |
| G16B 99/00 | (2019.01) | |
| G16B 20/00 | (2019.01) | |

(52) U.S. Cl.
CPC ............. *C12Q 1/6883* (2013.01); *C12Q 1/68* (2013.01); *C12Q 1/6853* (2013.01); *C12Q 1/6869* (2013.01); *G06N 3/12* (2013.01); *G16B 20/00* (2019.02); *G16B 30/00* (2019.02); *G16B 99/00* (2019.02)

(58) Field of Classification Search
None
See application file for complete search history.

(56) References Cited

U.S. PATENT DOCUMENTS

| | | |
|---|---|---|
| 4,458,066 A | 7/1984 | Caruthers et al. |
| 4,683,202 A | 7/1987 | Mullis |
| 5,143,854 A | 9/1992 | Pirrung et al. |
| 5,382,510 A | 1/1995 | Levine et al. |
| 5,412,087 A | 5/1995 | McGall et al. |
| 5,432,065 A | 7/1995 | Fuller |
| 5,472,672 A | 12/1995 | Brennan |
| 6,045,996 A | 4/2000 | Cronin et al. |
| 7,211,654 B2 | 5/2007 | Gao et al. |
| 7,534,561 B2 | 5/2009 | Sana et al. |
| 8,026,094 B2 | 9/2011 | Green et al. |
| 8,415,101 B2 | 4/2013 | Garner |
| 8,862,410 B2 | 10/2014 | Hatchwell et al. |
| 9,128,861 B2 | 9/2015 | Bartha et al. |
| 9,183,496 B2 | 11/2015 | Harris et al. |
| 2007/0184436 A1 | 8/2007 | Myerson et al. |
| 2010/0029498 A1 | 2/2010 | Gnirke et al. |
| 2016/0122831 A1 | 5/2016 | West |
| 2016/0283484 A1 | 9/2016 | Chandratillake et al. |

FOREIGN PATENT DOCUMENTS

| | | |
|---|---|---|
| WO | WO-2007055244 A1 | 5/2007 |
| WO | WO-2014207245 A1 | 12/2014 |
| WO | WO-2015051275 A1 | 4/2015 |
| WO | WO-2017205823 A1 | 11/2017 |

OTHER PUBLICATIONS

Albert, et al. Direct selection of human genomic loci by microarray hybridization. Nat Methods. Nov. 2007;4(11):903-5. Epub Oct. 14, 2007.
Esplin et al., Personalized sequencing and the future of medicine: discovery, diagnosis and defeat of disease. Pharmacogenomics. Nov. 2014. vol. 15, Nov. 14. pp. 1771-1790.
Gnirke et al. Solution hybrid selection with ultra-long oligonucleotides for massively parallel targeted sequencing. Nat Biotechnol 27(2):182-189 (2009).
Kosuri and Church, "Large-scale de novo DNA synthesis: technologies and applications," Nature Methods, 11:499-507, 2014. Available at: http://www.nature.com/nmeth/journal/v11/n5/full/nmeth.2918.html .
Levin, et al., Targeted next-generation sequencing of a cancer transcriptome enhances detection of sequence variants and novel fusion transcripts. Genome Biology, 2009. 10:R115.
Marguiles, et al. Genome sequencing in microfabricated high-density picolitre reactors. Nature. Sep. 15, 2005;437(7057):376-80. Epub Jul. 31, 2005.
Mercer, et al., Targeted sequencing for gene discovery and quantification using RNA captureSeq. Nat Protoc May 2014. vol. 9, No. 5, pp. 989-1009.
Miller, et al., Basic concepts of microarrays and potential applications in clinical microbiology. Clinical Microbiology Reviews, Oct. 2009, p. 611-633.
Murray, et al., Improved double-stranded DNA sequencing using the linear polymerase chain reaction. Nucleic Acids Research, vol. 17, No. 21. p. 8889. Nov. 11, 1989.
Lathe, R., Synthetic oligonucleotide probes deduced from amino acid sequence data: Theoretical and practical considerations. Journal of Molecular Biology, May 5, 1985; 183(1): 1-12.

(Continued)

*Primary Examiner* — James Martinell
(74) *Attorney, Agent, or Firm* — Wilson Sonsini Goodrich & Rosati

(57) ABSTRACT

The present disclosure provides methods and systems for personalized genetic testing of a subject. In some embodiments, a sequencing assay is performed on a biological sample from the subject, which then leads to genetic information related to the subject. Next, nucleic acid molecules are array-synthesized or selected based on the genetic information derived from data of the sequencing assay. At least some of the nucleic acid molecules may then be used in an assay which may provide additional information on one or more biological samples from the subject or a biological relative of the subject.

31 Claims, 8 Drawing Sheets

(56) References Cited

OTHER PUBLICATIONS

PCT/US2017/034823 International Search Report and Written Opinion dated Oct. 23, 2017.
Bamshad., "Exome sequencing as a tool for Mendelian disease gene discovery", Nature Reviews Genetics, Nov. 2011, 12, 745-755.
Goris; et al., "The Immunogenetic Architecture of Autoimmune Disease", Cold Spring Harbor Perspectives in Biology, 2012, 4:a007260, 1-15.
Ito; et al., "Cancer Neoantigens: A Promising Source of Immunogens for Cancer Immunotherapy", Journal of Clinical & Cellular Immunology, Apr. 28, 2015, vol. 6, No. 2, 2155-9899.
Lu; et al., "Cancer immunotherapy targeting neoantigens", Seminars in Immunology, Elsevier, 2016, 28, 22-27.
Robinson; et al., "The Human Phenotype Ontology: A Tool for Annotating and Analyzing Human Hereditary Disease", The American Journal of Human Genetics, Nov. 7, 2008, 83, 610-615.
Vinay; et al., "Immune evasion in cancer: Mechanistic basis and therapeutic strategies", Seminars in Cancer Biology, Elsevier, 2015, 35, S185-S198.

PERSONALIZED GENETIC TESTING

CROSS-REFERENCE

This application is a continuation application of International Application Patent No. PCT/US2017/034823, filed May 26, 2017, which application claims priority to U.S. Provisional Patent Application No. 62/342,674, filed May 27, 2016, each of which is entirely incorporated herein by reference.

BACKGROUND

The history of deoxynucleic acid (DNA) sequencing and DNA synthesis has been intertwined, with advances in one often leading to advances in or applications of the other.

The double helix structure of DNA was discovered by Watson and Crick in 1953.

In the decades following that, chemists worked to develop methods to synthesize DNA strands (oligonucleotides) of predefined sequence. Caruthers, et al (U.S. Pat. No. 4,458,066 "Process for preparing oligonucleotides", filed Mar. 24, 1981) introduced the phosphoramidite chemistry now widely used. It was implemented on substrates similar to chromatography columns, yielding one oligonucleotide per synthesis. At the end of this process, the synthesized molecules are cleaved from the substrates on which they have been synthesized, so they can be used in further reactions in solution.

Instrument manufacturers subsequently introduced equipment implementing this process on multiple columns in parallel. On Apr. 24, 2000 for example, PE Applied Biosystems issued a press release introducing its "ABI 3900 High Throughput DNA Synthesizer" with 48 columns operating concurrently. In a system of this type, each oligo was synthesized on a separate substrate and delivered in a separate tube (or other container). Relatively large amounts of each DNA sequence can be synthesized on these machines (the ABI 3900 specification was 40 nanomoles up to 1 micro-mole per sequence).

Methods for the synthesis of DNA sequences led to Polymerase Chain Reaction (PCR), which uses synthesized DNA priming sequences. Kary Mullis, who invented PCR and was later awarded the Nobel Prize for it, was working in a DNA synthesis lab at Cetus at the time. It was originally devised as a method to enable sequencing of the sickle cell anemia locus via Sanger sequencing. U.S. Pat. No. 4,683,202 "Process for amplifying nucleic acid sequences", the original PCR patent, was filed in 1985.

This was further refined in methods which integrated DNA amplification and the Sanger chain terminating reaction, e.g., Murray, V., "Improved double-stranded DNA sequencing using the linear polymerase chain reaction" Nucleic Acids Research, Vol 17, No 21 Pg 8889, Nov. 11, 1989. Still further refinement along these lines was termed "Cycle Sequencing" (e.g., U.S. Pat. No. 5,432,065 filed Mar. 30, 1993). All of these combined the use of individually synthesized DNA sequences, as primers for further DNA synthesis with polymerase enzymes.

During this time, other groups developed methods for synthesis of DNA on a highly parallel microscopic scale, on a single substrate. This increased the parallelism of DNA synthesis by over a thousand-fold. Compared to the ABI 3900 instrument mentioned above for example, which can synthesize up to 48 sequences in parallel, some array-based methods can synthesize over 50,000 sequences in parallel without large manufacturing set-up costs.

One method of array-based synthesis was described in Pirrung, et al (U.S. Pat. No. 5,143,854 "Large scale photolithographic solid phase synthesis of polypeptides and receptor binding screening thereof", priority date Jun. 7, 1989). It was developed by scientists at Affymax Corporation, later spun out as Affymetrix, Inc. This early work used fixed photolithographic masks, similar to those of the semiconductor industry. This enabled production of many "DNA arrays" with the same set of DNA sequences on them.

A group at the University of Wisconsin at Madison later devised a more flexible version of this using micro-mirror arrays (rather the fixed photolithographic masks) to dynamically define the spatial pattern of light in the system. This was spun out into the company Nimblegen in 1999, which was acquired by Roche in 2007.

Another method for synthesis of DNA on a highly parallel microscopic scale, on a single substrate, was developed using technology from ink-jet printing. Brennan (U.S. Pat. No. 5,472,672 "Apparatus and method for polymer synthesis using arrays" filed Oct. 22, 1993) described such a system including the dispensing of microscopic droplets of synthesis reagents through an array of nozzles on a moveable print head. This technology was commercialized by Agilent, Inc.

Early applications of these DNA arrays involved use of the oligonucleotides on the array substrates where they were synthesized. This typically involved hybridization of DNA (or complementary deoxyribonucleic acid (cDNA)) from a test sample to the oligonucleotides on the array. If the DNA (or cDNA) of the test sample was fluorescently labeled in advance, then imaging the array after hybridization and washing can quantify the amount of each sequence in the test sample. This was initially used to measure mRNA expression of genes and it was later used for genotyping.

Application of DNA array technology to DNA sequencing largely waited until DNA sequencing itself advanced. The original methods of DNA sequencing (Sanger, Maxim & Gilbert shared a 1975 Nobel prize) used electrophoresis for separation and subsequent readout. Each such electrophoretic separation and detection was spatially separate, though companies developed instruments with several in parallel (e.g., Applied Biosystems Model 370, introduced about 1987, supported up to 24 in parallel; Applied Biosystems Model 3700, introduced in 1999 supported up to 96 in parallel, and Amersham's Molecular Dynamics unit introduced a version of its MegaBace system about 2002 with 384 in parallel.)

Several groups did attempt to leverage DNA arrays for DNA sequencing (e.g., Lysov, et al, 1996, "Efficiency of sequencing by hybridization on oligonucleotide matrix supplemented by measurement of the distance between DNA segments."). Affymetrix commercialized this approach for small applications (variants in CYP drug metabolizing genes, genotyping of HIV). These methods conduct the DNA sequencing reactions and fluorescent readout on the array and thus have been limited to one base per array spot and fairly small non-repetitive portions of genomes. Heidi Rehm, et al at the Harvard Medical School published a set of protocols for this in April 2011 "Targeted Sequencing Using Affymetrix CustomSeq Arrays" in Current Protocols in Human Genetics. In it the technology was described as suitable for re-sequencing portions of the human genome up to 300,000 bases in total length.

The field moved forward with the commercialization of "Next Generation DNA Sequencing" methods, which enabled measurement of hundreds of thousands of sequences at a time. One of the first such systems was commercialized by 454, Inc (previously a division of Curagen, Inc and later acquired by Roche) in 2005 (Margulies, M. et al. "Genome sequencing in microfabricated high-density picoliter reactors" Nature 437, 376-380 (2005). This initial system can measure up to 200,000 sequences in parallel, each on average 100 bases long.

Two years later, in 2007, a group at the Baylor College of Medicine used a 454 DNA sequencing instrument to sequence an exome (Albert, et al "Direct selection of human genomic loci by microarray hybridization" Nature Methods, November 2007, 4(11):903-5). The key to this work was that a DNA array was used not as a substrate for sequencing itself, but to enrich a genomic DNA sample for just the parts of the genome intended for sequencing. The original DNA sample, fragmented, was hybridized to the array. Portions of the genome which did not hybridize were washed off. Then the portions of the genome which did hybridize to the array were eluted off the array and sequenced separate from the array, using the 454 system. The DNA arrays used were from Nimblegen. Although that DNA synthesis technology had been available since 1999, it was its 2007 combination with huge parallelism of next generation DNA sequencing that made this application practical.

In the work described above, DNA sequences synthesized on an array were used in-place on the array substrate. During the early 2000's though, groups began to explore technologies by which DNA molecules can be synthesized on an array but attached to the substrate of the array by a cleavable linker. This meant that after array synthesis, the linkers can be cleaved (e.g., chemically) releasing the oligonucleotides into solution, where they can be used as a pool. One example of this work is U.S. Pat. No. 7,211,654 (Xiaolian, et al, "Linkers and co-coupling agents for optimization of oligonucleotide synthesis and purification on solid supports" May 1, 2007).

In 2007, a group at the Broad Institute, began to explore use of this approach to create pools of oligonucleotides in solution to capture select portions of the genome of a test sample. (See U.S. provisional application 61/063,489, Gnirke, et al, filed Feb. 4, 2008: "Selection of nucleic acids by solution hybridization to oligonucleotide baits".) Dr. Carsten Russ of the Broad Institute described this approach at the February 2008 AGBT conference (reported by GenomeWeb). During 2008, Agilent licensed this technology. It was published on line Feb. 1, 2009 "Solution hybrid selection with ultra-long oligonucleotides for massively parallel sequencing" Nature Biotechnology 27, 182-189 (2009). In February 2009 Agilent launched this as a product line (trade name "SureSelect") with its first human exome kit ("SureSelect All Exon").

Dr. Gnirke, et al at the Broad Institute continued to innovate and applied targeted capture, using array synthesis of DNA, to RNA transcriptomes: "Targeted next-generation sequencing of a cancer transcriptome enhances detection of sequence variants and novel fusion transcripts" Joshua Levin, et al (including Andreas Gnirke). Genome Biology 2009, 10:R115.

In parallel with this, Next Generation DNA Sequencing technologies continued to advance. In June 2006, Solexa, Inc first shipped its Genome Analyzer system. This system measured 40 million DNA sequences in parallel, each initially 25 bases long. In 2008 Illumina, Inc acquired Solexa. Subsequent versions of this technology have continued to advance. The most current instrument (Illumina HiSeq-4000) can produce about 6 billion sequences in parallel, each 2×125 bases, for a total of 1.5 trillion bases, in a single run.

Exome sequencing has been broadly adopted as a research tool. As an example, the Exome Aggregation Consortium based at the Broad Institute has released a dataset based on human exome sequences from over 60,000 individuals (release v0.3 Jan. 2015).

Exome sequencing has also been adopted clinically. The first commercial clinical exome tests were announced by GeneDx and Ambry Genetics at the ASHG conference in October 2011. Others including the Baylor College of Medicine have also offered commercial clinical human exome-based tests, and over 8,000 have been performed.

DNA synthesis technologies have continued to advance, particularly focused on gene synthesis applications requiring very long DNA sequences. Many of these advances involve the construction of long DNA molecules by strategies which combine shorter synthetic DNA molecules. This was reviewed in: "Large-scale de novo DNA synthesis: technologies and applications" Sriram Kosuri and George Church, Nature Methods, Volume 11, No 5, May 2014; 499.

SUMMARY

In spite of the advances described above, the clinical adoption of exome-scale sequencing has been limited by the costs involved. Health insurers, who are asked to pay for these tests, often refuse, given the scale of the expense. This problem is even worse in cancer, where the depth of deoxynucleic acid (DNA) sequencing required can be much higher (e.g., >500×) than that for inherited diseases (e.g., 30-100×).

While array-based DNA synthesis is now widely used to capture whole exomes, transcriptomes, or application-specific subsets of exomes (e.g., the genes involved with a specific Mendelian disease), a limitation of the field, as recognized herein, is the potential to leverage array synthesis of DNA in a personalized manner. The field has largely used array-based synthesis to develop standard products which are broadly applicable across a whole set of human patients and/or research subjects. Even where custom array synthesis is proposed, it is to sequence regions of the genome defined independent of a specific sample.

In one aspect, the disclosure provides a method for personalized genetic testing, comprising: (a) using a plurality of genetic characteristics to determine a nucleic acid configuration of an assay, which nucleic acid configuration includes nucleic acid sequences of a plurality of nucleic acid probe molecules, wherein the nucleic acid sequences are selective for genetic variants, wherein the plurality of genetic characteristics is determined by analyzing nucleic acid sequence data generated from at least one biological sample of a subject, and wherein the plurality of genetic characteristics include the genetic variants in the nucleic acid molecules from the at least one biological sample; (b) providing the plurality of nucleic acid probe molecules by (i) synthesizing the plurality of nucleic acid probe molecules using at least one array, or (ii) selecting the plurality of nucleic acid probe molecules from a collection of nucleic acid probe molecules; and (c) using the plurality of nucleic acid probe molecules provided in (b) to perform at least the assay on one or more biological samples from the subject or at least one biological relative of the subject, to generate data indicative of a presence or absence of at least a subset of the genetic variants in the subject or the at least one biological relative.

Some embodiments may further comprise generating the nucleic acid sequence data using a sequencing assay to sequence or quantify nucleic acid molecules from the at least one biological sample. In some embodiments providing the plurality of nucleic acid probe molecules comprises synthesizing the plurality of nucleic acid probe molecules using at least one array.

In some embodiments, in the sequencing assay, at least one biological sample is obtained from the subject at a first time point, and wherein in (c), the one or more biological samples are obtained from the subject or the at least one biological relative of the subject at a second time point subsequent to the first time point. In some embodiments, providing the plurality of nucleic acid probe molecules comprises selecting the plurality of nucleic acid probe molecules from a collection of nucleic acid probe molecules.

Some embodiments comprise outputting a report that is indicative of a presence or absence of the at least the subset of the genetic variants in the subject or the at least one biological relative. In some embodiments, the nucleic acid probe molecules comprise primers for amplifying the nucleic acid sequences.

Some embodiments further comprise outputting a report that is generated at least based on comparison of results from the sequencing assay with results from the second assay of (c).

In some embodiments, the one or more biological samples in (c) comprise a plurality of biological samples, and wherein (c) further comprises outputting a report that is generated at least based on comparison of results from the at least the assay from the plurality of biological samples assayed in (c) with each other.

In some embodiments, at least the assay comprises a plurality of the assay. In some embodiments, the plurality of the assay is performed on (i) a plurality of biological samples of the subject or (ii) a plurality of biological samples of the at least one biological relative of the subject.

Some embodiments further comprise providing a therapeutic intervention at least based on the presence or absence of the at least the subset of the genetic variants identified in (c).

In some embodiments, the sequencing assay comprises (i) exome sequencing, (ii) sequencing a panel of genes, (iii) whole genome sequencing, and/or (iv) sequencing a population of complementary deoxyribonucleic acid molecules derived from ribonucleic acid molecules. In some embodiments, the sequencing assay comprises sequencing the nucleic acid molecules generated in quantity or sequence by interaction with the at least one biological sample from the subject. In some embodiments, the sequencing assay comprises sequencing the nucleic acid molecules derived from antibody-oligonucleotide conjugates of the subject.

In some embodiments, the nucleic acid molecules from the at least one biological sample comprise nucleic acid molecules from cells of the subject and are representative of a germline genome of the subject. In some embodiments, the nucleic acid molecules from the at least one biological sample comprise nucleic acids from (i) white blood cells or (ii) non-cancerous cells adjacent to or embedded in a tumor or metastasis of the subject. In some embodiments, the nucleic acid molecules from the at least one biological sample are cell-free nucleic acid molecules. In some embodiments, at least one biological sample includes a blood sample and the nucleic acids molecules are from blood cells in the blood sample, and wherein the subject has been diagnosed with a blood-related cancer such that the nucleic acid molecules in (a) are representative of a cancer genome of the subject. In some embodiments, the nucleic acids molecules are derived from a buccal swab, and wherein the nucleic acid molecules are representative of an ectodermal genome of the subject. In some embodiments, at least one biological sample includes a tumor sample and the nucleic acids molecules are from cells in the tumor sample, and wherein the nucleic acid molecules are representative of a cancer genome of the subject. In some embodiments, the nucleic acid molecules are derived from T-cells and/or B-cells of an adaptive immune system of the subject, representing post-zygotic V(D)J recombination. In some embodiments, the nucleic acid molecules comprise non-human nucleic acid molecules derived from the at least one biological sample, representing a genome(s) of one or more microbial organisms.

In some embodiments, the sequencing assay comprises analysis of a single biological sample from the subject.

In some embodiments, at least one biological sample includes a plurality of biological samples, and wherein the first assay comprises analysis of the plurality of biological samples and at least one of the plurality of genetic characteristics determined in (b) is based on comparison of the analysis. In some embodiments, at least one biological sample includes a tumor of the subject, and wherein the first assay of (a) comprises analysis of the at least one biological sample and analysis of an additional biological sample which represents a germline genome of the subject. In some embodiments, at least one biological sample includes a tumor of the subject and the nucleic acid molecules include deoxyribonucleic acid (DNA) molecules and ribonucleic acid (RNA) molecules from the tumor, and wherein the first assay comprises analysis of the DNA and RNA.

In some embodiments, the plurality of genetic characteristics comprises one or more (i) single nucleotide polymorphisms, (ii) insertions and/or deletions, (iii) copy number variations, and (iv) structural variations. In some embodiments, the plurality of genetic characteristics include signatures combining multiple genetic variants. In some embodiments, the plurality of genetic characteristics comprise genetic variants in a germline sequence of the subject. In some embodiments, the plurality of genetic characteristics comprise post-zygotic variants from a germline sequence of the subject. In some embodiments, the plurality of genetic characteristics comprise post-zygotic recombination of elements from a germline sequence of the subject. In some embodiments, the plurality of genetic characteristics comprise levels of gene expression and/or sequencing read counts or read-depth in data derived from ribonucleic acid molecules or complementary deoxyribonucleic acid molecules derived from the at least one biological sample. In some embodiments, the plurality of genetic characteristics comprise levels of messenger ribonucleic acid expression of alleles from deoxyribonucleic acid molecules derived from the at least one biological sample. In some embodiments, the plurality of genetic characteristics comprise levels of methylation at specific locations or in specific regions of a genome.

In some embodiments, the plurality of genetic characteristics comprise locations in or regions of a genome, and wherein the plurality of nucleic acid probe molecules of the assay enrich or deplete a nucleic acid mixture of nucleic acid molecules which include the locations or regions of the genome or portions thereof.

In some embodiments, the plurality of genetic characteristics comprise numbers of sequences derived from oligo-antibody conjugates contacted with the at least one biological sample.

In some embodiments, the plurality of nucleic acid probe molecules of the assay enrich or deplete a nucleic acid mixture of nucleic acid molecules for target regions, by hybridization or amplification.

In some embodiments, each of the nucleic acid probe molecules of the assay includes a region targeted for a genomic locus or region. In some embodiments, each of the nucleic acid probe molecules of the second assay includes a barcode sequence. In some embodiments, each of the nucleic acid probe molecules of the assay includes a region for demultiplexing or selective amplification of at least a subset of nucleic acid molecules from the one or more biological samples, pooled across multiple genomic loci and/or across multiple subjects.

In some embodiments, the plurality of nucleic acid probe molecules includes sequences selected from a library of sequences. In some embodiments, the sequences capture coding exons of a genome of the subject or the at least one biological relative. In some embodiments, each of the plurality of nucleic acid probe molecules includes a variation from a reference sequence in the first assay of the subject.

Some embodiments further comprise synthesizing the plurality of nucleic acid probe molecules on a single solid substrate. Some embodiments further comprise synthesizing at least 100 nucleic acid sequences in parallel. Some embodiments further comprise synthesizing at least 1,000 nucleic acid sequences in parallel. Some embodiments further comprise synthesizing at least 10,000 nucleic acid sequences in parallel. Some embodiments further comprise synthesizing at least 50,000 nucleic acid sequences in parallel. Some embodiments further comprise synthesizing a plurality of nucleic acid sequences in spatially separate regions of the single solid substrate.

In some embodiments, the assay comprises generating nucleic acid sequence data from the one or more biological samples.

Some embodiments further comprise mapping the nucleic acid sequence data to a reference.

In some embodiments, each of the plurality of nucleic acid probe molecules is at least 50 bases in length.

In some embodiments, the assay comprises nucleic acid sequencing or gene expression analysis.

In some embodiment, each of the plurality of nucleic acid probe molecules of the assay includes oligonucleotide-directed genomic content comprising (i) at least one variable portion from a result of the sequencing assay and (ii) at least one fixed portion independent of the result of the sequencing assay. In some embodiments, the oligonucleotides of the at least one fixed portion are synthesized on the same array(s) as the at least one variable portion. The method of Claim 54, wherein oligonucleotides of the at least one fixed portion are synthesized on separate array(s) as the at least one variable portion. In some embodiments, at least one variable portion corresponds to genes which are more highly expressed than genes that correspond to the at least one fixed portion. In some embodiments, at least one variable portion corresponds to genes with a first expression profile and the at least one fixed portion corresponds to genes with a second expression profile, wherein the first expression profile has greater sample-to-sample variability than the second expression profile.

In some embodiments, the genomic content includes coding regions of genes. In some embodiments, the genomic content includes regions corresponding to non-coding ribonucleic acid (RNA), micro-RNA and/or intronic RNA.

In some embodiments, at least one variable portion corresponds to potential neoantigen causing genetic variants of the subject, and wherein the at least one fixed portion corresponds to one or more of (1) cancer driver genes, (2) genes involved in the pharmacogenomics of cancer drugs, (3) genes involved in Mendelian immunological diseases, (4) genes related to inherited forms of cancer, (5) genes associated with tumor escape from a targeted or immune cancer therapy, (6) HLA typing, and (7) genetic variants common in the population and used by B-allele methods to detect structural variation.

In some embodiments, at least one variable portion corresponds to genetic variants responsible for Mendelian phenotype of a proband, and wherein the at least one fixed portion corresponds to one or more of (1) additional genetic content not related to the Mendelian condition of the proband, (2) pharmacogenomics, (3) genetic sample ID by a fixed panel of genetic variants or a fixed panel of phenotype-related genetic variants, and (4) genetic variants common in the population and used by B-allele methods to detect structural variation.

In some embodiments, the (i) the subject is a member of a family pedigree and has or is suspected of having a medical condition that is Mendelian, (ii) the plurality of genetic characteristics in (a) are genetic variants of a nucleic sequence from a reference sequence(s) or alleles which match the reference sequence(s) and are associated with a medical condition, (iii) the nucleic acid sequences in (c) are configured to capture or amplify genomic regions comprising at least a subset of the genetic variants, (iv) the assay is nucleic acid sequencing, and (vi) the one or more biological samples in (c) is from the at least one biological relative that is a member of the family pedigree.

Some embodiments further comprise generating a report that identifies genetic variants shared by family members of the family pedigree, which genetic variants are responsible for the medical condition of the subject.

In some embodiments, the (i) the medical condition includes neurological clinical features, (ii) at least one of the biological samples assayed is from buccal swabs or other tissue of ectodermal lineage, (iii) the report is generated based at least in part on a possibility that one or more genetic variants of the subject are mosaic and included in the ectodermal lineage of the subject.

In some embodiments, at least one of the biological samples assayed includes deoxyribonucleic acid molecules from sperm of an individual in the family pedigree, and wherein the report is generated based at least in part on a possibility that one or more of the genetic variants are gonadal mosaic in a father of the subject.

Some embodiments further comprise combining genetic variants from probands in multiple Mendelian pedigrees into a single list of genetic loci and/or regions.

In some embodiments, the plurality of nucleic acid probe molecules are for in-solution capture of those genetic loci and/or regions, by hybridization.

In some embodiments, the plurality of nucleic acid probe molecules is synthesized by inkjet printing on an array with a capacity of at least about 50,000 nucleic acid sequences, and followed by cleavage from the array.

Some embodiments further comprise separating genetic variants for each Mendelian pedigree from nucleic acid data from the assay.

Some embodiments further comprise filtering genetic variants that are causal or suspected of being causal. In some embodiments, the plurality of genetic characteristics includes genes derived from a clinical phenotype of the subject. In some embodiments, the subject has cancer or is suspected of having cancer, and wherein the at least one biological sample includes a tissue sample or a blood sample from the subject.

In some embodiments, the nucleic acid molecules include deoxyribonucleic acid (DNA) molecules. In some embodiments, the DNA includes cell-free DNA. In some embodiments, the nucleic acid molecules include ribonucleic acid (RNA) molecules or complementary deoxyribonucleic acid (DNA) molecules derived from the RNA molecules. In some embodiments, the RNA includes cell-free RNA.

In some embodiments, the plurality of genetic characteristics in (a) includes one or more of (i) genetic variants of the nucleic acid sequence with respect to a reference sequence(s) or germline sequence(s), (ii) alleles which match the reference sequence(s) and are correlated with a type of cancer or other disease, (iii) alleles which determine a human leukocyte antigen (HLA) type, (iv) metrics of gene expression and/or allele-specific expression, and (v) quantification of non-coding ribonucleic acid (RNA molecules or micro-RNA molecules which are at least partially tissue-type specific or cancer-type specific.

Some embodiments further comprise filtering to select at least a subset of the genetic variants determined to be relevant for analysis of the tumor or a treatment of the subject.

In some embodiments, one or more biological samples are from the subject and include one or more of (i) germline deoxyribonucleic acid (DNA), (ii) tumor ribonucleic acid (RNA) or complementary DNA derived from the tumor RNA, (iii) cell-free DNA or RNA derived from blood plasma, (iv) DNA from the subject which contains or is suspected of containing mosaic variants, and (v) tumor and/or germline DNA.

Some embodiments further comprise generating a report that identifies genetic variants that are associated with a therapeutic intervention for the subject.

In some embodiments, the assay comprises sequencing nucleic acid molecules from the one or more biological samples of the subject.

In some embodiments, the assay comprises quantifying the nucleic acid molecules.

In some embodiments, the tissue sample is a tumor sample. In some embodiments, the plurality of genetic characteristics includes expressed genetic variants observed in a tumor sample of the subject but not observed in a germline of the subject, which have been assessed to be potential neoantigens for use in a personal cancer vaccine.

In some embodiments, the sequencing assay comprises sequencing the nucleic acid molecules. In some embodiments, the sequencing assay further comprises sequencing a germline nucleic acid molecule(s). In some embodiments, the sequencing assay comprises sequencing a plurality of V(D)J recombination segments, each of which specifying an antigen receptor of a T-cell and/or B-cell of the subject. In some embodiments, the plurality of genetic characteristics include identities and quantities of V(D)J sequences from the plurality of V(D)J recombination segments.

In some embodiments, the plurality of nucleic acid probe molecules capture or amplify nucleic acid sequences from the one or more biological samples that lead to neoantigens, which can be recognized by T-cell receptors or B-cell receptors corresponding to a V(D)J recombination segments. In some embodiments, the data confirms presence of genetic variants in a tumor of the subject, corresponding to the V(D)J recombination segments. In some embodiments, the data quantifies the genetic variants.

In some embodiments, at least one biological sample and the one or more biological samples include the same biological sample. In some embodiments, the nucleic acid sequence data has less than or equal to about five million sequence reads. In some embodiments, the nucleic acid sequence data has less than or equal to about one million sequence reads. In some embodiments, the plurality of nucleic acid probe molecules capture or amplify nucleic acid molecules in the one or more biological samples.

In some embodiments, the genetic variants are with respect to a reference genome. In some embodiments, the reference genome is from the subject.

In some embodiments, the at least one biological sample includes tumor tissue, and wherein the first assay comprises (i) exposing the tumor tissue to a mixture of oligonucleotide-antibody conjugates, wherein at least some of the oligonucleotide-antibody conjugates bind to proteins or peptides in the tumor tissue, and (ii) sequencing oligonucleotides released from the oligonucleotide-antibody conjugates upon binding to the proteins or peptides, which oligonucleotides correspond to the nucleic acid molecules, to yield the nucleic acid sequence data.

In some embodiments, the plurality of genetic characteristics includes identities and quantities of the oligonucleotide-antibody conjugates corresponding to the oligonucleotides released from the oligonucleotide-antibody conjugates. In some embodiments, the plurality of nucleic acid probe molecules are for capturing or amplifying one or more of (i) a plurality of oligonucleotide sequences of oligonucleotide-antibody conjugates, or (ii) deoxyribonucleic acid (DNA) or ribonucleic acid (RNA) sequences corresponding to the proteins or peptides bound to an antibody component of the oligonucleotide-antibody conjugates. In some embodiments, one or more biological samples include DNA molecules, RNA molecules, or complementary DNA molecules derived from the RNA molecules from the subject.

In some embodiments, the nucleic acid molecules from the at least one biological sample of the subject are obtained distal to their origin in a body of the subject, and the plurality of genetic characteristics include identified genomic locations of mosaic variants in the at least one biological sample. In some embodiments, the plurality of nucleic acid probe molecules amplify or enrich the mosaic variants. In some embodiments, the second assay is performed on the one or more biological samples from one or more other locations in the body of the subject, to determine an extent to which the mosaic variants are observed in the one or more biological samples. Some embodiments further comprise generating a report indicative of the origin in the body of the subject.

In some embodiments, the nucleic acid molecules include (i) cell-free deoxyribonucleic acid (DNA) or cell-free ribonucleic acid (RNA) from blood plasma, (ii) RNA from one or more exosomes derived from a blood sample of the subject, (iii) DNA or RNA from circulating tumor cells, or (iv) DNA or RNA from a tumor metastasis.

In another aspect, the present disclosure provides a method of personalized genetic testing, comprising: (a) deriving phenotypic information from a health or medical record of a subject, which health or medical record is in one or more databases; (b) determining a plurality of genetic characteristics of the subject from the phenotypic information derived in (a), wherein the plurality of genetic characteristics include genetic variants, and wherein the plurality of genetic characteristics facilitate diagnosis, prognosis or improved health or medical treatment of the subject; (c) using the plurality of genetic characteristics from (b) to determine a nucleic acid configuration of an assay, which nucleic acid configuration includes nucleic acid sequences of a plurality of nucleic acid probe molecules, wherein the nucleic acid sequences are selective for the genetic variants; (d) providing the plurality of nucleic acid probe molecules by (i) synthesizing the plurality of nucleic acid probe molecules using at least one array, or (ii) selecting the plurality of nucleic acid probe molecules from a collection of nucleic acid probe molecules; and (e) using the plurality of nucleic acid probe molecules provided in (d) to perform at least the assay on one or more biological samples from the subject or at least one biological relative of the subject, to generate data indicative of a presence or absence of at least a subset of the genetic variants in the subject or the at least one biological relative.

In some embodiments, providing the plurality of nucleic acid probe molecules comprises synthesizing the plurality of nucleic acid probe molecules using at least one array. In some embodiments, providing the plurality of nucleic acid probe molecules comprises selecting the plurality of nucleic acid probe molecules from a collection of nucleic acid molecules.

In some embodiments, the biological sample is obtained from the subject at a first time point, and wherein in (e), the one or more biological samples are obtained from the subject or the at least one biological relative of the subject at a second time point subsequent to the first time point. In some embodiments, the nucleic acid probe molecules comprise primers for amplifying the nucleic acid sequences.

Some embodiments further comprise outputting a report that is indicative of a presence or absence of the at least the subset of the genetic variants in the subject or the at least one biological relative. Some embodiments further comprise outputting a report that is generated at least based on comparison of results from the first assay of (a) with results from the second assay of (e).

In some embodiments, one or more biological samples in (e) comprise a plurality of biological samples, and wherein (e) further comprises outputting a report that is generated at least based on comparison of results from the at least the second assay from the plurality of biological samples assayed in (e) with each other. In some embodiments, at least the second assay comprises a plurality of the second assay. In some embodiments, the plurality of the second assay is performed on (i) a plurality of biological samples of the subject or (ii) a plurality of biological samples of the at least one biological relative of the subject.

Some embodiments further comprise providing a therapeutic intervention at least based on the presence or absence of the at least the subset of the genetic variants identified in (e).

In yet another aspect, the disclosure provides a non-transitory computer-readable medium comprising machine executable code that, upon execution by one or more computer processors, implements a method for personalized genetic testing, comprising: (a) using a plurality of genetic characteristics to determine a nucleic acid configuration of an assay, which nucleic acid configuration includes nucleic acid sequences of a plurality of nucleic acid probe molecules, wherein the nucleic acid sequences are selective for genetic variants, wherein the plurality of genetic characteristics is determined by analyzing nucleic acid sequence data generated from at least one biological sample of a subject, and wherein the plurality of genetic characteristics include the genetic variants in the nucleic acid molecules from the at least one biological sample; (b) providing the plurality of nucleic acid probe molecules by (i) synthesizing the plurality of nucleic acid probe molecules using at least one array, or (ii) selecting the plurality of nucleic acid probe molecules from a collection of nucleic acid probe molecules; and (c) using the plurality of nucleic acid probe molecules provided in (b) to perform at least the assay on one or more biological samples from the subject or at least one biological relative of the subject, to generate data indicative of a presence or absence of at least a subset of the genetic variants in the subject or the at least one biological relative.

In yet another aspect, the disclosure provides a non-transitory computer-readable medium comprising machine executable code that, upon execution by one or more computer processors, implements a method for personalized genetic testing, comprising: (a) deriving phenotypic information from a health or medical record of a subject, which health or medical record is in one or more databases; (b) determining a plurality of genetic characteristics of the subject from the phenotypic information derived in (a), wherein the plurality of genetic characteristics include genetic variants, and wherein the plurality of genetic characteristics facilitate diagnosis, prognosis or improved health or medical treatment of the subject; (c) using the plurality of genetic characteristics from (b) to determine a nucleic acid configuration of an assay, which nucleic acid configuration includes nucleic acid sequences of a plurality of nucleic acid probe molecules, wherein the nucleic acid sequences are selective for the genetic variants; (d) providing the plurality of nucleic acid probe molecules by (i) synthesizing the plurality of nucleic acid probe molecules using at least one array, or (ii) selecting the plurality of nucleic acid probe molecules from a collection of nucleic acid probe molecules; and (e) using the plurality of nucleic acid probe molecules provided in (d) to perform at least the assay on one or more biological samples from the subject or at least one biological relative of the subject, to generate data indicative of a presence or absence of at least a subset of the genetic variants in the subject or the at least one biological relative.

In an additional aspect, the disclosure provides a computer system for personalized genetic testing, comprising: one or more computer processors that are individually or collectively programmed to: (i) use a plurality of genetic characteristics to determine a nucleic acid configuration of an assay, which nucleic acid configuration includes nucleic acid sequences of a plurality of nucleic acid probe molecules, wherein the nucleic acid sequences are selective for the genetic variants, wherein the plurality of genetic characteristics is determined by analyzing nucleic acid sequence data generated from at least one biological sample of a subject, and wherein the plurality of genetic characteristics include the genetic variants in the nucleic acid molecules from the at least one biological sample; (ii) provide the plurality of nucleic acid probe molecules by (1) directing synthesis of the plurality of nucleic acid probe molecules using at least one array, or (2) selecting the plurality of nucleic acid probe molecules from a collection of nucleic acid probe molecules; and (iii) direct use of the plurality of nucleic acid probe molecules provided in (ii) to perform at least the assay on one or more biological samples from the subject or at least one biological relative of the subject, to generate data indicative of a presence or absence of at least a subset of the genetic variants in the subject or the at least one biological relative; and a computer display operative coupled to the one or more computer processors, wherein the computer display comprises a user interface that displays a report indicative of a presence or absence of the at least the subset of the genetic variants in the subject or the at least one biological relative.

In another aspect, the disclosure provides a computer system for personalized genetic testing, comprising: one or more computer processors that are individually or collectively programmed to: (i) derive phenotypic information from a health or medical record of a subject, which health or medical record is in one or more databases; (ii) determine a plurality of genetic characteristics of the subject from the phenotypic information derived in (i), wherein the plurality of genetic characteristics include genetic variants, and wherein the plurality of genetic characteristics facilitate diagnosis, prognosis or improved health or medical treatment of the subject; (iii) use the genetic characteristics from (ii) to determine a nucleic acid configuration of an assay, which nucleic acid configuration includes nucleic acid sequences of a plurality of nucleic acid probe molecules, wherein the nucleic acid sequences are selective for the genetic variants; (iv) provide the plurality of nucleic acid probe molecules by (1) directing synthesis of the plurality of nucleic acid probe molecules using at least one array, or (2) selecting the plurality of nucleic acid probe molecules from a collection of nucleic acid probe molecules; and (v) direct use of the plurality of nucleic acid probe molecules provided in (iv) to perform at least the assay on one or more biological samples from the subject or at least one biological relative of the subject, to generate data indicative of a presence or absence of at least a subset of the genetic variants in the subject or the at least one biological relative; and a computer display operative coupled to the one or more computer processors, wherein the computer display comprises a user interface that displays a report indicative of a presence or absence of the at least the subset of the genetic variants in the subject or the at least one biological relative.

In another aspect, the present disclosure provides a method of personalized genetic testing including: (a) using a first assay design to sequence nucleic acids derived from an individual person, (b) determining multiple genetic characteristics of that person or their sample from that data; (c) using the genetic characteristics from (b) to specify the design of a second assay, and in particular the sequences of multiple additional nucleic acid molecules to be used in that second assay; (d) synthesizing the additional nucleic acid molecules on at least one array; (e) using the synthesized nucleic acids to perform a second assay, on one or more samples from the same individual person, and/or from individuals in their family. Some embodiments comprise a further additional (f) a report is generated based on analysis comparing the results from the assay of (a) with results from the assay(s) of (e), or by comparison of results from assays from a plurality of samples assayed in (e) with each other.

In another aspect, the present disclosure provides a method of personalized genetic testing including: (a) deriving phenotypic information from the medical record of an individual person; (b) proposing multiple genetic characteristics which, if characterized, could lead to diagnosis, prognosis or improved medical treatment of the individual; (c) using the genetic characteristics from (b) to specify the design of an assay, and in particular the sequences of multiple nucleic acid molecules to be used in that assay; (d) synthesizing the nucleic acid molecules on at least one array; (e) using the synthesized nucleic acids to perform the assay, on one or more samples from the same individual person, and/or from individuals in their family. Some embodiments further comprise (f) generating a report based on analysis of the results from the assay(s) of (e), or by comparison of results from assays from a plurality of samples assayed in (e) with each other.

In some embodiments, the first assay comprises one of (i) exome sequencing, or (ii) sequencing a panel of genes, or (iii) whole genome sequencing, or (iv) sequencing a population of cDNA molecules derived from RNA. In some embodiments, the first assay comprises sequencing a population of nucleic acid molecules modified in quantity or sequence by interaction with a sample or samples derived from the individual person.

In some embodiments, the first assay comprises sequencing a population of nucleic acid molecules derived from antibody-oligonucleotide conjugates that bound to proteins of the individual person, including proteins of any tumor they may have. In some embodiments, the sequencing method of (a) comprises one of (i) sequencing by synthesis using a reversible terminator chemistry, or (ii) pyrosequencing, or (iii) nanopore sequencing, or (iv) real-time single molecule sequencing.

In some embodiments, the sample type which may be used in the assay of (a) comprises nucleic acids derived from cells of the individual person, representing their germline genome. In some embodiments, the sample type which may be used in the assay of (a) comprises nucleic acids derived from one of (i) white blood cells, or (ii) non-cancerous cells adjacent to or embedded in a tumor or metastasis of the individual person. In some embodiments, the sample type which may be used in the assay of (a) comprises cell-free nucleic acids derived from blood plasma of the individual person.

In some embodiments, the individual person has been diagnosed with a type of blood-related cancer such that the nucleic acids of their blood cells represent the cancer genome, not their germline genome, and wherein the nucleic acids of their blood cells are used in the assay of (a). In some embodiments, the sample type which may be used in the assay of (a) comprises nucleic acids derived from a buccal swab of the individual person, representing their ectodermal genome.

In some embodiments, the sample type which may be used in the assay of (a) comprises nucleic acids derived from cells of a tumor of the individual person, representing their cancer genome. In some embodiments, the sample type which may be used in the assay of (a) comprises nucleic acids derived from T-cells and/or B-cells of the adaptive immune system of the individual person, representing postzygotic V(D)J recombination. In some embodiments, the sample type which may be used in the assay of (a) comprises non-human nucleic acids derived from a sample of the individual person, representing the genome(s) of one or more other microbial species (bacteria or viruses).

In some embodiments, the first assay of (a) comprises analysis of a single sample from the individual. In some embodiments, the first assay of (a) comprises analysis of a plurality of samples from the individual and at least one of the genetic characteristics determined in (b) is based on comparison of those analyses. In some embodiments, the first assay of (a) comprises analysis of a sample from a tumor of the individual, and analysis of a second sample which represents the germline genome of the individual. In some embodiments, the first assay of (a) comprises analysis of DNA from a sample from a tumor of the individual, and analysis of RNA from a sample from a tumor of the individual.

In some embodiments, the genetic characteristics determined in (b) comprise or include one or more of (i) Single Nucleotide Polymorphisms (SNPs), or (ii) Insertions and/or Deletions (InDels), or Copy Number Variations or Structural Variations. In some embodiments, the genetic characteristics determined in (b) are or include signatures combining multiple genetic variants (e.g., the HLA type or the blood type of the individual) In some embodiments, the genetic characteristics determined in (b) comprise or include genetic variants in the germline sequence of the individual. In some embodiments, the genetic characteristics determined in (b) comprise or include post-zygotic (i.e., mosaic or somatic) variants from the germline sequence of the individual. In some embodiments, the genetic characteristics determined in (b) comprise or include post-zygotic recombination of elements from the germline sequence of the individual (e.g., V(D)J recombination). In some embodiments, the genetic characteristics determined in (b) comprise or include levels of gene expression (quantification of mRNA from individual genes and/or their splice variants) and/or sequencing read counts or read-depth in data derived from an RNA or cDNA sample. In some embodiments, the genetic characteristics determined in (b) comprise or include levels of mRNA expression (including presence/absence) of specific alleles derived from the DNA of the individual. In some embodiments, the genetic characteristics determined in (b) comprise or include levels of methylation at specific locations or in specific regions of the human genome. In some embodiments, the genetic characteristics determined in (b) comprise or include numbers of sequences derived from oligo-antibody conjugates contacted with the sample(s). In some embodiments, the genetic characteristics determined in (b) comprise or include specific locations in, or specific regions, of the human genome (e.g., the locations of SNP's); and further wherein the multiple additional nucleic acids to be used in the second assay are designed to enrich or deplete a nucleic acid mixture of those nucleic acid molecules which include those locations or regions of the human genome, or parts thereof.

In some embodiments, the additional nucleic acid molecules are designed to enrich or deplete a mixture, for the desired target regions, either by hybridization to the additional nucleic acid molecules or by amplification (e.g., by polymerase chain reaction) In some embodiments, the additional nucleic acid molecules are designed as primers for single-base extension, or multiple-base extension. In some embodiments, the sequences of the multiple additional nucleic acid molecules, to be used in the second assay, are composed of at least two parts: One part specific to the genomic locus or region targeted, and at least one other part for other applications in the second assay. This may be a barcode sequence or it may be a pair of amplification primer sequences.

In some embodiments, the "other applications in the second assay" include demultiplexing or selective amplification of a subset, downstream of array-based synthesis pooled across multiple genomic loci, or across multiple individuals, or both. In some embodiments, the sequences of the multiple additional nucleic acid molecules, to be used in the second assay, or portions of them, are selected from a library of sequences previously designed (e.g., to capture each of the coding exons of the human genome). In some embodiments, the library of previously designed sequences has previously itself been array synthesized and experimentally tested. In some embodiments, at least one of the sequences of the multiple additional nucleic acid molecules, to be used in the second assay, or portions of them, include a variation from the reference sequence seen in the first assay of the individual, not the reference sequence itself. In some embodiments, (d) comprises the synthesis of a plurality of nucleic acid sequences on a single solid substrate.

In some embodiments, the number of nucleic acid sequences synthesized in parallel on a single solid substrate is at least 100. In some embodiments, the number of nucleic acid sequences synthesized in parallel on a single solid substrate is at least 1,000. In some embodiments, the number of nucleic acid sequences synthesized in parallel on a single solid substrate is at least 10,000. In some embodiments, the number of nucleic acid sequences synthesized in parallel on a single solid substrate is at least 50,000. In some embodiments, each of the plurality of nucleic acid sequences synthesized on a single solid substrate is synthesized in a spatially separate region of the substrate.

In some embodiments, the sequence synthesized in each of the plurality of spatially separate regions of a single solid substrate is specified by light directed chemical reactions (e.g., photolithography) or by reagents dispensed in a jet from a moveable print head. In some embodiments, the common substrate can be mechanically partitioned without damaging the nucleic acids synthesized, after nucleic acid synthesis but before cleavage of the nucleic acid molecules from the substrate. In some embodiments, the nucleic acid molecules are at least 50 bases long. In some embodiments, the nucleic acid molecules are at least 130 bases long. In some embodiments, the nucleic acid molecules are at least 200 bases long. In some embodiments, the capacity of the array (i.e., the number of sequences which can be synthesized on a single solid substrate) is shared by synthesis of sequences for the testing of multiple otherwise unrelated testing cases.

In some embodiments, the sequences synthesized for unrelated testing cases are synthesized in spatially separated regions of a common substrate, followed by mechanical separation of the common substrate into separate pieces each containing one of those regions (e.g., wafer dicing). In some embodiments, the sequences synthesized for unrelated testing cases are synthesized on a common substrate, but contain subsequences (barcodes) which can later be used to segregate them for independent use (e.g., by hybridization). In some embodiments, the sequences synthesized for unrelated testing cases are synthesized on a common substrate, but their results are separated bioinformatically following the second assay ((e)).

In some embodiments, the second assay (e) determines nucleic acid sequences and maps them to a reference (e.g., a reference genome sequence or reference set of mRNA transcripts) such that the results needed for analysis of samples processed in (e) are positioned along the reference separate from (or partially separate from) those not needed (e.g., those captured in one sample by sequences synthesized for another sample).

In some embodiments, the second assay is one of (i) DNA sequencing, or (ii) genotyping, or (iii) gene expression analysis. In some embodiments, the sequencing method of (e) comprises one of (i) sequencing by synthesis using reversible terminator chemistry or (ii) pyrosequencing, or (iii) nanopore sequencing, or (iv) real-time single molecule sequencing. In some embodiments, the genotyping method of (e) comprises single-base extension, with readout of the single base by fluorescence or mass spectroscopy. In some embodiments, the genotyping of multiple loci are demultiplexed by one of (i) hybridization to an array, using nucleic acid barcodes incorporated into the sequences synthesized in (d), or (ii) using PCR primers incorporated into the sequences, or (iii) electrophoresis (e.g., SNaPshot or SNPlex), or (iv) mass spectroscopy.

In some embodiments, the oligo-directed genomic content of second assay comprises: (i) at least one variable portion, defined based on results of the first assay and (ii) at least one fixed portion, independent of the results of the first assay. In some embodiments, the oligos corresponding to the fixed portion of the genomic content are synthesized on the same array(s) as used to synthesize the variable portion of the genomic content. In some embodiments, the oligos corresponding to the fixed portion of the genomic content are synthesized on separate array(s) from those used to synthesize the variable portion of the genomic content. In some embodiments, (i) the variable content for a plurality of individuals is synthesized together on an array with the fixed content, and (ii) it is demultiplexed into oligo pools specific to each of those individuals post-synthesis, and (iii) the design of the nucleic acid sequences of the variable content contains at least two segments, one used for de-multiplexing post-synthesis, and (iv) the design of the nucleic acid sequences of the fixed content also contains at least two segments, one used for de-multiplexing post-synthesis, and (v) the de-multiplexing reaction post-synthesis uses methods which allow it to capture fixed content nucleic acid molecules along with each set of individual-specific variable content. In some embodiments, the variable portion of the oligo-directed genomic content corresponds to genes which are, or are expected to be, more highly expressed, and the fixed portion corresponds to genes with on average lower levels of gene expression. In some embodiments, the variable portion of the oligo-directed genomic content corresponds to genes whose expression is thought to vary more from sample to sample, and the fixed portion corresponds to genes with more consistent levels of gene expression from sample to sample. In some embodiments, the oligo-directed content, partitioned into fixed and variable portions as described, includes not only content from the coding regions of genes, but also other forms of transcribed RNA, including but not limited to long non-coding RNA, micro-RNA and Intronic RNA. In some embodiments, the variable portion of the oligo-directed genomic content corresponds to potential neoantigen causing variants of the individual, and the fixed portion corresponds to one or more of (a) cancer driver genes, (b) genes involved in the pharmacogenomics of cancer drugs, (c) genes involved in Mendelian immunological diseases, (d) genes related to inherited forms of cancer, (e) genes associated with tumor escape from a targeted or immune cancer therapy, (f) HLA typing, or (g) variants common in the population and used by B-allele methods to detect structural variation.

In some embodiments, the variable portion of the oligo-directed genomic content corresponds to variants which may be responsible for the Mendelian phenotype of a proband, and the fixed portion corresponds to one or more of (a) additional genetic content not related to the Mendelian condition of the proband (b) pharmacogenomics, or (c) genetic sample ID by a fixed panel of variants or a fixed panel of phenotype-related variants such as gender, blood type, or (d) variants common in the population and used by B-allele methods to detect structural variation.

In some embodiments, the individual of (a) is a member of a family pedigree, and is affected by a medical condition which may be Mendelian, the first assay is DNA sequencing, the genetic characteristics determined in (b) are variations of the DNA sequence so determined, from a human reference sequence, or alleles which match the human reference sequence but which are known to be correlated with a medical condition; optionally filtered to select those variants most likely to be causal, the DNA sequences designed in (c) are to capture or amplify the genomic regions of those variants, in subsequent samples, the assay of (e) is DNA sequencing, the samples sequenced in (e) are from other members of the same family pedigree, the report generated attempts to identify the genetic variants shared by the family members, which are responsible for the affliction of those pedigree members who are affected, by leveraging the rules of genetic inheritance, and data on multiple variant loci measured in multiple family members.

In some embodiments, the medical condition affecting the individual of (a) includes neurological clinical features, at least one of the samples assayed, in s (a) and/or (e) are from buccal swabs or other tissue of the ectodermal lineage, the report generated considers the possibility that one or more genetic variants of the afflicted individual are mosaic, and included in the ectodermal cell lineage of the individual.

In some embodiments, the at least one of the samples assayed, in s (a) and/or (e) are DNA from sperm of one of the individuals in a family pedigree, the report generated considers the possibility that one or more genetic variants of the afflicted individual are gonadal mosaic in the father of the afflicted individual. In some embodiments, the potentially causal genetic variants from probands in multiple Mendelian pedigrees are combined into a single list of genetic loci and/or regions. In some embodiments, the nucleic acid sequences are designed for in-solution capture of those genetic loci and/or regions, by hybridization, nucleic acid sequences are synthesized by inkjet printing on an array with a capacity of over 50,000 nucleic acid sequences (e.g., Agilent SureSelect), following synthesis. The nucleic acid sequences are cleaved from the substrate on which they were synthesized, for use in solution, the nucleic acid sequences thus synthesized constitute a pool which is expected to capture most or all of the genetic loci and/or regions on the list from all of the Mendelian pedigrees, and are used that way on each sample. The samples themselves may be processed in a pool (each identified by a nucleic acid barcode) or individually. Variants which matter for each Mendelian pedigree are bioinformatically separated out from the DNA sequencing-based assay data of (e). A separate report may be generated for each of the Mendelian pedigrees, even though a portion of their assays (synthesis of a shared oligo pool) was in common.

In some embodiments, the "genetic characteristics" of (b) constitute a list of genes derived from the clinical phenotype of the patient, using methods described in US 20160283484.

In some embodiments, (i) the original individual is among those sequenced with the personalized assay, and (ii) the sequencing depth of the personalized assay, at the loci of tentatively identified mosaic variants, is higher than in the original assay and thus can be used to make a more definitive variant call.

In some embodiments, the individual of (a) is a cancer patient, the first assay is sequencing of DNA derived from their tumor, the genetic characteristics determined in (b) are one or more of (i) variations of the DNA sequence so determined, from a human reference sequence, or (ii) alleles which match the human reference sequence but which are known to be correlated with some type of cancer or other disease, or (iii) alleles which determine the HLA type; optionally filtered to select those variants most likely to be relevant for analysis of the tumor or the patient's potential treatment, the DNA sequences designed in (c) are to capture or amplify the genomic regions of those variants, in subsequent samples, the assay of (e) is sequencing of DNA (or cDNA) captured or amplified using the array-synthesized oligos, the samples sequenced in (e) are from the same patient and are one or more of (i) germline DNA, (ii) tumor RNA or cDNA derived from the tumor RNA, (iii) cell-free DNA or RNA derived from blood plasma (including from different time points in the patient's progression), (iv) DNA from elsewhere in the patient's body which may contain mosaic variants, or (v) tumor DNA again (to confirm the new assay detects the variants seen with the original assay), the report generated attempts to identify genetic variants which can inform the therapy choice for the patient.

In some embodiments, the individual of (a) is a cancer patient, the first assay is sequencing of DNA derived from their tumor and also germline DNA, the genetic characteristics determined in (b) are one or more of (i) variations of the DNA sequence so determined, between the tumor sequence and the germline sequence, or (ii) alleles which determine the HLA type; optionally filtered to select those variants most likely to be relevant for analysis of the tumor or the patient's potential treatment, the DNA sequences designed in (c) are to capture or amplify the genomic regions of those variants, in subsequent samples, the assay of (e) is sequencing of DNA (or cDNA) captured or amplified using the array-synthesized oligos, the samples sequenced in (e) are from the same patient and are one or more of (i) tumor RNA or cDNA derived from the tumor RNA, (ii) cell-free DNA or RNA derived from blood plasma (including from different time points in the patient's progression), (iii) DNA from elsewhere in the patient's body which may contain mosaic variants, or (iv) tumor and/or germline DNA again (to confirm the new assay detects the variants seen with the original assay), the report generated attempts to identify genetic variants which can inform the therapy choice for the patient.

In some embodiments, the individual of (a) is a cancer patient, the first assay is sequencing of RNA derived from their tumor, or cDNA derived from RNA of their tumor, the genetic characteristics determined in (b) are one or more of (i) variations of the DNA sequence so determined, from a human reference sequence, or (ii) alleles which match the human reference sequence but which are known to be correlated with some type of cancer or other disease, or (iii) alleles which determine the HLA type, or (iv) metrics of gene expression and/or allele-specific expression, or (v) quantification of long non-coding RNAs or micro-RNAs which are at least partially tissue-type specific or cancer-type specific; optionally filtered to select those variants most likely to be relevant for analysis of the tumor or the patient's potential treatment, the DNA sequences designed in (c) are to capture or amplify the genomic regions of those variants, in subsequent samples, the assay of (e) is sequencing of DNA (or cDNA) captured or amplified using the array-synthesized oligos, the samples sequenced in (e) are from the same patient and are one or more of (i) germline DNA, (ii) tumor DNA, (iii) cell-free DNA or RNA derived from blood plasma (including from different time points in the patient's progression), (iv) DNA from elsewhere in the patient's body which may contain mosaic variants, or (v) tumor RNA again (to confirm the new assay detects the variants seen with the original assay), the report generated attempts to identify genetic variants which can inform the therapy choice for the patient.

In some embodiments, the individual of (a) is a cancer patient, the first assay is sequencing of cell-free DNA derived from the patient's blood plasma, the genetic characteristics determined in (b) are one or more of (i) variations of the DNA sequence so determined, from a human reference sequence, or (ii) alleles which match the human reference sequence but which are known to be correlated with some type of cancer or other disease, or (iii) alleles which determine the HLA type; optionally filtered to select those variants most likely to be relevant for analysis of the tumor or the patient's potential treatment, the DNA sequences designed in (c) are to capture or amplify the genomic regions of those variants, in subsequent samples, the assay of (e) is sequencing of DNA (or cDNA) captured or amplified using the array-synthesized oligos, the samples sequenced in (e) are from the same patient and are one or more of (i) germline DNA, (ii) cell-free DNA derived from the patient's blood plasma (but now potentially at greater sequencing depth by use of a more focused, oligo-directed assay) (including from different time points in the patient's progression), (iii) cell-free RNA derived from the patient's blood plasma (including from different time points in the patient's progression) (iv) DNA from elsewhere in the patient's body which may contain mosaic variants, or (v) cell-free DNA again (to confirm the new assay detects the variants seen with the original assay), the report generated attempts to identify genetic variants which can inform the therapy choice for the patient.

In some embodiments, the individual of (a) is a cancer patient, the first assay is sequencing of cell-free RNA derived from the patient's blood plasma, or cDNA derived from that RNA, the genetic characteristics determined in (b) are one or more of (i) variations of the DNA sequence so determined, from a human reference sequence, or (ii) alleles which match the human reference sequence but which are known to be correlated with some type of cancer or other disease, or (iii) alleles which determine the HLA type, or (iv) metrics of gene expression and/or allele-specific expression, or (v) quantification of long non-coding RNAs or micro-RNAs which are at least partially tissue-type specific or cancer-type specific; optionally filtered to select those variants most likely to be relevant for analysis of the tumor or the patient's potential treatment, the DNA sequences designed in (c) are to capture or amplify the genomic regions of those variants, in subsequent samples, assay of (e) is sequencing of DNA (or cDNA) captured or amplified using the array-synthesized oligos, the samples sequenced in (e) are from the same patient and are one or more of (i) germline DNA, (ii) cell-free RNA derived from blood plasma (but now potentially at greater sequencing depth by use of a more focused, oligo-directed assay), (iii) cell-free DNA from the patient's blood plasma, or (iv) DNA from elsewhere in the patient's body which may contain mosaic variants, or (v) cell-free RNA again (to confirm the new assay detects the variants seen with the original assay), the report generated attempts to identify genetic variants which can inform the therapy choice for the patient In some embodiments, the individual of (a) is a current or potential cancer patient, the first assay is quantification of RNAs derived from the patient's white blood cells, or cDNA derived from that RNA; and/or quantification of cell-free DNA and/or RNA in the blood plasma, the genetic characteristics determined in (b) are which genes and/or non-coding RNA regions are best for cell-free tumor characterization via cell-free DNA vs cell-free RNA, the DNA sequences designed in (c) are to capture or amplify the genomic regions best for cell-free tumor characterization via cell-free DNA and/or (separately, with a different group of DNA sequences) to capture or amplify the genomic regions best for cell-free tumor characterization via cell-free RNA, in subsequent samples, the assay of (e) is sequencing of cell-free DNA and/or cell-free RNA captured or amplified using the set(s) of array-synthesized oligos, the samples sequenced in (e) are from the same patient and are one or more of (i) cell-free DNA, or (ii) cell-free RNA; either derived from blood plasma; from the same or different time points in the patient's progression, and the report generated attempts to identify genetic variants which can inform the therapy choice for the patient.

In some embodiments, the individual of (a) is a current or potential cancer patient, the first assay is sequencing of DNA and/or RNA derived from the patient's tumor, optionally combined with sequencing of germline DNA, the genetic characteristics determined in (b) are a list of expressed variants seen in the tumor but not seen in the germline DNA, which have been assessed to be potential neoantigens for use in a personal cancer vaccine, the DNA sequences designed in (c) are to capture or amplify a plurality of the variants, in subsequent samples, the assay of (e) is sequencing of DNA or RNA, captured or amplified using the set(s) of array-synthesized oligos, with sufficient sequencing depth and analysis to detect mosaic variants, the sample(s) sequenced in (e) are from the same patient but from non-cancerous cells, from the same tissue as the tumor, or from other tissue elsewhere in the body; and may also include the tumor DNA (again, as a control for the new assay), the report generated attempts to discriminate which of these (apparently somatic) variants also exists in cells other than the cancer. This can occur due to mosaic variation (due to a DNA replication error or a retroviral insertion) which occurred prior to the initiation of the tumor. This can lead to variants which are in the tumor and other tissues but not the germline. These variants may be inappropriate as the basis for a personal cancer vaccine, since (i) the immune response elicited by such a vaccine might also attack non-cancer cells that express the same variant, and (ii) the patient may have been tolerized to peptides generated by the variant and thus not mount an immune response to them.

In some embodiments, the individual of (a) is a current or potential cancer patient, the first assay is relative quantification of RNA by gene and/or non-coding RNA region, in a sample from the patient, using targeted or untargeted cDNA sequencing or other assay approaches, the genetic characteristics determined in (b) are one or more lists of genes, non-coding RNA regions, or RNA from gene-fusion events, whose RNA sequencing read-depth would benefit from being increased or decreased relative to a non-personalized assay, in terms of achieving more uniform RNA sequencing coverage, the DNA sequences designed in (c) are to capture or amplify RNA (or cDNA) from genes and/or non-coding RNA regions and/or gene-fusion events on the lists, in subsequent samples, the assay of (e) is sequencing of RNA, (or cDNA), captured or amplified using the set(s) of array-synthesized oligos, the sample(s) sequenced in (e) are from the same patient, and may be (i) the same sample as assayed in (a), or (ii) another sample from the same tissue as assayed in (a) (e.g., to look for tumor heterogeneity), or (iii) one or more samples from different time points in a patient's progression, or (iv) from other patients being compared, the report generated includes one or more of (i) genetic variants called from the RNA sequencing data, or (ii) relative expression levels of different samples, by gene or non-coding RNA region, or (iii) allele-specific expression, where the variants being expressed may be SNP's, InDel's and/or gene fusion events.

In some embodiments, the assay of (a) is RNA sequencing of a sample, the list(s) generated as genetic characteristics in (b) are of genes, non-coding RNA regions and gene fusion events not sufficiently covered by the sequencing of (a), the sample of (e) is the same as (a), the assay of (e) is sequencing of RNA (or cDNA) captured or amplified by the oligos synthesized in (d), the data from (e) is added to that from (a), in an effort to fill in the otherwise insufficient (or suboptimal) DNA sequencing coverage from (a), in the genes and other regions identified in the lists.

In some embodiments, the assay of (a) is RNA sequencing (or sequencing of cDNA derived from RNA), using next generation sequencing methods, with less than five million sequence reads. In some embodiments, the assay of (a) is RNA sequencing (or sequencing of cDNA derived from RNA), using next generation sequencing methods, with less than one million sequence reads.

In some embodiments, the assay of (a) is DNA sequencing of a plurality of V(D)J recombination segments which each specify an antigen receptor of a T-cell and/or B-cell of a cancer patient's immune system, the genetic characteristics in (b) are the identities and quantities of specific V(D)J sequences, the DNA sequences designed in c, and array synthesized in (d), are to capture or amplify DNA or RNA sequences which would lead to neoantigens which can be recognized by the T-cell receptors or B-cell receptors corresponding to the V(D)J segments of s (a) and (b), the sample of (e) is from the same patient and is one of (i) tumor DNA, or (ii) tumor RNA, or (iii) cDNA derived from tumor RNA, or (iv) cell-free DNA from blood plasma, or (v) cell-free RNA from blood plasma, or (vi) cDNA derived from cell-free RNA from blood plasma, the assay of (e) is sequencing of DNA, RNA (or cDNA) captured or amplified by the oligos synthesized in (d), the data from (e) is to confirm the existence of genetic variants in the tumor of the patient, corresponding to the V(D)J segments measured in (a) and (optionally) to quantify those variants.

In some embodiments, the assay of (a) is sequencing of DNA, RNA or cDNA derived from a patient's tumor, directly from the tumor or from cell-free amounts in the patient's blood plasma, the genetic characteristics in (b) are the identities of variants, relative to a human reference sequence, found in the sequence data from (a), which may lead to immunologically active neoantigens, the DNA sequences designed in c, and array synthesized in (d), are to capture or amplify DNA sequences which would lead to T-cell receptors or B-cell receptors corresponding to the potential neoantigens of s (a) and (b), the sample of (e) is from the same patient and is one or more of (i) DNA from T-cells, or (ii) DNA from B-cells, the assay of (e) is sequencing of DNA captured or amplified by the oligos synthesized in (d), the data from (e) is to confirm the existence of, and optionally to quantify, V(D)J segments which would lead to T-cell or B-cell receptors corresponding to the neoantigens identified in s (a) and (b).

In some embodiments, the assay of (a) comprises (i) exposing a human tumor tissue sample to a mixture of oligo-antibody conjugates, some of which may bind to proteins or peptides in the tissue sample, (ii) subsequent release of those that bound, and (iii) sequencing of their oligo portions, the genetic characteristics of (b) are the identities and quantities of oligo-antibody conjugates corresponding to the sequences determined in (a), DNA sequences designed in c and array synthesized in (d) are to capture or amplify one or more of (i) a plurality of oligo sequences of oligo-antibody conjugates identified in (b), or (ii) DNA or RNA sequences corresponding to the proteins or peptides which were bound by the antibody component of oligo-antibody conjugates in (a), the sample(s) assayed in (e) are DNA or RNA (or cDNA derived from RNA) from the same or different tissue samples of the same person as the assay of (a), the assay of (e) is sequencing, with a report identifying the specific sequences and their quantities.

In some embodiments, the nucleic acid sample of the individual, measured by the assay in (a), is obtained distal to its origin in the body, the genetic characteristics determined in (b) include identified genomic locations of mosaic variants in the initial sample, the DNA sequences designed in c are designed to amplify or enrich a plurality of those mosaic loci in subsequent samples, the assay of (e) is performed on samples from one or more other locations in the body of the same individual, to see if and/or to what extent the same mosaic variants are observed in those samples, the report of (f) uses the data to determine where in the body the DNA of the original sample came from.

In some embodiments, the initial nucleic acid sample is one of (i) cell-free DNA or cell-free RNA obtained from blood plasma, or (ii) RNA obtained from one or more exosomes derived from a blood sample of the individual, or (iii) DNA or RNA obtained from circulating tumor cells, or (iv) DNA or RNA from a tumor metastasis.

In some embodiments, the initial nucleic acid sample is from what is thought to be a primary tumor, tested to confirm whether it is actually from the tissue within which it has been found.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG.", "Figure", and "FIGS." herein) of which:

DETAILED DESCRIPTION

Figure 1:
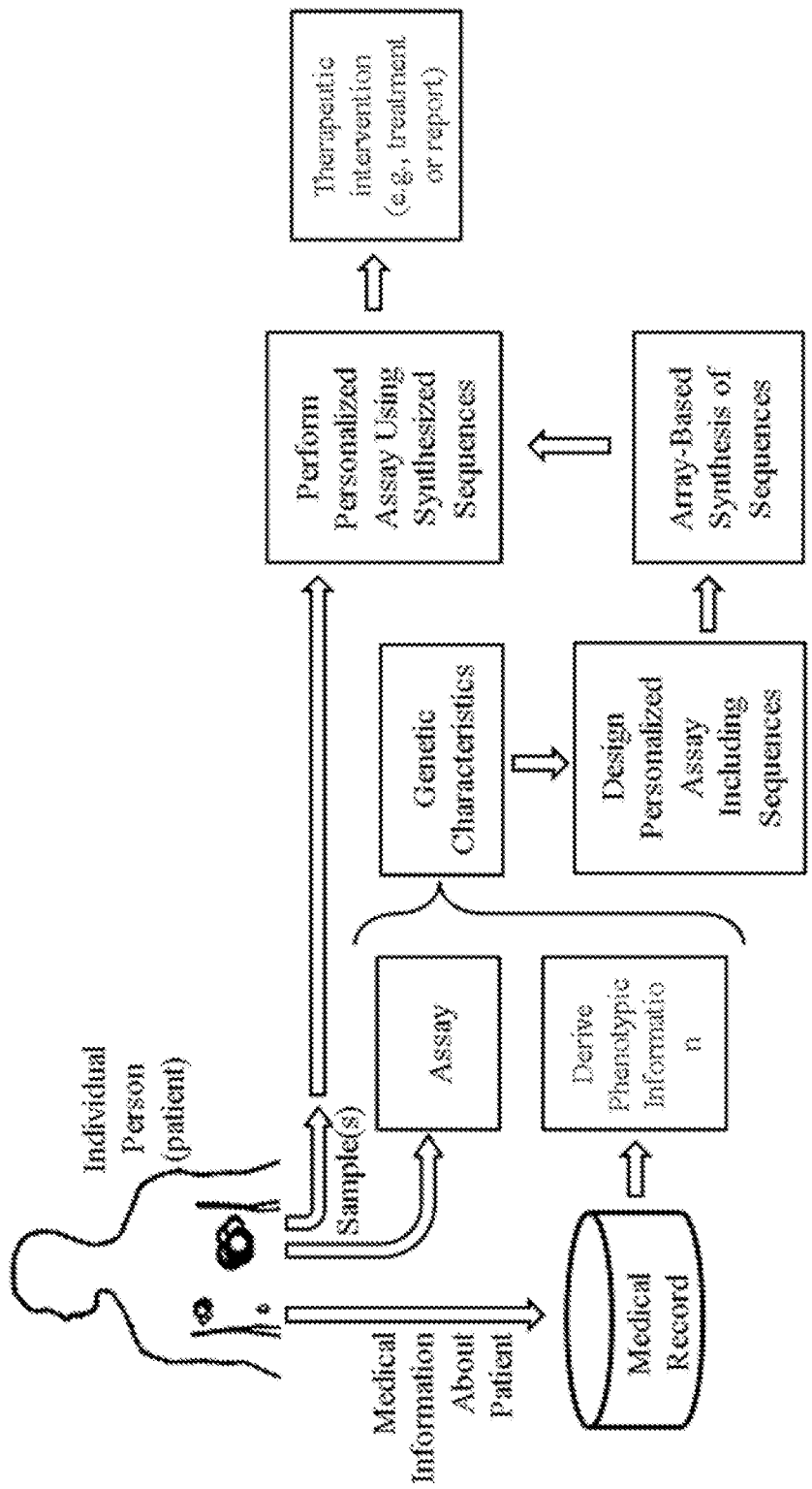
FIG. 1 shows the information flow and operations of a method of the present disclosure.

While various embodiments of the invention(s) of the present disclosure have been shown and described herein, it will be obvious to those skilled in the art that such embodiments are provided by way of example only. Numerous variations, changes, and substitutions may occur to those skilled in the art without departing from the invention(s). It should be understood that various alternatives to the embodiments of the invention(s) described herein may be employed in practicing any one of the inventions(s) set forth herein.

The term "subject," as used herein, generally refers to a subject having at least one biological sample that is undergoing analysis. The subject can be undergoing analysis to diagnose, predict or monitor a health, health condition, or well-being of the subject, such as, for example, identify or monitor a disease condition (e.g., cancer) in the subject. The subject can have a sample that is undergoing analysis by a researcher or a service provider, such as a healthcare professional or other individual or entity that employs methods and systems of the present disclosure to analyze the sample. The subject can be a patient. The subject can be a human, an animal or a plant.

The term "nucleic acid," as used herein, generally refers to a polymeric form of nucleotides of any length, for example, ribonucleotides, deoxyribonucleotides or peptide nucleic acids (PNAs). Nucleic acids comprise purine and pyrimidine bases, or other natural, chemically or biochemically modified, non-natural, or derivatized nucleotide bases. The backbone of the polynucleotide can comprise sugars and phosphate groups, as may typically be found in ribonucleic acid (RNA) or deoxynucleic acid (DNA), or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired. The nucleic acid molecule may be a DNA molecule. The nucleic acid molecule may be an RNA molecule.

The terms "variant or derivative of a nucleic acid molecule" and "derivative or variant of a nucleic acid molecule," as used herein, generally refer to a nucleic acid molecule comprising a polymorphism. The terms "variant or derivative of a nucleic acid molecule" or "derivative or variant of a nucleic acid molecule" may also refer to nucleic acid product that is produced from one or more assays conducted on the nucleic acid molecule. For example, a fragmented nucleic acid molecule, hybridized nucleic acid molecule (e.g., capture probe hybridized nucleic acid molecule, bead bound nucleic acid molecule), amplified nucleic acid molecule, isolated nucleic acid molecule, eluted nucleic acid molecule, and enriched nucleic acid molecule are variants or derivatives of the nucleic acid molecule.

The term "genetic variant," as used herein, generally refers to an alteration, variant or polymorphism in a nucleic acid sample or genome of a subject. Such alteration, variant or polymorphism can be with respect to a reference genome, which may be a reference genome of the subject or other individual. Single nucleotide polymorphisms (SNPs) are a form of polymorphisms. In some examples, one or more polymorphisms comprise one or more single nucleotide variations (SNVs), insertions, deletions, repeats, small insertions, small deletions, small repeats, structural variant junctions, variable length tandem repeats, and/or flanking sequences. Copy number variants (CNVs), transversions and other rearrangements are also forms of genetic variation. A genomic alternation may be a base change, insertion, deletion, repeat, copy number variation, or transversion.

The terms "detectable label" or "label," as used herein, generally refer to any chemical moiety attached to a nucleotide, nucleotide polymer, or nucleic acid binding factor. The attachment may be covalent or non-covalent. The label can be detectable and render the nucleotide or nucleotide polymer detectable to a user or a system operated by the user. The terms "detectable label" or "label" may be used interchangeably. Detectable labels that may be used in combination with the methods disclosed herein include, for example, a fluorescent label, a chemiluminescent label, a quencher, a radioactive label, biotin, quantum dot, gold, or a combination thereof. Detectable labels include luminescent molecules, fluorochromes, fluorescent quenching agents, colored molecules, radioisotopes or scintillants. Detectable labels also include any useful linker molecule (such as biotin, avidin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase and luciferase), electron donors/acceptors, acridinium esters, dyes and calorimetric substrates. It is also envisioned that a change in mass may be considered a detectable label, as is the case of surface plasmon resonance detection.

The terms "target-specific", "targeted", and "specific," can be used interchangeably and generally refer to a subset of the genome that is a region of interest, or a subset of the genome that comprises specific genes or genomic regions. For example, the specific genomic regions can be a region that is guanine and cytosine (GC) rich. Targeted sequencing methods can allow one to selectively capture genomic regions of interest from a nucleic acid sample prior to sequencing. Targeted sequencing involves alternate methods of sample preparation that produce libraries that represent a desired subset of the genome or to enrich the desired subset of the genome. The terms "untargeted sequencing" or "non-targeted sequencing" can be used interchangeably and generally refer to a sequencing method that does not target or enrich a region of interest in a nucleic acid sample. The terms "untargeted sequence", "non-targeted sequence" or "non-specific sequence," generally refer to the nucleic acid sequences that are not in a region of interest or to sequence data that is generated by a sequencing method that does not target or enrich a region of interest in a nucleic acid sample. The terms "untargeted sequence", "non-targeted sequence" or "non-specific sequence" can also refer to sequence that is outside of a region of interest. In some cases, sequencing data that is generated by a targeted sequencing method can comprise not only targeted sequences but also untargeted sequences.

The terms "probe," "nucleic acid probe," "capture probe," "bait," as used herein, generally refer to a nucleic acid molecule comprising a single-stranded portion capable of hybridizing to a complementary nucleic acid sequence. A probe can be used for detection or enrichment of nucleic acid molecules. A probe can be target-specific such that a region of interest may be pulled-down, isolated, enriched, amplified, or labeled. A probe can be used for targeted sequencing. A probe may hybridize to a targeted sequence when attached to a solid substrate or when in-solution, e.g. as for hybrid capture. A probe may be included in a set, or plurality, of probes. A probe set can comprise probes that overlap within a specific genomic region such that they are tiled or staggered. A probe set can include probes to a genomic region or a panel comprising multiple genomic regions. Probes can be amplification based or capture hybridization-based. Non-limiting examples of probes include molecular inversion probes, amplification probes, biotinylated affinity probes, or any probe comprising a detectable label.

The term "barcode," as used herein, generally refers to a short DNA sequence segment, which is generally part of a longer DNA sequence design. A barcode is typically a tag or identifier, which corresponds to a sample. This allows the sample to be pooled with others for processing, and subsequently be demultiplexed by leveraging the barcode sequence, either physically or bioinformatically.

The term "buccal swab," as used herein, generally refers to a method of obtaining a nucleic acid sample from an individual subject, by swabbing the inside of their cheek. Some of the cells obtained using this method are ectodermal in origin, and thus share early lineage and mosaic variants with the brain and other neurological tissue.

The term "cell-free DNA," as used herein, generally refers to DNA which is found circulating in the blood plasma, not contained in a cell. It is thought to originate in cells of the body which have died. Those may include blood cells (which typically only live a few days) or cancer tumor cells, which may die by apoptosis or necrosis. Dead cells that are broken up may release RNA, which can also end up in a cell-free format in the blood. Both cell-free DNA and RNA may be cleared from the blood by the liver, with a half-life in the blood of about 20 minutes.

The term "exome," as used herein, generally refers to sequencing the DNA of the coding regions of the genes. It may be implemented by methods, such as hybrid capture, which extract those portions of a DNA sample from the rest of the genome.

The term "exosome," as used herein, generally refers to a liquid bubble, encased by a flexible lipid membrane. In the human body, exosomes may be released from cells (e.g., as fragments of nucleic acid molecules from cells) and circulate in the blood stream. They may contain several types of RNA derived from those cells. If they are derived from a cancer tumor, the RNA they contain may be reflecting the mutations of the tumor itself. Because they are found in the blood circulation, they can be more accessible than a biopsy of the tumor may be.

The term "gastrulation," as used herein, generally refers to the point in development of a human embryo, when cells start to differentiate from the undifferentiated stem cells of a human embryo, into the germ layers and later other more specific cell types which make up the organs of the body. Gastrulation typically happens when a human embryo has about 200 cells, about 7 days after fertilization/conception.

The term "germ layer," as used herein, generally refers to the first three categories of human tissue to differentiate from the undifferentiated stem cells of a human embryo. There are three germ layers: Mesoderm, ectoderm and endoderm. Neural cells including the brain come from the ectoderm. Blood cells come from the mesoderm.

The term "hybrid capture," as used herein, generally refers to the in-solution capture of selected DNA molecules from a sample, by synthetic RNA molecules mixed into the same solution. The capture is by hybridization of complementary nucleic acid sequences. After the hybridization, the DNA/RNA hybrids can be selectively extracted from the solution. The RNA molecules can be synthesized with specific sequences, to allow targeting this capture process to very specific segments of the human genome, each typically a few hundred bases long. Hybrid capture can also be applied to complementary deoxyribonucleic acid (cDNA) derived from ribonucleic acid (RNA) in a sample.

The term "Mendelian," as used herein, generally refers to a disease or medical condition, inherited based on mutation of a single gene. Most Mendelian conditions are quite rare.

The term "mosaicism," as used herein, generally refers to genetic changes which occur after an embryo has started to develop. These changes will only be found in a fraction of the cells of a human body.

The term "neoantigen," as used herein, generally refers to a peptide derived from the mutated DNA sequence of a cancer tumor, which may elicit an immune response in the subject.

The term "Next Generation Sequencing" (NGS), as used herein, generally refers to technologies for massively parallel determination of the sequences of nucleic acid molecules, such as deoxyribonucleic acid (DNA) or ribonucleic acid (RNA) molecules. NGS was developed after, and has significantly replaced Sanger sequencing, which was considered the first generation DNA sequencing technology.

The term "oligo," as used herein, generally refers to an oligonucleotide, i.e., a single stranded synthetic nucleic acid molecule. It is the synthetic physical realization of a DNA (or RNA) sequence design.

The term "post-zygotic," as used herein, generally refers to the time after conception of a fetus, and initial cell division. At conception, the egg and sperm combine to form a single cell call a "zygote".

The term "RNA sequencing," as used herein, generally refers to (i) direct sequencing of the RNA itself, or (ii) the construction of cDNA from the RNA, followed by sequencing of the cDNA.

The term "somatic," as used herein, generally refers to a type of genetic variant in a human body which is only found in a cancer tumor, or cells derived from it. These genetic changes are thought to occur during cell divisions which lead to expansion of a tumor, but they may also have occurred in the lineage of a cancer stem cell leading up to the initiation of a tumor. Because these variants occur well after conception and growth of a fetus, they are a special form of mosaicism.

The term "transcriptome," as used herein, generally refers to sequencing many (e.g., 50 million) cDNA molecules, to determine gene expression, detect gene fusion and alternative splicing events, and detect genetic variants expressed in the RNA.

The term "V(D)J recombination," as used herein, generally refers to a rearrangement of a set of genetically inherited DNA segments, by a subject's adaptive immune system, so as to create T-cell and B-cell receptors which can bind to specific antigens.

The term "zygocity," as used herein, generally refers to the number of copies of a genetic variant in each cell. A variant is "homozygous" if all of the copies of the DNA in a cell have the variant. A variant is "heterozygous" in a cell if there are two copies of the DNA and only one contains the genetic variant.

The terms "bound", "hybridized", "conjugated", "attached", "linked" can be used interchangeably and generally refer to the association of an object to another object. The association of the two objects to each other may be from a covalent or non-covalent interaction. For example, a capture probe hybridized nucleic acid molecule refers a capture probe associated with a nucleic acid molecule. The capture probe and the nucleic acid molecule are in contact with each other. In another example, a bead bound nucleic acid molecule refers to a bead associated with a nucleic acid molecule.

Overview

Disclosed herein are methods and systems for interactive and personalized genetic testing. In a method for interactive or personalized genetic testing, initial information gathered on an individual subject (who may be a medical patient) may be used to design and synthesize chemical reagents. The chemical reagents may be used for further testing. By using information from a first operation to synthesize chemical reagents specific to the subject being tested, the subsequent testing may be better focused on the personal characteristics of the subject. This can yield information on the subject which is either more insightful, or less expensive, or both.

Methods and systems of the present disclosure may detect or determine one or more phenotypes of a subject, such as a disease, at an accuracy of at least about 60%, 70%, 80%, 85%, 90%, 95%, 96%, 97%, 98%, or 99%, in some cases without retesting. Such methods and systems may detect or determine a disease in a subject at a sensitivity of at least about 80%, 85%, 90%, 95%, 96%, 97%, 98%, or 99%.

In an aspect of the present disclosure, a method for personalized genetic testing comprises using a first assay, a sequencing assay, to sequence or quantify nucleic acid molecules from at least one biological sample of a subject, thereby generating nucleic acid sequence data. Next, the nucleic acid sequence data may be used to determine a plurality of genetic characteristics in the at least one biological sample of the subject. The plurality of genetic characteristics may include genetic variants in the nucleic acid molecules from the at least one biological sample. As an alternative or in addition, phenotypic information may be derived from a health or medical record of a subject. The health or medical record may be in one or more databases. Next, the plurality of genetic characteristics of the subject may be determined from the phenotypic information. The plurality of genetic characteristics may include genetic variants. The plurality of genetic characteristics may facilitate diagnosis, prognosis or improved health or medical treatment of the subject.

Next, the genetic characteristics may be used to determine a nucleic acid configuration of a second assay, which nucleic acid configuration includes nucleic acid sequences of a plurality of nucleic acid probe molecules. The nucleic acid sequences are selective for the genetic variants. The plurality of nucleic acid probe molecules may then be provided by, for example, (i) synthesizing the plurality of nucleic acid probe molecules using at least one array, and/or (ii) selecting the plurality of nucleic acid probe molecules from a collection of nucleic acid probe molecules. Next, the plurality of nucleic acid probe molecules may be used to perform at least the second assay on one or more biological samples from the subject or at least one biological relative of the subject, to generate data indicative of a presence or absence of at least a subset of the genetic variants in the subject or the at least one biological relative.

FIG. 1 illustrates information flow and operations of a method for personalized genetic testing. In a first operation, an affected subject is identified and information can be obtained from the individual one of two ways. A first assay, also referred to herein as a sequencing assay, may be performed to sequence or quantify the nucleic acid molecules from at least one biological sample of a subject, thereby generating nucleic acid sequence data. Alternatively, the second option is obtain the phenotypic information from a medical record. Next, in a second operation, the nucleic acid sequence data may be analyzed to determine a plurality of genetic characteristics in the at least one biological sample of the subject. The plurality of genetic characteristics may include genetic variants in the nucleic acid molecules from at least one biological sample. In a third operation, the genetic characteristics can be used to determine a nucleic acid configuration of a second assay. The nucleic acid configuration may include nucleic acid sequences of a plurality of nucleic acid probe molecules. The nucleic acid sequences can be selective for genetic variants.

In operation four, a plurality of nucleic acid probe molecules may be provided by (i) synthesizing the plurality of nucleic acid probe molecules using at least one array, or (ii) selecting the plurality of nucleic acid probe molecules from a collection of nucleic acid probe molecules.

In operation five, using the nucleic acid probe molecules, a second assay may be performed on one or more biological samples from the subject or at least one biological relative of the subject. This assay can generate data indicative of a presence or absence of at least a subset of the genetic variants in the subject or at least one biological relative. In operation six, a therapeutic intervention may be determined from the two assays. The therapeutic intervention may be a treatment or a report. The report can compare the results from the first and second assay. The report may also compare the results among multiple samples of the second assay.

Initial information may be based on a first laboratory assay, applied to a sample obtained from the subject (e.g., a blood sample, tumor biopsy, etc). The initial information may be phenotypic, such as from a medical record of the subject. In either case, this initial information can be sufficiently specific to allow the design and synthesis of chemical reagents specific to the subject being tested.

Further testing of the personalized chemical reagents may be selected from a group consisting of additional analysis of the original sample from the subject, analysis of one or more other samples from the same subject, analysis of samples from other subjects who may share some of the same personal genetic characteristics (e.g., relatives of the subject), or a combination of the above. Information from the first assay can be used to design and synthesize chemical reagents. This information may allow better and/or less expensive testing of the subsequent samples.

The data from subsequent analysis may be useful on its own. The data may be useful in comparison to the initial information. Additionally, multiple samples from one or more subjects may be assayed using the personalized reagents. The results may be useful by comparison of the results between those samples and/or subjects. These uses may result in a report. The reports may be read by a physician, a researcher, and/or a regulatory authority.

The interactive nature of methods and systems of the present disclosure may be facilitated by information flowing between the operations. The information may be in the form of naturally occurring or synthetic molecules, or it may be in the form of data, such as may be stored in a computer. Where the information is in the form of molecules, it may be stored in particular in the form of information-containing biological polymers such as DNA, RNA, cDNA, proteins, peptides, antibodies, and combinations of these (e.g., antibody-oligo conjugates).

In an aspect of the present disclosure, the information flow may begin with data on an individual subject. It may exist in digital form in the patient's medical record, or it may be in the form of naturally occurring biological molecules in the subject's body. In the latter case, it can be converted to digital form by conducting a first assay, such as DNA sequencing. Next, specific genetic characteristics may be extracted from that data (e.g., identifying genetic variants of the subject's genome relative to a reference sequence, or predicting specific variants which they may have based on their medical records).

The information flow may then proceed from digital form into molecular form. In particular, the digitally stored genetic characteristics of the subject may be used to design and synthesize a set of DNA and/or RNA sequences for use in a subsequent assay to be performed on one or more subsequent samples. The personalized reagents may be a set of DNA and/or RNA sequences.

Methods of the present disclosure may be capable of handling large rich data sets. In particular, during the stage where the genetic characteristics are used to design and synthesize a set of DNA and/or RNA sequences, (i.e., the information is converted from digital to molecular form), array-based methods may be applied. Some of the array-based method can generate mixed pools of over 50,000 different individual DNA sequences. One such array can contain over five million letters of DNA sequence information, with a high degree of personalization of oligo pools. For example, a printer copy of the personalization can fill a book with at least about 400, at least about 450, at least about 500, at least about 550, at least about 600, at least about 650, or at least about 700 pages long. Since large scale data storage in DNA is a recent advance, the present disclosure can further design each "book" to be an active chemical reagent, used for innovative personally-tailored types of genetic testing. The methods can also allow this approach to be affordable, In another aspect of the presented disclosure, the methods presented may allow for cost effective use of the synthesized custom DNA array on a personal basis. These methods may be selected from a group consisting of methods to share custom array synthesis over multiple clinical cases, methods to demultiplex an oligo pool after combined synthesis, applications in which multiple samples can be beneficially analyzed using reagents designed for a subject (so as to amortize the cost of custom personal reagent synthesis over multiple assays), and others.

Next, information can flow back into digital form, by using the array-synthesized DNA pools to execute assays on the second sample or set of samples. The readout of this second set of assays can inform a final report, which may be created in digital form for storage, transmission, printing and/or reading. In another aspect, a set of specific medical and research applications of this process may be disclosed.

Figure 5:
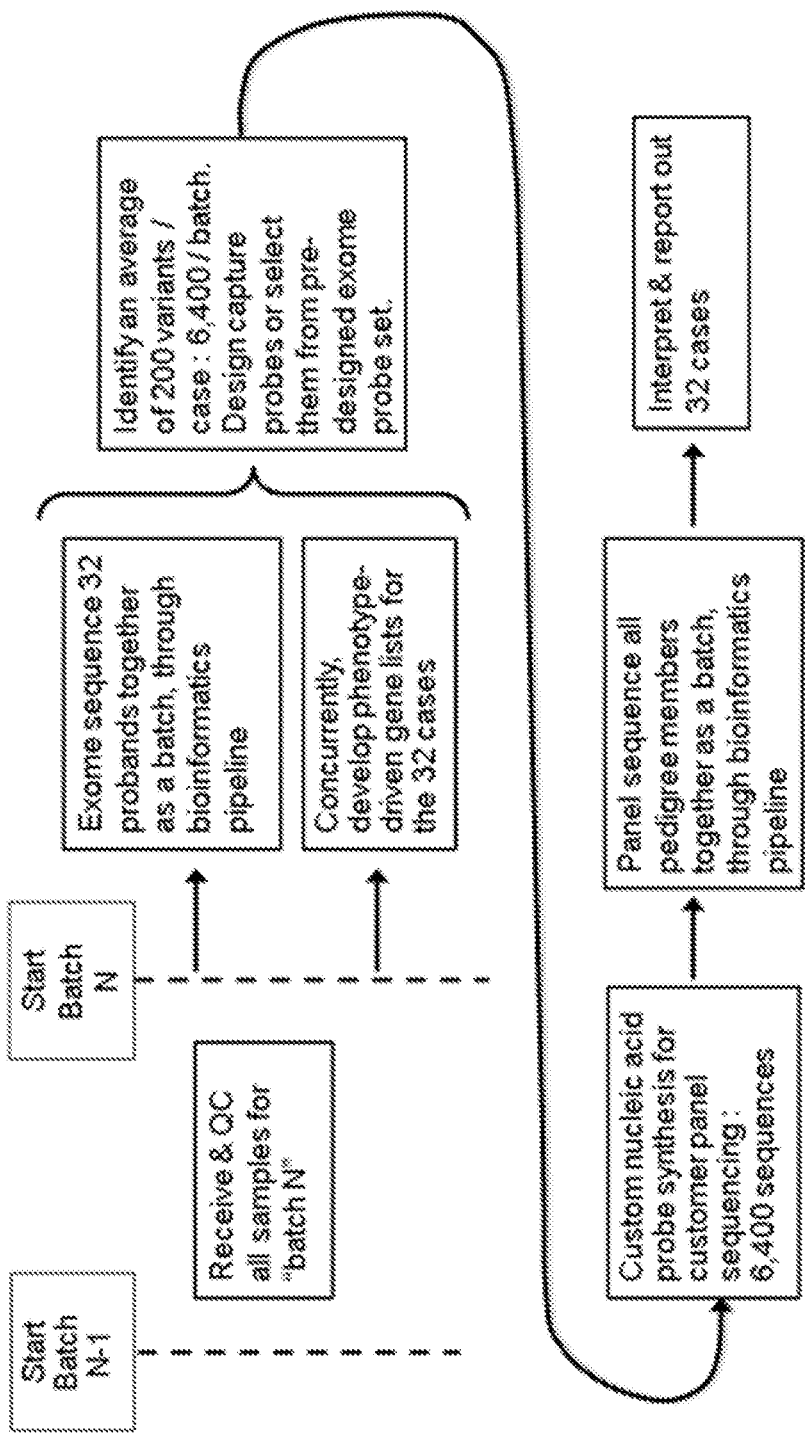
FIG. 5 shows an example workflow for period batches of 32 Mendelian cases, each batch sharing an array-synthesis of the sequences that may be needed for personalized assays for the 32 cases.

FIG. 5 illustrates an example workflow for period batches of 32 Mendelian cases. Each batch may share an array-synthesis of the sequences that may be needed for personalized assays for the 32 cases. In a first operation, an affected subject is identified. All samples may be received and quantified for batch N. The information can be obtained from the subject in two ways. 32 probands may be exome sequences as a batch, thereby generating nucleic acid sequence data. Concurrently, the phenotype-driven gene list may be obtained from a medical record. Next, the nucleic acid sequence data can be analyzed to identify an average of 200 variants/case or 6,400 probes/batch. The plurality of genetic characteristics may include genetic variants in the nucleic acid molecules. Capture probes can then be designed or selected from a pre-designed exome probe set. In the next operation, a plurality of nucleic acid probe molecules may be provided by custom nucleic acid probe synthesis for the consumer panel sequencing (e.g., 6,400 sequences). In the next operation, using the nucleic acid probe molecules, a second assay can be performed on one or more biological samples from the subject or at least one biological relative of the subject. This assay may generate data indicative of a presence or absence of at least a subset of the genetic variants in the subject or at least one biological relative. Next, all pedigree members can be panel sequenced as a batch, through bioinformatics pipelines. The therapeutic intervention may be a treatment or a report.

Obtaining Initial Information on the Subject by a First Assay

The information flow of the present disclosure may begin either with the medical record of the subject, or with information-containing molecules in the subject's body. These molecules may include, for example, DNA, RNA or proteins. The information revealed may be in the form of sequence data (i.e., the order of the bases or nucleic acids which make up these polymers) or the quantities of specific sequences in the sample. If the information is initially molecular, it may be extracted from a sample from the subject's body, for example, using an assay.

In one example, RNA information may be converted to cDNA. In another example, proteins may be converted to DNA by the use of oligo-antibody conjugates. The antibody portion of these molecules can bind to proteins with remarkable specificity, and the oligo (i.e., short DNA fragment) part of each conjugate can be a DNA barcode corresponding uniquely to a specific antibody (and hence protein). One oligo-antibody conjugate can bind to each protein. This one-to-one correspondence can be used to convert protein sequence and quantity information into oligo sequences. The antibodies can be selective not only at the level of a protein's amino acid sequence, but also at the level of post-translational modifications of a protein, such as phosphorylation or acetylation. Using these conjugates as transducers, DNA sequencing technologies can then be used to read out the oligo-stored information.

When sequencing DNA directly from a sample, one can choose whether to sequence it without discrimination, i.e., to sequence DNA molecules from the whole human genome, or to sequence a selected subset. Exome sequencing can begin by enriching a sample for a subset. The sample may be DNA molecules. The DNA molecules may originate from or overlap with coding regions of the genes. Sequencing a panel of genes may involve enrichment of a sample. When sequencing RNA, cDNA derived from the RNA may be sequenced to capture the equivalent information. In some cases, when sequencing proteins, oligo portions of oligo-antibody conjugates which bound to the sample may be sequenced.

When performing DNA sequencing, there are now a number of technical approaches which can sequence with enough throughputs to be practically useful for methods provided herein. In another aspect of the present disclosure, there are numerous technical approaches to sequence with enough throughputs to be practically useful at the scale of information flow. These technical approaches may be selected from a group consisting of (i) sequencing by synthesis with a reversible terminator chemistry, or (ii) pyrosequencing, with either optical or electronic readout, or (iii) nanopore sequencing, or (iv) real-time single molecule sequencing. These are exemplified by systems commercialized by (i) Illumina, or (ii) Thermo Fischer Scientific's Ion Torrent product line, or (iii) Oxford Nanopore, or (iv) Pacific Biosciences.

Types of Samples and Nucleic Acids Derived Therefrom

To obtain the desired information from the subject using the first or sequencing assay, specific sample types may be chosen for specific applications.

In an aspect of the present disclosure, it may be desirable to obtain a sample reflective of the germline genome of the subject, inherited from their parents, plus any de novo variants. Samples used to obtain this type of information may include nucleated blood cells such as white blood cells, non-cancerous cells embedded in or adjacent to a tumor or metastasis, or cell-free nucleic acids obtained from the blood plasma. In particular, in the case of a leukemia subject, the white blood cells may contain cancer and may be inappropriate as a sample of the germline genome. In those cases, cell-free nucleic acids in the blood plasma may contain nucleic acids which originate in other cells of the body which are non-cancerous, and can serve as germline reference relative to the cancerous white blood cells.

For certain applications, it may be desirable to obtain a sample which is reflective of the germline genome of the subject plus certain mosaic variants which have occurred post-zygotically. Even more specifically, it may be desirable to obtain a sample which reflects mosaic variants which occurred post-gastrulation, and which may be more concentrated in certain germ layers (e.g., the ectoderm, endoderm or mesoderm). A sample type which is reflective of ectodermal mosaic variation can be a buccal swab.

In another aspect, it may be desirable to obtain a sample which contains nucleic acids derived from a tumor (primary or metastatic), representing their cancer genome.

In another aspect, it may be desirable to obtain a sample which reflects post-zygotic V(D)J recombination which has occurred in cells of the subject's immune system. In particular, these may include T-cells and/or B-cells from the blood of the subject. The T-cells and/or B-cells may have infiltrated a tumor of the subject.

In certain applications, it may be desirable to obtain a sample which reflects non-human nucleic acids derived from the subject. The sample may reflect the genome(s) of one or more microbial species (bacteria or viruses), including those which may be, or which may already have been, oncogenic.

Combinations of Samples and of Nucleic Acids Derived Therefrom

In an aspect of the present disclosure, it may desirable in operation (a) to obtain a single sample from the subject. It also may be desirable to obtain a plurality of samples for use in operation (a).

During cancer, it may be desirable to obtain one or more samples reflective of the cancer genome, and also one or more samples reflective of the germline genome. It may also be desirable to obtain DNA and separately RNA from a tumor of the subject.

Lastly, it may be desirable to obtain nucleic acids from a sample of a tumor of the subject, and also nucleic acids circulating in the blood plasma of the subject.

Genetic Characteristics

During the second operation of the information flow, one or more specific genetic characteristics may be extracted from the data of the first operation. The genetic characteristics selected for extraction may be chosen so as to guide the later design and array-based synthesis of nucleic acids to be used in one or more assays for personalized genetic testing.

The genetic characteristics of this operation may include differences between the genetic characteristics of the subject and those of a human reference sequence. Those differences (variants) may be selected from a group consisting of single base substitutions (also called Single Nucleotide Polymorphisms, or SNPs), multiple nucleotide base substitutions (Multiple Nucleotide Polymorphisms, or MNPs), Insertions or Deletions (also referred to as InDels), or Copy Number Variations (CNVs) or Structural Variations (SVs).

The genetic characteristics may combine multiple genetic variants into a signature. For example, HLA type and ABO blood type, but may also include gene expression signatures and other combinations.

The genetic variants may be in the germline genome of the subject (including both inherited variants and de novo variants). They may also be variants which originated post-zygotically. These may include mosaic or somatic variants, or V(D)J recombination.

The genetic characteristics may include levels of RNA expression, for example at the level of whole genes, at the level of specific transcripts, at the level of specific variants (i.e., allele-specific expression), or the levels of non-coding RNAs. They may also include levels of methylation or other forms of epigenetic information determined from the sample.

The genetic characteristics may also include the quantity of sequences derived from oligo-antibody conjugates bound to, or depleted by binding to, proteins or peptides in the sample(s).

Where the genetic characteristics are quantitative, they may be absolute or relative. The genetic characteristics may quantitate the actual biological molecules of the sample(s) or they may quantitate one or more indirect metrics related to the biological molecules, such as the number of sequence reads of different types which result from an assay of the sample(s).

Design of Nucleic Acid Sequences for Subsequent Array-Based Synthesis and Use in a Second, Personalized, Assay During the third operation of the information flow, the genetic characteristics of the subject may be used to design (e.g., generate or engineer) a second assay. The genetic characteristics may also be used to design a set of nucleic acid sequences. The DNA sequences synthesized in the fourth operation may be used in the personalized assay of the last operation.

The sequences designed in the third operation, and synthesized in the fourth operation, can direct the personalized assay onto regions of the genome, which may include those guided by the subject's initially determined genetic characteristics. This is accomplished in order to obtain more detailed analysis in the same sample, and/or for corresponding analysis of other genetically related samples (from the same subject and/or genetically-related subjects). The personalized assay may be enabled by the DNA sequences. The synthesized oligonucleotides may hybridize with the nucleic acids of (or derived from) the sample. Following this hybridization, those oligonucleotides not hybridized may be washed away. The oligonucleotides that are hybridized may be pulled out of solution by mechanisms selected from the group consisting of streptavidin binding, magnetic bead pullout, and other methods.

Alternatively, the personalized assay enabled by these DNA sequences may use the DNA sequences for amplification. The synthesized DNA sequences may prime enzymatic extension of the DNA. For example, a polymerase may hybridize a single-stranded synthesized nucleic acid to a complementary target in single stranded nucleic acid molecules of, or derived from, the sample. This can form a double-stranded nucleic acid segment. This segment can then be used as the starting point for enzymatic extension. The enzymatic extension may be single base extension (including extension with a labeled or otherwise distinguishable nucleotide), a multiple-base extension (as in the gap filling of a molecular inversion probe—MIP), or it can include repeated cycles of priming and extension leading to amplification. This amplification can be exponential (as in a polymerase chain reaction (PCR)), linear, or other combinations.

By the methods described above or elsewhere herein, the array-synthesized nucleic acids may be used to enrich or deplete a nucleic acid mixture of those nucleic acid molecules, which can include specific locations, for example, in, or regions of, the human genome, or of microbial genomes, or of sets of oligo-antibody conjugates.

The DNA sequences designed in this operation may correspond, in whole or in part, to loci and/or regions of the target genome. They may also include one or more segments which are not related to the target genome, for other purposes. In one such approach, the segment not related to the target genome may be a nucleic acid barcode, for example, a sequence designed to convey information, or to be used as an identifier. Barcode sequence segments of this type may later be used for physical (e.g., hybridization-based) used for the capture of a subset of molecules, or they may be used for bioinformatic segmentation of a data set derived from them, or for other purposes.

In another example, the segments of the nucleic acid sequences, not related to the target genome, may be primers or priming sites for enzymatic extension and/or amplification, and they may contain other functional features (e.g., recognition sequences for restriction enzymes, as used in a molecular inversion probe).

Figure 3:
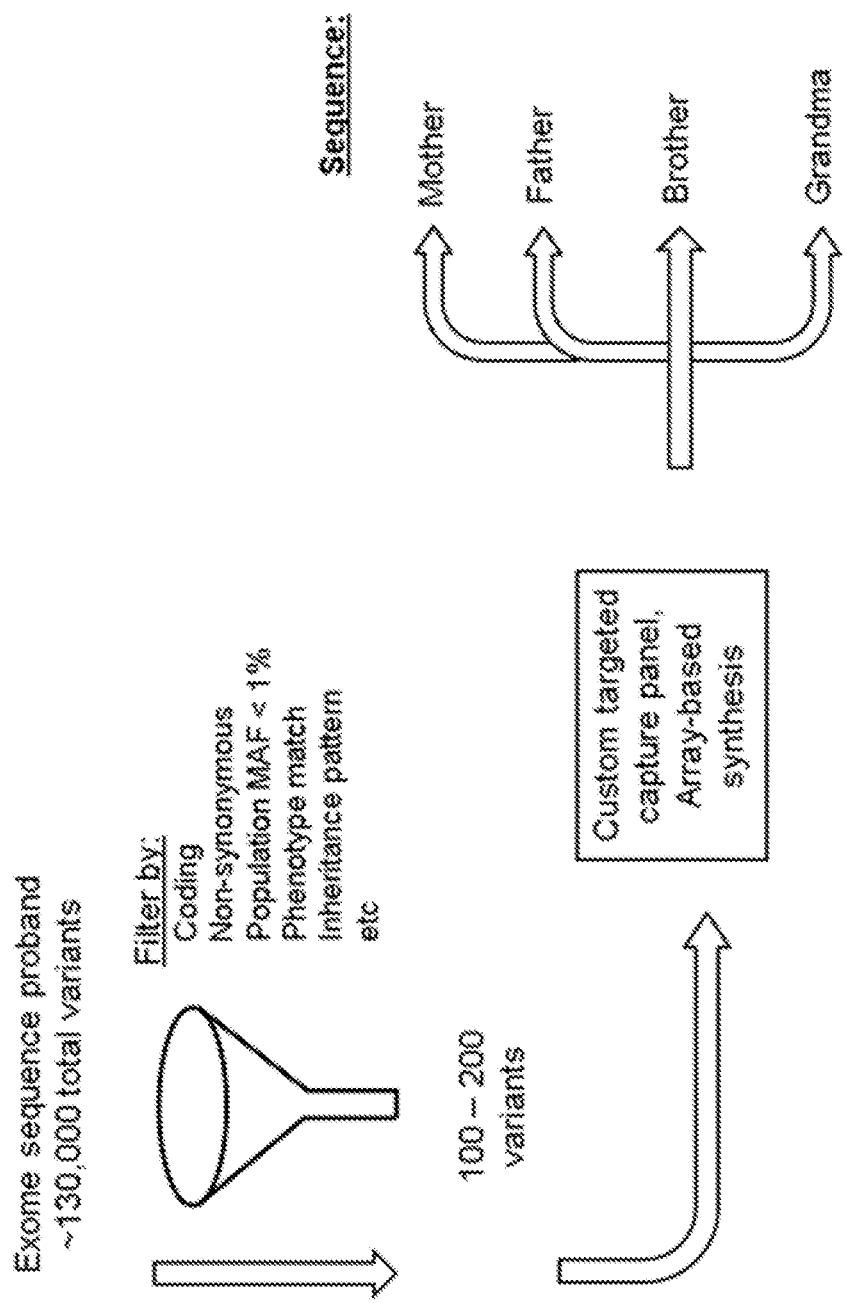
FIG. 3 shows a manner in which methods and systems of the present disclosure may be used to significantly lower the cost of sequencing family (pedigree) members.

FIG. 3 shows a manner in which methods and systems of the present disclosure may be used to significantly lower the cost of sequencing family (pedigree) members. In the first operation, DNA from one of the affected subjects of the pedigree may be exome sequenced. The data may be analyzed to identify variants relative to the human reference sequence. At least about 1000, 10,000, 50,000, 100,000, 130,000, or 150,000 variants can be identified. This list may then be filtered bioinformatically. The list may be filtered by factors including coding, non-synonymous variants, minor allele frequency population at most about 1%, phenotype match, and inheritance. For example, the list may be filtered bioinformatically to identify which of those variants are non-synonymous (i.e., they may be expected to change the amino acid sequence of the protein expressed by this gene). This list can then be further filtered bioinformatically to identify variants which have allele frequencies in the population below a cutoff, e.g., 1% (as may be expected for a variant causing a rare disease). The variants may be narrowed to at most about 500 variants. The variants may be narrowed to at most about 600 variants, 700 variants, 800 variants, 1000 variants, 1500 variants. The number of variants assayed may require a one-to-one ratio (or more) of variants to synthesized sequences. As a non-limiting example, 500 variants may require the synthesis of at least about 500 sequences. The genomic region captured by each probe can be at least about 350 bases. Therefore, for at least about 500 sequences, the footprint of this assay may be about 175,000 bases. Compared to an exome, where the footprint of the assay is typically at least 35 million bases, this may result in 200× less sequencing. This dramatic reduction in the amount of sequencing required, per additional family pedigree member, can make it much more affordable to sequence additional pedigree members (e.g., the parents and other children of the same parents).

The number of nucleic acid sequences which can be synthesized most economically on an array may be larger than the number needed for the planned subsequent personal assay of a specific subject or clinical case. In addition, the cost of the synthesis of such an array may be larger than can be justified by the value of a personalized assay of a single specific subject or clinical case. As a result, the array may have enough capacity to synthesize all of the subject-specific sequences needed for the personalized assays of a plurality of subjects. This may allow for amortizing the cost of an array-based synthesis over that plurality of subjects, thus lowering the cost per subject.

When multiple nucleic acid sequences are synthesized on an array, and subsequently cleaved from that common substrate, they may become intermingled in a pool. They can be used in that form for assays (e.g., targeted next generation DNA sequencing) which beneficially multiplex a plurality of genomic targets. In this case, data from the plurality of genomic targets can be de-multiplexed downstream by alignment of the sequences to a reference sequence.

Figure 4:
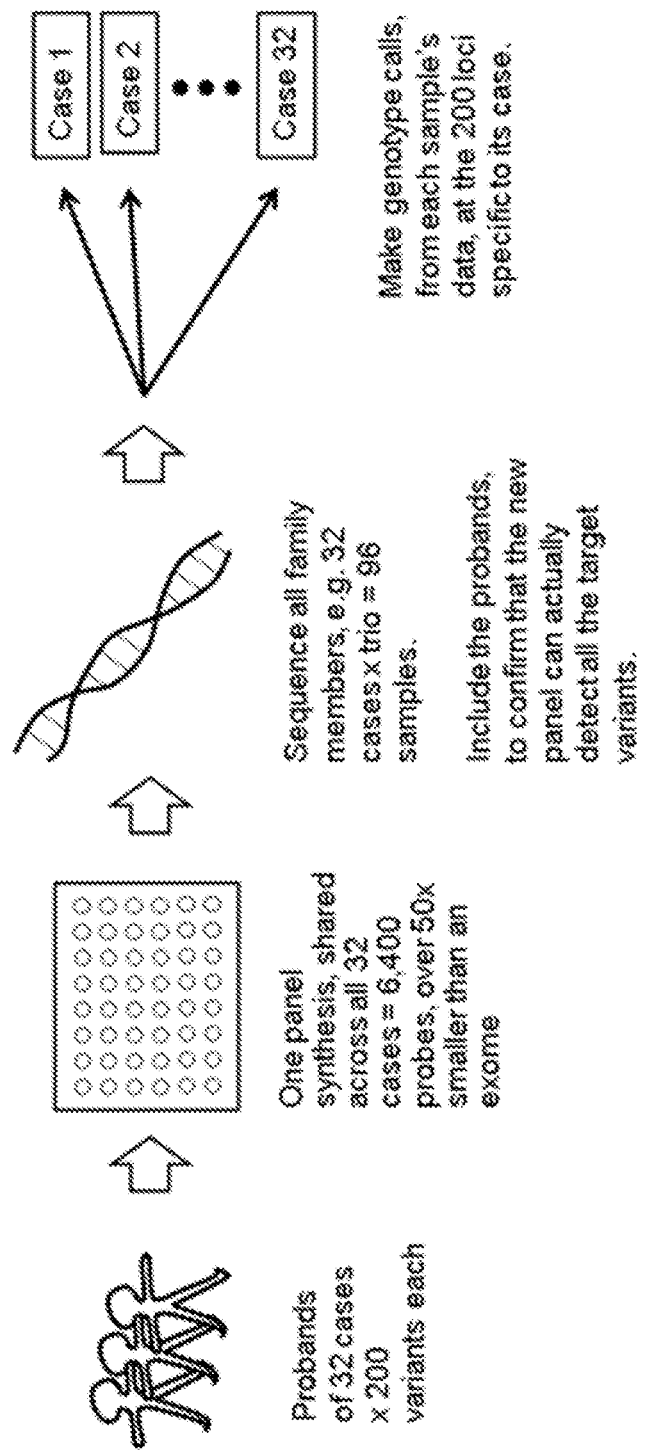
FIG. 4 shows an example of how custom array-based synthesis of oligonucleotides for personal assays, for example for 32 cases, can be shared, substantially lowering the synthesis cost per case.

FIG. 4 shows an example of how custom array-based synthesis of oligonucleotides for personal assays, for example for 32 cases, can be shared, substantially lowering the synthesis cost per case. The saving in sequencing costs may be partially or even completely offset by the cost of synthesizing an array of hybrid capture probes. To address this, the capture probes for each of several independent clinical cases can be synthesized on a single array (the arrays used in Agilent's system for example, have a capacity up to about 55,000 probes/array). If 32 clinical cases are combined in a single array one panel synthesis, at 200 probes each, the total may be 6,400 probes, still well within the capacity of the array. This amortizes the cost of array synthesis over the 32 cases. If the probes are not de-multiplexed post-synthesis, their footprints will be additive and thus be approximately 175,000 bases/case×32 cases=5.6 million bases. This is at least a 10× reduction in sequencing footprint versus performing exome sequencing on each of the other family members of each of the pedigrees. Next, all family members may be sequenced. For example, 32 cases× 3=96 samples. The probands may be included to confirm that the new panel can detect all the target variants. This assay may generate data indicative of a presence or absence of at least a subset of the genetic variants in the subjects and at least one biological relative. Genotype analysis can be performed from the sample's data, at the 200 loci specific to its case.

If the subject-specific sequences for multiple subjects are synthesized together on a single array, each subject subsequently assayed may generate data not only for their own genomic regions of interest, but also for the genomic regions of interest in other subjects. For each subject, the data from the genomic regions selected for other subjects may be irrelevant. Depending on the specific configuration, this unwanted data may also add to the cost of the personalized assays. If that additional cost is burdensome, it may be a barrier to the use of personalized assays based on array-synthesis of nucleic acids. If the DNA sequences are designed with two or more segments, one corresponding to the target regions of the genome and one or more not, then the segments not corresponding to the target regions of the genome can be used to physically separate, or enrich, the synthesized molecules post synthesis. Thus subject-specific sequences for a plurality of subjects can be synthesized together on an array, and be separated out post-synthesis. This post-synthesis separation can be driven by the segments of the sequences which were not related to the target regions of the genome (e.g., the barcodes or other segment designs).

For example, the subject-specific nucleic acid sequences can each be designed to have one segment corresponding to the genomic regions of interest for that subject, and a second segment with a barcode sequence corresponding to that subject. That barcode sequence can then be used after array-based synthesis to capture just the nucleic acid molecules synthesized for a specific subject. Once the nucleic acid molecules synthesized for just one subject have been physically separated out from the rest of the pool, they can be used for a personalized assay specific to just that subject. This separation may not need to be absolute to address the cost problem.

In another example, the subject-specific nucleic acid sequences can each be designed to have two segments not related to the genomic regions of interest to that subject. These two segments can then be used after array-based synthesis, to amplify just the sequences needed for the personalized assay for that subject. The amplification may be done separately for each of the subjects whose sequences were synthesized together on a single array.

By designing sequences, each with at least one segment not corresponding to a genomic region, the pool of oligonucleotides which exists post synthesis can be partitioned for separate uses. Those uses can include different processing of different groups of genomic content, from the same person (or people related to them). Those uses can also include separate processing and subject-specific analyses of unrelated subjects.

The performance of synthesized nucleic acid sequences in a personalized assay may vary depending on many conditions of the nucleic acid sequence (e.g., % GC, alignment degeneracy, primer-dimer formation) and the parameters of the assay. This assay performance uncertainty may make personal assay synthesis unattractive. However, a large set of DNA sequences may be designed, synthesized and tested in advance. Such a set can be, for example, a set of sequences to target every exon of every gene in the human genome. Data from this testing can provide validation of the sequences which worked satisfactorily, and feedback to guide the redesign and re-synthesis of sequences where the performance of the original design was not satisfactory. By this method, a library of previously designed, tested and validated sequences can be obtained. Then, when it is time to create a personalized assay for a specific subject, the DNA sequences designed for that subject can include sequences from the pre-validated library. This method can reduce the uncertainty of personalized assay performance and reduce the cost of, and time required to, design a set of sequences for a subject-specific assay.

The performance of an individual synthesized DNA sequence in an assay can also depend on the extent to which the DNA sequence used in the assay matches the region targeted in the nucleic acids derived from actual sample from the subject. Because subjects vary from the human reference in some of their nucleic acid sequences, the performance of an assay targeting the genomic region of a variant may depend on the allele of the variant in the subject being tested. It can be an advantage for a personalized genetic assay to optimize for the alleles actually present in that subject. In particular, if specific variant alleles are detected in the initial assay of the subject, then the sequences designed for the subsequent personalized assay can be based on those variant alleles. This may lead to better assay performance and reduce or eliminate allele-specific assay bias which may otherwise occur. While this principle is applicable to all variant types, it may have the highest benefit in variants which include multiple bases (e.g., multiple nucleotide polymorphisms, insertions or deletions ("InDels"), gene fusions, copy number variation, splice variants, and other forms of structural variation).

Array-Based Synthesis of Nucleic Acid Sequences

Array-based synthesis of multiple nucleic acid sequences on a common substrate can have varying degrees of parallelism. The optimal parallelism can vary by application, and by the use of post-synthesis de-multiplexing. The optimal parallelism for an application may be at least about 100 or at least about 1,000, or at least about 10,000 or at least about 50,000 nucleic acid sequences synthesized together on a common substrate, The optimum parallelism may be changed if the nucleic acids sequences synthesized in parallel on a common substrate are in spatially distinct regions of the substrate, separated a gap. In particular, if the gap is large enough to allow physical partitioning of the substrate after nucleic acid synthesis without damaging any of the nucleic acid molecules synthesized (e.g., wafer dicing) then the nucleic acid molecules can be partitioned without post-synthesis de-multiplexing from a pool.

The optimal nucleic acid length may depend on the synthesis methods used and the cost, synthesis time, sequence-purity of the synthesis method vs the length synthesized. It also may depend on whether the sequence consists of one segment (designed to be complementary to a genomic target), two segments (with the second segment being for example a barcode), three segments (with the 2nd and 3rd segments being for example primers or priming sites for amplification) or other multi-segment structures. Thus the optimum length may be at least about 50 bases, at least about 100 bases, at least about 150, at least about 200, at least about 250, or at least about 300 bases. The method of array-based nucleic acid synthesis may be photolithographic, by reagents dispensed in a jet from a moveable print head. Non-limiting examples of methods for synthesizing probes include in situ synthesis with or without photolithography and in situ synthesis using inkjet technology. Methods of synthesizing arrays or probes using photolithography may use masking and/or may use a digital micromirror device. Other examples of array synthesis are provided in U.S. Pat. Nos. 5,412,087; 6,045,996; 7,534,561; 8,415,101; 8,026,094, the disclosures of which are hereby incorporated by reference.

Methods to Use a Single Nucleic Acid Synthesis Array for Multiple Independent Cases The capacity of an array (i.e., the number of sequences which can be synthesized on a single solid substrate) can be shared by synthesis of sequences for the testing of multiple otherwise unrelated testing cases. This can amortize the cost of array synthesis over multiple cases, thus lowering the synthesis cost per case.

When sequences for multiple independent testing cases are synthesized together on a common substrate, they (or the information streams they represent) can be separated post-synthesis to the cases for which they were designed, by at least one of:

(i) mechanical partitioning of the substrate post synthesis but prior to cleavage of the nucleic acids from the substrate, or (ii) using one or more segments of each of the nucleic acid sequences to represent the subject for whose case the rest of the sequence is being synthesized (i.e., a nucleic acid barcode, or primer(s) or priming site(s)) so that after the nucleic acids have been cleaved from the substrate into a common pool, they can be segregated by methods of molecular biology (e.g., hybridization, amplification or others) for use in assays related just to individual cases, or (iii) bioinformatic segregation of data from the personalized assays, either based on the barcoding mentioned above, or by alignment of the sequences resulting from the personalized assay to a reference sequence and then partitioning the data based on genomic regions corresponding to specific cases.

Types of Genetic Analyses Personalized Using Array-Synthesized Nucleic Acids

In an aspect of the present disclosure, the array synthesis of nucleic acid molecules may create personalized assays for the genetic analysis of subjects or individual clinical cases. The types of assays which can be personalized in this way include, but are not limited to DNA sequencing, genotyping and gene expression. DNA sequencing may be selected from a group of methods consisting of (i) DNA sequencing by synthesis using a reversible terminator chemistry, or (ii) pyrosequencing, or (iii) nanopore sequencing, or (iv) real-time single molecule sequencing. Genotyping may comprise a single base extension. In this case, the multiplexed assay may be demultiplexed using a method selected from a group consisting of (i) hybridization to a DNA array using nucleic acid barcodes incorporated into the array-synthesized sequences, or (ii) PCR using primers incorporated into the array-synthesized sequences, or (iii) electrophoresis, or (iv) mass spectroscopy.

Combinations of Fixed and Variable (Personal) Genomic Content in the Array-Synthesized Nucleic Acids In an aspect of the present disclosure, some or all of the genomic content of the array-synthesized nucleic acids, may be based on the genetic characteristics originally determined for the individual subject. In some applications, it may be desirable for the oligo-directed genomic content of the personalized assay to contain both a variable portion (defined based on the genetic characteristics originally determined for the individual subject) and at least one fixed portion (which does not change from one subject to another). The fixed content may be synthesized on the same array as the variable content, or on a different array. The fixed content may participate in the personalized assay of all samples, or a subset of them.

If the variable content of multiple subjects is synthesized together on a single array, along with the shared fixed content, and if the variable portion is to be de-multiplexed following synthesis (e.g., using a barcode or priming segment of the sequence design) then the system for de-multiplexing may allow for the fixed content to also be captured with each of the separate sets of variable content. This can be done by assigning a separate barcode (or equivalent) to the fixed content, and conducting each post-synthesis de-multiplexing pullout reaction with both the barcode of the subject and the barcode of the fixed content.

Where the personalized assay is designed to use RNA (or cDNA derived from RNA), the fixed content may correspond to genes which are expected to be expressed at a lower level, and the variable content may correspond to genes which are expected to be expressed at a higher level.

Alternatively, the fixed content may correspond to genes with relatively stable expression (subject to subject) and the variable content may correspond to genes which are expressed more variably from subject to subject. In either case, the RNA targeted may include not only expressed RNA, but also non-coding RNA.

Where the personalized assay is designed for a cancer application, the variable content may correspond to potential neoantigen-causing variants of the subject. The fixed portion may be selected from a group consisting of one or more of (i) cancer driver genes, (ii) genes involved in the pharmacogenomics of cancer drugs, (iii) genes involved in Mendelian immunological diseases, (iv) genes related to inherited forms of cancer, (v) genes associated with tumor escape from a targeted or immune cancer therapy, (vi) HLA typing, or (vii) variants common in the population and used by B-allele methods to detect structural variation.

Where the personalized assay is designed for a Mendelian disease application, the variable content may correspond to variants which may be responsible for the Mendelian phenotype of a proband. The fixed portion may be selected from a group consisting of one or more of (i) additional genetic content not directly related to the Mendelian condition of the proband, or (ii) pharmacogenomics, or (iii) genetic sample ID by a fixed panel of variants or a fixed panel of phenotype-related variants such as gender, blood type, or (iv) variants common in the population and used by B-allele methods to detect structural variation.

Devices

The methods disclosed herein may comprise one or more devices. The methods disclosed herein may comprise one or more assays comprising one or more devices. The methods disclosed herein may comprise the use of one or more devices to perform one or more operations or assays. The methods disclosed herein may comprise the use of one or more devices in one or more operations or assays. For example, conducting a sequencing reaction may comprise one or more sequencers. In another example, producing a subset of nucleic acid molecules may comprise the use of one or more magnetic separators. In yet another example, one or more processors may be used in the analysis of one or more nucleic acid samples. Exemplary devices include, but are not limited to, sequencers, thermocyclers, real-time PCR instruments, magnetic separators, transmission devices, hybridization chambers, electrophoresis apparatus, centrifuges, microscopes, imagers, fluorometers, luminometers, plate readers, computers, processors, and bioanalyzers.

The methods disclosed herein may comprise one or more sequencers. The one or more sequencers may comprise one or more HiSeq, MiSeq, HiScan, Genome Analyzer IIx, SOLiD Sequencer, Ion Torrent PGM, 454 GS Junior, Pac Bio RS, or a combination thereof. The one or more sequencers may comprise one or more sequencing platforms. The one or more sequencing platforms may comprise GS FLX by 454 Life Technologies/Roche, Genome Analyzer by Solexa/Illumina, SOLiD by Applied Biosystems, CGA Platform by Complete Genomics, PacBio RS by Pacific Biosciences, or a combination thereof.

The methods disclosed herein may comprise one or more thermocyclers. The one or more thermocyclers may be used to amplify one or more nucleic acid molecules. The methods disclosed herein may comprise one or more real-time PCR instruments. The one or more real-time PCR instruments may comprise a thermal cycler and a fluorimeter. The one or more thermocyclers may be used to amplify and detect one or more nucleic acid molecules.

The methods disclosed herein may comprise one or more magnetic separators. The one or more magnetic separators may be used for separation of paramagnetic and ferromagnetic particles from a suspension. The one or more magnetic separators may comprise one or more LifeStep™ biomagnetic separators, SPHERO™ FlexiMag separator, SPHERO™ MicroMag separator, SPHERO™ HandiMag separator, SPHERO™ MiniTube Mag separator, SPHERO™ UltraMag separator, DynaMag™ magnet, DynaMag™-2 Magnet, or a combination thereof.

The methods disclosed herein may comprise one or more bioanalyzers. Generally, a bioanalyzer is a chip-based capillary electrophoresis machine that can analyze RNA, DNA, and proteins. The one or more bioanalyzers may comprise Agilent's 2100 Bioanalyzer.

The methods disclosed herein may comprise one or more processors. The one or more processors may analyze, compile, store, sort, combine, assess or otherwise process one or more data and/or results from one or more assays, one or more data and/or results based on or derived from one or more assays, one or more outputs from one or more assays, one or more outputs based on or derived from one or more assays, one or more outputs from one or data and/or results, one or more outputs based on or derived from one or more data and/or results, or a combination thereof. The one or more processors may transmit the one or more data, results, or outputs from one or more assays, one or more data, results, or outputs based on or derived from one or more assays, one or more outputs from one or more data or results, one or more outputs based on or derived from one or more data or results, or a combination thereof. The one or more processors may receive and/or store requests from a user. The one or more processors may produce or generate one or more data, results, outputs. The one or more processors may produce or generate one or more biomedical reports. The one or more processors may transmit one or more biomedical reports. The one or more processors may analyze, compile, store, sort, combine, assess or otherwise process information from one or more databases, one or more data or results, one or more outputs, or a combination thereof. The one or more processors may analyze, compile, store, sort, combine, assess or otherwise process information from 1, 2, 3, 4, 5, 6, 7, 8, 9, 10, 11, 12, 13, 14, 15, 16, 17, 18, 19, 20, 30 or more databases. The one or more processors may transmit one or more requests, data, results, outputs and/or information to one or more users, processors, computers, computer systems, memory locations, devices, databases, or a combination thereof. The one or more processors may receive one or more requests, data, results, outputs and/or information from one or more users, processors, computers, computer systems, memory locations, devices, databases or a combination thereof. The one or more processors may retrieve one or more requests, data, results, outputs and/or information from one or more users, processors, computers, computer systems, memory locations, devices, databases or a combination thereof.

The methods disclosed herein may comprise one or more memory locations. The one or more memory locations may store information, data, results, outputs, requests, or a combination thereof. The one or more memory locations may receive information, data, results, outputs, requests, or a combination thereof from one or more users, processors, computers, computer systems, devices, or a combination thereof.

Methods described herein can be implemented with the aid of one or more computers and/or computer systems. A computer or computer system may comprise electronic storage locations (e.g., databases, memory) with machine-executable code for implementing the methods provided herein, and one or more processors for executing the machine-executable code.

Figure 8:
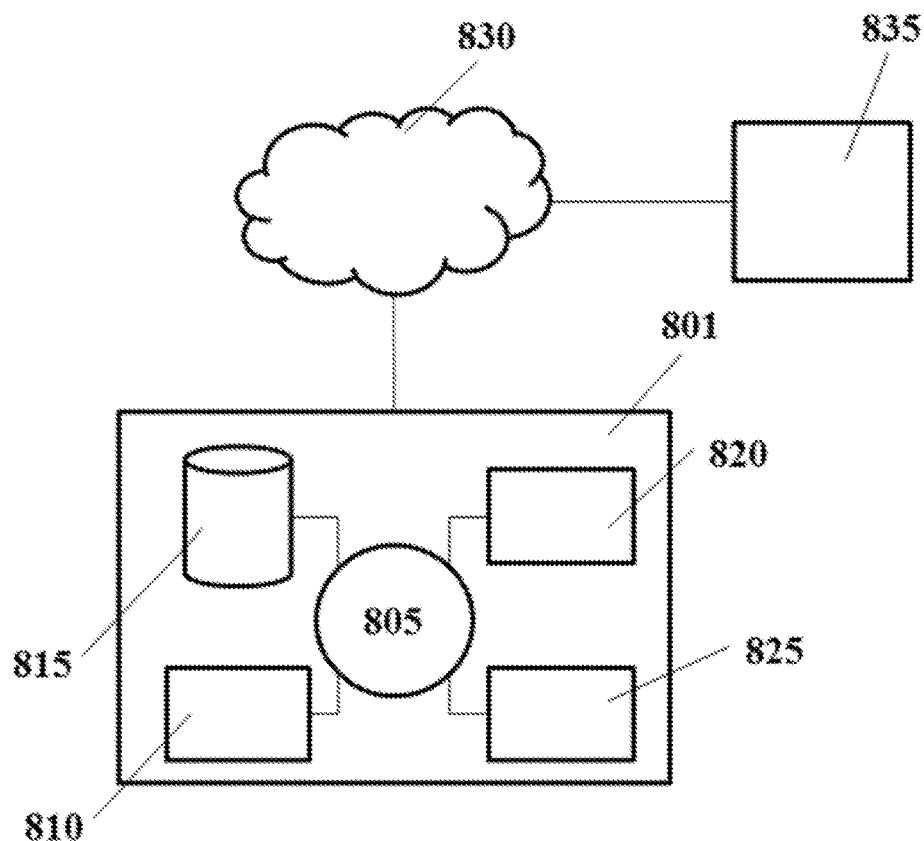
FIG. 8 shows a system for implementing the methods of the disclosure.

FIG. 8 shows a computer system (also "system" herein) 801 programmed or otherwise configured for implementing the methods of the disclosure, such as nucleic acid processing and/or analysis, and/or data analysis. The system 801 includes a central processing unit (CPU, also "processor" and "computer processor" herein) 805, which can be a single core or multi core processor, or a plurality of processors for parallel processing. The system 801 also includes memory 810 (e.g., random-access memory, read-only memory, flash memory), electronic storage unit 815 (e.g., hard disk), communications interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communications bus (solid lines), such as a motherboard. The storage unit 815 can be a data storage unit (or data repository) for storing data. The system 801 is operatively coupled to a computer network ("network") 830 with the aid of the communications interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830 in some cases, with the aid of the system 801, can implement a peer-to-peer network, which may enable devices coupled to the system 801 to behave as a client or a server.

The system 801 is in communication with a processing system 835. The processing system 835 can be configured to implement the methods disclosed herein. In some examples, the processing system 835 is a nucleic acid sequencing system, such as, for example, a next generation sequencing system (e.g., Illumina sequencer, Ion Torrent sequencer, Pacific Biosciences sequencer). The processing system 835 can be in communication with the system 801 through the network 830, or by direct (e.g., wired, wireless) connection. The processing system 835 can be configured for analysis, such as nucleic acid sequence analysis.

Methods as described herein can be implemented by way of machine (or computer processor) executable code (or software) stored on an electronic storage location of the system 801, such as, for example, on the memory 810 or electronic storage unit 815. During use, the code can be executed by the processor 805. In some examples, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The one or more computers and/or computer systems may analyze, compile, store, sort, combine, assess or otherwise process one or more data and/or results from one or more assays, one or more data and/or results based on or derived from one or more assays, one or more outputs from one or more assays, one or more outputs based on or derived from one or more assays, one or more outputs from one or data and/or results, one or more outputs based on or derived from one or more data and/or results, or a combination thereof. The one or more computers and/or computer systems may transmit the one or more data, results, or outputs from one or more assays, one or more data, results, or outputs based on or derived from one or more assays, one or more outputs from one or more data or results, one or more outputs based on or derived from one or more data or results, or a combination thereof. The one or more computers and/or computer systems may receive and/or store requests from a user. The one or more computers and/or computer systems may produce or generate one or more data, results, outputs. The one or more computers and/or computer systems may produce or generate one or more biomedical reports. The one or more computers and/or computer systems may transmit one or more biomedical reports. The one or more computers and/or computer systems may analyze, compile, store, sort, combine, assess or otherwise process information from one or more databases, one or more data or results, one or more outputs, or a combination thereof. The one or more computers and/or computer systems may analyze, compile, store, sort, combine, assess or otherwise process information from 1, 2, 3, 4, 5, 6, 7, 8, 9, 10, 11, 12, 13, 14, 15, 16, 17, 18, 19, 20, 30 or more databases. The one or more computers and/or computer systems may transmit one or more requests, data, results, outputs, and/or information to one or more users, processors, computers, computer systems, memory locations, devices, or a combination thereof. The one or more computers and/or computer systems may receive one or more requests, data, results, outputs, and/or information from one or more users, processors, computers, computer systems, memory locations, devices, or a combination thereof. The one or more computers and/or computer systems may retrieve one or more requests, data, results, outputs and/or information from one or more users, processors, computers, computer systems, memory locations, devices, databases or a combination thereof.

The methods disclosed herein may comprise one or more transmission devices comprising an output unit transmitting one or more data, results, outputs, information, biomedical outputs, and/or biomedical reports. The output unit can take any form which transmits the data, results, requests, and/or information and may comprise a monitor, printed format, printer, computer, processor, memory location, or a combination thereof. The transmission device may comprise one or more processors, computers, and/or computer systems for transmitting information.

The computer system 801 can include or be in communication with an electronic display 840 that comprises a user interface (UI) 845 for providing, for example, a report indicative of a presence or absence of at least a subset of genetic variants in a subject or at least one biological relative. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 805. The algorithm can, for example, be used to process sequencing data to determine a plurality of genetic characteristics, select probes for synthesis or from a collection of nucleic acid probe molecules.

Databases

The methods disclosed herein may comprise one or more databases. The methods disclosed herein may comprise at least about 1, 2, 3, 4, 5, 6, 7, 8, 9, 10, 11, 12, 13, 14, 15, 16, 17, 18, 19, 20, 30 or more databases. The databases may comprise genomic, proteomic, pharmacogenomic, biomedical, and scientific databases. The databases may be publicly available databases. Alternatively, or additionally, the databases may comprise proprietary databases. The databases may be commercially available databases. The databases include, but are not limited to, MendelDB, PharmGKB, Varimed, Regulome, curated BreakSeq junctions, Online Mendelian Inheritance in Man (OMIM), Human Genome Mutation Database (HGMD), NCBI dbSNP, NCBI RefSeq, GENCODE, GO (gene ontology), and Kyoto Encyclopedia of Genes and Genomes (KEGG).

The methods disclosed herein may comprise analyzing one or more databases. The methods disclosed herein may comprise analyzing at least about 1, 2, 3, 4, 5, 6, 7, 8, 9, 10, 11, 12, 13, 14, 15, 16, 17, 18, 19, 20, 30 or more databases. Analyzing the one or more databases may comprise one or more algorithms, computers, processors, memory locations, devices, or a combination thereof.

The methods disclosed herein may comprise producing one or more probes based on data and/or information from one or more databases. The methods disclosed herein may comprise producing one or more probe sets based on data and/or information from one or more databases. The methods disclosed herein may comprise producing one or more probes and/or probe sets based on data and/or information from at least about 2 or more databases. The methods disclosed herein may comprise producing one or more probes and/or probe sets based on data and/or information from at least about 3 or more databases. The methods disclosed herein may comprise producing one or more probes and/or probe sets based on data and/or information from at least about 4, 5, 6, 7, 8, 9, 10, 11, 12, 13, 14, 15, 16, 17, 18, 19, 20, 30 or more databases.

The methods disclosed herein may comprise identifying one or more nucleic acid regions based on data and/or information from one or more databases. The methods disclosed herein may comprise identifying one or more sets of nucleic acid regions based on data and/or information from one or more databases. The methods disclosed herein may comprise identifying one or more nucleic acid regions and/or sets of nucleic acid regions based on data and/or information from at least about 2 or more databases. The methods disclosed herein may comprise identifying one or more nucleic acid regions and/or sets of nucleic acid regions based on data and/or information from at least about 3 or more databases. The methods disclosed herein may comprise identifying one or more nucleic acid regions and/or sets of nucleic acid regions based on data and/or information from at least about 4, 5, 6, 7, 8, 9, 10, 11, 12, 13, 14, 15, 16, 17, 18, 19, 20, 30 or more databases. The methods disclosed herein may further comprise producing one or more probes and/or probe sets based on the identification of the one or more nucleic acid regions and/or sets of nucleic acid regions.

The methods disclosed herein may comprise analyzing one or more results based on data and/or information from one or more databases. The methods disclosed herein may comprise analyzing one or more sets of results based on data and/or information from one or more databases. The methods disclosed herein may comprise analyzing one or more combined results based on data and/or information from one or more databases. The methods disclosed herein may comprise analyzing one or more results, sets of results, and/or combined results based on data and/or information from at least about 2 or more databases. The methods disclosed herein may comprise analyzing one or more results, sets of results, and/or combined results based on data and/or information from at least about 3 or more databases. The methods disclosed herein may comprise analyzing one or more results, sets of results, and/or combined results based on data and/or information from at least about 4, 5, 6, 7, 8, 9, 10, 11, 12, 13, 14, 15, 16, 17, 18, 19, 20, 30 or more databases.

The methods disclosed herein may comprise comparing one or more results based on data and/or information from one or more databases. The methods disclosed herein may comprise comparing one or more sets of results based on data and/or information from one or more databases. The methods disclosed herein may comprise comparing one or more combined results based on data and/or information from one or more databases. The methods disclosed herein may comprise comparing one or more results, sets of results, and/or combined results based on data and/or information from at least about 2 or more databases. The methods disclosed herein may comprise comparing one or more results, sets of results, and/or combined results based on data and/or information from at least about 3 or more databases. The methods disclosed herein may comprise comparing one or more results, sets of results, and/or combined results based on data and/or information from at least about 4, 5, 6, 7, 8, 9, 10, 11, 12, 13, 14, 15, 16, 17, 18, 19, 20, 30 or more databases.

The methods disclosed herein may comprise biomedical databases, genomic databases, biomedical reports, disease reports, case-control analysis, and rare variant discovery analysis based on data and/or information from one or more databases, one or more assays, one or more data or results, one or more outputs based on or derived from one or more assays, one or more outputs based on or derived from one or more data or results, or a combination thereof.

Analysis

The methods disclosed herein may comprise one or more data, one or more data sets, one or more combined data, one or more combined data sets, one or more results, one or more sets of results, one or more combined results, or a combination thereof. The data and/or results may be based on or derived from one or more assays, one or more databases, or a combination thereof. The methods disclosed herein may comprise analysis of the one or more data, one or more data sets, one or more combined data, one or more combined data sets, one or more results, one or more sets of results, one or more combined results, or a combination thereof. The methods disclosed herein may comprise processing of the one or more data, one or more data sets, one or more combined data, one or more combined data sets, one or more results, one or more sets of results, one or more combined results, or a combination thereof.

The methods disclosed herein may comprise at least one analysis and at least one processing of the one or more data, one or more data sets, one or more combined data, one or more combined data sets, one or more results, one or more sets of results, one or more combined results, or a combination thereof. The methods disclosed herein may comprise one or more analyses and one or more processing of the one or more data, one or more data sets, one or more combined data, one or more combined data sets, one or more results, one or more sets of results, one or more combined results, or a combination thereof. The methods disclosed herein may comprise at least 1, 2, 3, 4, 5, 6, 7, 8, 9, 10, 15, 20, 30, 40, 50, 60, 70, 80, 90, 100, 200, 300, 400, 500, 600, 700, 800, 900, 1000 or more distinct analyses of the one or more data, one or more data sets, one or more combined data, one or more combined data sets, one or more results, one or more sets of results, one or more combined results, or a combination thereof. The methods disclosed herein may comprise at least 1, 2, 3, 4, 5, 6, 7, 8, 9, 10, 15, 20, 30, 40, 50, 60, 70, 80, 90, 100, 200, 300, 400, 500, 600, 700, 800, 900, 1000 or more distinct processing of the one or more data, one or more data sets, one or more combined data, one or more combined data sets, one or more results, one or more sets of results, one or more combined results, or a combination thereof. The one or more analyses and/or one or more processing may occur simultaneously, sequentially, or a combination thereof.

The one or more analyses and/or one or more processing may occur over 1, 2, 3, 4, 5, 6, 7, 8, 9, 10, 11, 12, 15, 20, 30, 40, 50, 60, 70, 80, 90, 100, 200, 300, 400, 500, 600, 700, 800, 900, 1000 or time points. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more hour period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more day period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more week period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more month period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more year period.

The methods disclosed herein may comprise one or more data. The one or more data may comprise one or more raw data based on or derived from one or more assays. The one or more data may comprise one or more raw data based on or derived from one or more databases. The one or more data may comprise at least partially analyzed data based on or derived from one or more raw data. The one or more data may comprise at least partially processed data based on or derived from one or more raw data. The one or more data may comprise fully analyzed data based on or derived from one or more raw data. The one or more data may comprise fully processed data based on or derived from one or more raw data. The data may comprise sequencing read data or expression data. The data may comprise biomedical, scientific, pharmacological, and/or genetic information.

The methods disclosed herein may comprise one or more combined data. The one or more combined data may comprise two or more data. The one or more combined data may comprise two or more data sets. The one or more combined data may comprise one or more raw data based on or derived from one or more assays. The one or more combined data may comprise one or more raw data based on or derived from one or more databases. The one or more combined data may comprise at least partially analyzed data based on or derived from one or more raw data. The one or more combined data may comprise at least partially processed data based on or derived from one or more raw data. The one or more combined data may comprise fully analyzed data based on or derived from one or more raw data. The one or more combined data may comprise fully processed data based on or derived from one or more raw data. One or more combined data may comprise sequencing read data or expression data. One or more combined data may comprise biomedical, scientific, pharmacological, and/or genetic information.

The methods disclosed herein may comprise one or more data sets. The one or more data sets may comprise one or more data. The one or more data sets may comprise one or more combined data. The one or more data sets may comprise one or more raw data based on or derived from one or more assays. The one or more data sets may comprise one or more raw data based on or derived from one or more databases. The one or more data sets may comprise at least partially analyzed data based on or derived from one or more raw data. The one or more data sets may comprise at least partially processed data based on or derived from one or more raw data. The one or more data sets may comprise fully analyzed data based on or derived from one or more raw data. The one or more data sets may comprise fully processed data based on or derived from one or more raw data. The data sets may comprise sequencing read data or expression data. The data sets may comprise biomedical, scientific, pharmacological, and/or genetic information.

The methods disclosed herein may comprise one or more combined data sets. The one or more combined data sets may comprise two or more data. The one or more combined data sets may comprise two or more combined data. The one or more combined data sets may comprise two or more data sets. The one or more combined data sets may comprise one or more raw data based on or derived from one or more assays. The one or more combined data sets may comprise one or more raw data based on or derived from one or more databases. The one or more combined data sets may comprise at least partially analyzed data based on or derived from one or more raw data. The one or more combined data sets may comprise at least partially processed data based on or derived from one or more raw data. The one or more combined data sets may comprise fully analyzed data based on or derived from one or more raw data. The one or more combined data sets may comprise fully processed data based on or derived from one or more raw data. The methods disclosed herein may further comprise further processing and/or analysis of the combined data sets. One or more combined data sets may comprise sequencing read data or expression data. One or more combined data sets may comprise biomedical, scientific, pharmacological, and/or genetic information.

The methods disclosed herein may comprise one or more results. The one or more results may comprise one or more data, data sets, combined data, and/or combined data sets. The one or more results may be based on or derived from one or more data, data sets, combined data, and/or combined data sets. The one or more results may be produced from one or more assays. The one or more results may be based on or derived from one or more assays. The one or more results may be based on or derived from one or more databases. The one or more results may comprise at least partially analyzed results based on or derived from one or more data, data sets, combined data, and/or combined data sets. The one or more results may comprise at least partially processed results based on or derived from one or more data, data sets, combined data, and/or combined data sets. The one or more results may comprise at fully analyzed results based on or derived from one or more data, data sets, combined data, and/or combined data sets. The one or more results may comprise fully processed results based on or derived from one or more data, data sets, combined data, and/or combined data sets. The results may comprise sequencing read data or expression data. The results may comprise biomedical, scientific, pharmacological, and/or genetic information.

The methods disclosed herein may comprise one or more sets of results. The one or more sets of results may comprise one or more data, data sets, combined data, and/or combined data sets. The one or more sets of results may be based on or derived from one or more data, data sets, combined data, and/or combined data sets. The one or more sets of results may be produced from one or more assays. The one or more sets of results may be based on or derived from one or more assays. The one or more sets of results may be based on or derived from one or more databases. The one or more sets of results may comprise at least partially analyzed sets of results based on or derived from one or more data, data sets, combined data, and/or combined data sets. The one or more sets of results may comprise at least partially processed sets of results based on or derived from one or more data, data sets, combined data, and/or combined data sets. The one or more sets of results may comprise at fully analyzed sets of results based on or derived from one or more data, data sets, combined data, and/or combined data sets. The one or more sets of results may comprise fully processed sets of results based on or derived from one or more data, data sets, combined data, and/or combined data sets. The sets of results may comprise sequencing read data or expression data. The sets of results may comprise biomedical, scientific, pharmacological, and/or genetic information.

The methods disclosed herein may comprise one or more combined results. The combined results may comprise one or more results, sets of results, and/or combined sets of results. The combined results may be based on or derived from one or more results, sets of results, and/or combined sets of results. The one or more combined results may comprise one or more data, data sets, combined data, and/or combined data sets. The one or more combined results may be based on or derived from one or more data, data sets, combined data, and/or combined data sets. The one or more combined results may be produced from one or more assays. The one or more combined results may be based on or derived from one or more assays. The one or more combined results may be based on or derived from one or more databases. The one or more combined results may comprise at least partially analyzed combined results based on or derived from one or more data, data sets, combined data, and/or combined data sets. The one or more combined results may comprise at least partially processed combined results based on or derived from one or more data, data sets, combined data, and/or combined data sets. The one or more combined results may comprise at fully analyzed combined results based on or derived from one or more data, data sets, combined data, and/or combined data sets. The one or more combined results may comprise fully processed combined results based on or derived from one or more data, data sets, combined data, and/or combined data sets. The combined results may comprise sequencing read data or expression data. The combined results may comprise biomedical, scientific, pharmacological, and/or genetic information.

The methods disclosed herein may comprise one or more combined sets of results. The combined sets of results may comprise one or more results, sets of results, and/or combined results. The combined sets of results may be based on or derived from one or more results, sets of results, and/or combined results. The one or more combined sets of results may comprise one or more data, data sets, combined data, and/or combined data sets. The one or more combined sets of results may be based on or derived from one or more data, data sets, combined data, and/or combined data sets. The one or more combined sets of results may be produced from one or more assays. The one or more combined sets of results may be based on or derived from one or more assays. The one or more combined sets of results may be based on or derived from one or more databases. The one or more combined sets of results may comprise at least partially analyzed combined sets of results based on or derived from one or more data, data sets, combined data, and/or combined data sets. The one or more combined sets of results may comprise at least partially processed combined sets of results based on or derived from one or more data, data sets, combined data, and/or combined data sets. The one or more combined sets of results may comprise at fully analyzed combined sets of results based on or derived from one or more data, data sets, combined data, and/or combined data sets. The one or more combined sets of results may comprise fully processed combined sets of results based on or derived from one or more data, data sets, combined data, and/or combined data sets. The combined sets of results may comprise sequencing read data or expression data. The combined sets of results may comprise biomedical, scientific, pharmacological, and/or genetic information.

The methods disclosed herein may comprise one or more outputs, sets of outputs, combined outputs, and/or combined sets of outputs. The methods, libraries, kits and systems herein may comprise producing one or more outputs, sets of outputs, combined outputs, and/or combined sets of outputs. The sets of outputs may comprise one or more outputs, one or more combined outputs, or a combination thereof. The combined outputs may comprise one or more outputs, one or more sets of outputs, one or more combined sets of outputs, or a combination thereof. The combined sets of outputs may comprise one or more outputs, one or more sets of outputs, one or more combined outputs, or a combination thereof. The one or more outputs, sets of outputs, combined outputs, and/or combined sets of outputs may be based on or derived from one or more data, one or more data sets, one or more combined data, one or more combined data sets, one or more results, one or more sets of results, one or more combined results, or a combination thereof. The one or more outputs, sets of outputs, combined outputs, and/or combined sets of outputs may be based on or derived from one or more databases. The one or more outputs, sets of outputs, combined outputs, and/or combined sets of outputs may comprise one or more biomedical reports, biomedical outputs, rare variant outputs, pharmacogenetic outputs, population study outputs, case-control outputs, biomedical databases, genomic databases, disease databases, net content.

The methods disclosed herein may comprise one or more biomedical outputs, one or more sets of biomedical outputs, one or more combined biomedical outputs, one or more combined sets of biomedical outputs. The methods, libraries, kits and systems herein may comprise producing one or more biomedical outputs, one or more sets of biomedical outputs, one or more combined biomedical outputs, one or more combined sets of biomedical outputs. The sets of biomedical outputs may comprise one or more biomedical outputs, one or more combined biomedical outputs, or a combination thereof. The combined biomedical outputs may comprise one or more biomedical outputs, one or more sets of biomedical outputs, one or more combined sets of biomedical outputs, or a combination thereof. The combined sets of biomedical outputs may comprise one or more biomedical outputs, one or more sets of biomedical outputs, one or more combined biomedical outputs, or a combination thereof. The one or more biomedical outputs, one or more sets of biomedical outputs, one or more combined biomedical outputs, one or more combined sets of biomedical outputs may be based on or derived from one or more data, one or more data sets, one or more combined data, one or more combined data sets, one or more results, one or more sets of results, one or more combined results, one or more outputs, one or more sets of outputs, one or more combined outputs, one or more sets of combined outputs, or a combination thereof. The one or more biomedical outputs may comprise biomedical biomedical information of a subject. The biomedical biomedical information of the subject may predict, diagnose, and/or prognose one or more biomedical features. The one or more biomedical features may comprise the status of a disease or condition, genetic risk of a disease or condition, reproductive risk, genetic risk to a fetus, risk of an adverse drug reaction, efficacy of a drug therapy, prediction of optimal drug dosage, transplant tolerance, or a combination thereof.

The methods disclosed herein may comprise one or more biomedical reports. The methods, libraries, kits and systems herein may comprise producing one or more biomedical reports. The one or more biomedical reports may be based on or derived from one or more data, one or more data sets, one or more combined data, one or more combined data sets, one or more results, one or more sets of results, one or more combined results, one or more outputs, one or more sets of outputs, one or more combined outputs, one or more sets of combined outputs, one or more biomedical outputs, one or more sets of biomedical outputs, combined biomedical outputs, one or more sets of biomedical outputs, or a combination thereof. The biomedical report may predict, diagnose, and/or prognose one or more biomedical features. The one or more biomedical features may comprise the status of a disease or condition, genetic risk of a disease or condition, reproductive risk, genetic risk to a fetus, risk of an adverse drug reaction, efficacy of a drug therapy, prediction of optimal drug dosage, transplant tolerance, or a combination thereof.

The methods disclosed herein may also comprise the transmission of one or more data, information, results, outputs, reports or a combination thereof. For example, data/information based on or derived from the one or more assays are transmitted to another device and/or instrument. In another example, the data, results, outputs, biomedical outputs, biomedical reports, or a combination thereof are transmitted to another device and/or instrument. The information obtained from an algorithm may also be transmitted to another device and/or instrument. Information based on the analysis of one or more databases may be transmitted to another device and/or instrument. Transmission of the data/information may comprise the transfer of data/information from a first source to a second source. The first and second sources may be in the same approximate location (e.g., within the same room, building, block, campus). Alternatively, first and second sources may be in multiple locations (e.g., multiple cities, states, countries, continents, etc). The data, results, outputs, biomedical outputs, biomedical reports can be transmitted to a patient and/or a healthcare provider.

Transmission may be based on the analysis of one or more data, results, information, databases, outputs, reports, or a combination thereof. For example, transmission of a second report is based on the analysis of a first report. Alternatively, transmission of a report is based on the analysis of one or more data or results. Transmission may be based on receiving one or more requests. For example, transmission of a report may be based on receiving a request from a user (e.g., patient, healthcare provider, individual).

Transmission of the data/information may comprise digital transmission or analog transmission. Digital transmission may comprise the physical transfer of data (a digital bit stream) over a point-to-point or point-to-multipoint communication channel. Examples of such channels are copper wires, optical fibres, wireless communication channels, and storage media. The data may be represented as an electromagnetic signal, such as an electrical voltage, radiowave, microwave, or infrared signal.

Analog transmission may comprise the transfer of a continuously varying analog signal. The messages can either be represented by a sequence of pulses using a line code (baseband transmission), or by a limited set of continuously varying wave forms (passband transmission), using a digital modulation method. The passband modulation and corresponding demodulation (also known as detection) can be carried out by modem equipment. According to the most common definition of digital signal, both baseband and passband signals representing bit-streams are considered as digital transmission, while an alternative definition only considers the baseband signal as digital, and passband transmission of digital data as a form of digital-to-analog conversion.

The methods disclosed herein may comprise one or more sample identifiers. The sample identifiers may comprise labels, barcodes, and other indicators which can be linked to one or more samples and/or subsets of nucleic acid molecules. The methods disclosed herein may comprise one or more processors, one or more memory locations, one or more computers, one or more monitors, one or more computer software, one or more algorithms for linking data, results, outputs, biomedical outputs, and/or biomedical reports to a sample.

The methods disclosed herein may comprise a processor for correlating the expression levels of one or more nucleic acid molecules with a prognosis of disease outcome. The methods disclosed herein may comprise one or more of a variety of correlative techniques, including lookup tables, algorithms, multivariate models, and linear or nonlinear combinations of expression models or algorithms. The expression levels may be converted to one or more likelihood scores, reflecting a likelihood that the patient providing the sample may exhibit a particular disease outcome. The models and/or algorithms can be provided in machine readable format and can, in some cases, further designate a treatment modality for a patient or class of patients.

Diseases or Conditions

The methods disclosed herein may comprise predicting, diagnosing, and/or prognosing a status or outcome of a disease or condition in a subject based on one or more biomedical outputs. Predicting, diagnosing, and/or prognosing a status or outcome of a disease in a subject may comprise diagnosing a disease or condition, identifying a disease or condition, determining the stage of a disease or condition, assessing the risk of a disease or condition, assessing the risk of disease recurrence, assessing reproductive risk, assessing genetic risk to a fetus, assessing the efficacy of a drug, assessing risk of an adverse drug reaction, predicting optimal drug dosage, predicting drug resistance, or a combination thereof.

The samples disclosed herein may be from a subject suffering from a cancer. The sample may comprise malignant tissue, benign tissue, or a mixture thereof. The cancer may be a recurrent and/or refractory cancer. Examples of cancers include, but are not limited to, sarcomas, carcinomas, lymphomas or leukemias.

Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g., alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. The cancer may be a skin cancer, such as a basal cell carcinoma, squamous, melanoma, nonmelanoma, or actinic (solar) keratosis.

The cancer may be a lung cancer. Lung cancer can start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendrogliomas. Nongliomas include meningiomas, pituitary adenomas, primary CNS lymphomas, and medulloblastomas. The cancer may be a meningioma.

The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic leukemia.

Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Additional diseases and/or conditions include, but are not limited to, atherosclerosis, inflammatory diseases, autoimmune diseases, rheumatic heart disease. Examples of inflammatory diseases include, but are not limited to, acne vulgaris, Alzheimer's, ankylosing spondylitis, arthritis (osteoarthritis, rheumatoid arthritis (RA), psoriatic arthritis), asthma, atherosclerosis, celiac disease, chronic prostatitis, Crohn's disease, colitis, dermatitis, diverticulitis, fibromyalgia, glomerulonephritis, hepatitis, irritable bowel syndrome (IBS), systemic lupus erythematous (SLE), nephritis, Parkinson's disease, pelvic inflammatory disease, sarcoidosis, ulcerative colitis, and vasculitis.

Examples of autoimmune diseases include, but are not limited to, acute disseminated encephalomyelitis (ADEM), Addison's disease, agammaglobulinemia, alopecia areata, amyotrophic Lateral Sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behçet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritisvepidermolysis bullosa acquisita, erythema nodosum, erythroblastosis fetalis, essential mixed cryoglobulinemia, Evan's syndrome, fibrodysplasia ossificans progressiva, fibrosing alveolitis (or idiopathic pulmonary fibrosis), gastritis, gastrointestinal pemphigoid, giant cell arteritis, glomerulonephritis, Goodpasture's syndrome, Graves' disease, Guillain-Barré syndrome (GBS), Hashimoto's encephalopathy, Hashimoto's thyroiditis, Henoch-Schonlein purpuravherpes gestationis aka gestational pemphigoid, hidradenitis suppurativa, Hughes-Stovin syndrome, hypogammaglobulinemia, idiopathic inflammatory demyelinating diseases, idiopathic pulmonary fibrosis, IgA nephropathy, inclusion body myositis, chronic inflammatory demyelinating polyneuropathyvinterstitial cystitis, juvenile idiopathic arthritis aka juvenile rheumatoid arthritis, Kawasaki's disease, Lambert-Eaton myasthenic syndrome, leukocytoclastic vasculitis, Lichen planus, Lichen sclerosus, linear IgA disease (LAD), Lou Gehrig's disease (Also Amyotrophic lateral sclerosis), lupoid hepatitis aka autoimmune hepatitis, lupus erythematosus, Majeed syndrome, Ménière's disease, microscopic polyangiitis, mixed connective tissue disease, morphea, Mucha-Habermann disease, multiple sclerosis, myasthenia gravis, myositis, neuromyelitis optica (also Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with *streptococcus*), paraneoplastic cerebellar degeneration, paroxysmal nocturnal hemoglobinuria (PNH), Parry Romberg syndrome, Parsonage-Turner syndrome, Pars planitis, pemphigus vulgaris, pernicious anaemia, perivenous encephalomyelitis, POEMS syndrome, polyarteritis nodosa, polymyalgia rheumatica, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, Schmidt syndrome another form of APS, Schnitzler syndrome, scleritis, scleroderma, serum sickness, Sjögren's syndrome, spondyloarthropathy, Stiff person syndrome, subacute bacterial endocarditis (SBE), Susac's syndrome, Sweet's syndrome, sympathetic ophthalmia, Takayasu's arteritis, temporal arteritis (also known as "giant cell arteritis"), thrombocytopenia, Tolosa-Hunt syndrome, transverse myelitis, ulcerative colitis, undifferentiated connective tissue disease different from mixed connective tissue disease, undifferentiated spondyloarthropathy, urticarial vasculitis, vasculitis, vitiligo, and Wegener's granulomatosis.

The methods provided herein may also be useful for detecting, monitoring, diagnosing and/or predicting a subject's response to an implanted device. Exemplary medical devices include but are not limited to stents, replacement heart valves, implanted cerebella stimulators, hip replacement joints, breast implants, and knee implants.

The methods disclosed herein may be used for monitoring the health of a fetus using whole or partial genome analysis of nucleic acids derived from a fetus, as compared to the maternal genome. For example, nucleic acids can be useful in pregnant subjects for fetal diagnostics, with fetal nucleic acids serving as a marker for gender, rhesus D status, fetal aneuploidy, and sex-linked disorders. The methods disclosed herein may identify fetal mutations or genetic abnormalities. The methods disclosed herein can enable detection of extra or missing chromosomes, particularly those typically associated with birth defects or miscarriage. The methods disclosed herein may comprise the diagnosis, prediction or monitoring of autosomal trisomies (e.g., Trisomy 13, 15, 16, 18, 21, or 22) may be based on the detection of foreign molecules. The trisomy may be associated with an increased chance of miscarriage (e.g., Trisomy 15, 16, or 22). Alternatively, the trisomy that is detected is a liveborn trisomy that may indicate that an infant will be born with birth defects (e.g., Trisomy 13 (Patau Syndrome), Trisomy 18 (Edwards Syndrome), and Trisomy 21 (Down Syndrome)). The abnormality may also be of a sex chromosome (e.g., XXY (Klinefelter's Syndrome), XYY (Jacobs Syndrome), or XXX (Trisomy X). The methods disclosed herein may comprise one or more genomic regions on the following chromosomes: 13, 18, 21, X, or Y. For example, the foreign molecule may be on chromosome 21 and/or on chromosome 18, and/or on chromosome 13. The one or more genomic regions may comprise multiple sites on multiple chromosomes.

Further fetal conditions that can be determined based on the methods and systems herein include monosomy of one or more chromosomes (X chromosome monosomy, also known as Turner's syndrome), trisomy of one or more chromosomes (13, 18, 21, and X), tetrasomy and pentasomy of one or more chromosomes (which in humans is most commonly observed in the sex chromosomes, e.g., XXXX, XXYY, XXXY, XYYY, XXXXX, XXXXY, XXXYY, XYYYY and XXYYY), monoploidy, triploidy (three of every chromosome, e.g., 69 chromosomes in humans), tetraploidy (four of every chromosome, e.g., 92 chromosomes in humans), pentaploidy and multiploidy.

The methods disclosed may comprise detecting, monitoring, quantitating, or evaluating one or more pathogen-derived nucleic acid molecules or one or more diseases or conditions caused by one or more pathogens. Exemplary pathogens include, but are not limited to, *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* or *Yersinia*. Additional pathogens include, but are not limited to, *Mycobacterium tuberculosis, Streptococcus, Pseudomonas, Shigella, Campylobacter,* and *Salmonella*.

The disease or conditions caused by one or more pathogens may comprise tuberculosis, pneumonia, foodborne illnesses, tetanus, typhoid fever, diphtheria, syphilis, leprosy, bacterial vaginosis, bacterial meningitis, bacterial pneumonia, a urinary tract infection, bacterial gastroenteritis, and bacterial skin infection. Examples of bacterial skin infections include, but are not limited to, impetigo which may be caused by *Staphylococcus aureus* or *Streptococcus pyogenes*; erysipelas which may be caused by a *streptococcus* bacterial infection of the deep epidermis with lymphatic spread; and cellulitis which may be caused by normal skin flora or by exogenous bacteria.

The pathogen may be a fungus, such as, *Candida, Aspergillus, Cryptococcus, Histoplasma, Pneumocystis,* and *Stachybotrys*. Examples of diseases or conditions caused by a fungus include, but are not limited to, jock itch, yeast infection, ringworm, and athlete's foot.

The pathogen may be a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis.

The pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g, *I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*).

Therapeutic Interventions

The methods disclosed herein may comprise providing a therapeutic intervention, such as, for example, treating and/or preventing a disease or condition in a subject based on one or more biomedical outputs. The one or more biomedical outputs may recommend one or more therapies. The one or more biomedical outputs may suggest, select, designate, recommend or otherwise determine a course of treatment and/or prevention of a disease or condition. The one or more biomedical outputs may recommend modifying or continuing one or more therapies. Modifying one or more therapies may comprise administering, initiating, reducing, increasing, and/or terminating one or more therapies. The one or more therapies comprise an anti-cancer, antiviral, antibacterial, antifungal, immunosuppressive therapy, or a combination thereof. The one or more therapies may treat, alleviate, or prevent one or more diseases or indications.

Examples of anti-cancer therapies include, but are not limited to, surgery, chemotherapy, radiation therapy, immunotherapy/biological therapy, photodynamic therapy. Anti-cancer therapies may comprise chemotherapeutics, monoclonal antibodies (e.g., rituximab, trastuzumab), cancer vaccines (e.g., therapeutic vaccines, prophylactic vaccines), gene therapy, or combination thereof.

The one or more therapies may comprise an antimicrobial. Generally, an antimicrobial refers to a substance that kills or inhibits the growth of microorganisms such as bacteria, fungi, virus, or protozoans. Antimicrobial drugs either kill microbes (microbicidal) or prevent the growth of microbes (microbiostatic). There are mainly two classes of antimicrobial drugs, those obtained from natural sources (e.g., antibiotics, protein synthesis inhibitors (such as aminoglycosides, macrolides, tetracyclines, chloramphenicol, polypeptides)) and synthetic agents (e.g., sulphonamides, cotrimoxazole, quinolones). In some instances, the antimicrobial drug is an antibiotic, anti-viral, anti-fungal, antimalarial, anti-tuberculosis drug, anti-leprotic, or anti-protozoal.

Antibiotics are generally used to treat bacterial infections. Antibiotics may be divided into two categories: bactericidal antibiotics and bacteriostatic antibiotics. Generally, bactericidals may kill bacteria directly where bacteriostatics may prevent them from dividing. Antibiotics may be derived from living organisms or may include synthetic antimicrobials, such as the sulfonamides. Antibiotics may include aminoglycosides, such as amikacin, gentamicin, kanamycin, neomycin, netilmicin, tobramycin, and paromomycin. Alternatively, antibiotics may be ansamycins (e.g., geldanamycin, herbimycin), cabacephems (e.g., loracarbef), carbapenems (e.g., ertapenem, doripenem, imipenem, cilastatin, meropenem), glycopeptides (e.g., teicoplanin, vancomycin, telavancin), lincosamides (e.g., clindamycin, lincomycin, daptomycin), macrolides (e.g., azithromycin, clarithromycin, dirithromycin, erythromycin, roxithromycin, troleandomycin, telithromycin, spectinomycin, spiramycin), nitrofurans (e.g., furazolidone, nitrofurantoin), and polypeptides (e.g., bacitracin, colistin, polymyxin B).

In some instances, the antibiotic therapy includes cephalosporins such as cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, and ceftobiprole.

The antibiotic therapy may also include penicillins. Examples of penicillins include amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, temocillin, and ticarcillin.

Alternatively, quinolines may be used to treat a bacterial infection. Examples of quinilones include ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin.

In some instances, the antibiotic therapy comprises a combination of two or more therapies. For example, amoxicillin and clavulanate, ampicillin and sulbactam, piperacillin and tazobactam, or ticarcillin and clavulanate may be used to treat a bacterial infection.

Sulfonamides may also be used to treat bacterial infections. Examples of sulfonamides include, but are not limited to, mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxazole (co-trimoxazole) (tmp-smx).

Tetracyclines are another example of antibiotics. Tetracyclines may inhibit the binding of aminoacyl-tRNA to the mRNA-ribosome complex by binding to the 30S ribosomal subunit in the mRNA translation complex. Tetracyclines include demeclocycline, doxycycline, minocycline, oxytetracycline, and tetracycline. Additional antibiotics that may be used to treat bacterial infections include arsphenamine, chloramphenicol, fosfomycin, fusidic acid, linezolid, metronidazole, mupirocin, platensimycin, quinupristin/dalfopristin, rifaximin, thiamphenicol, tigecycline, tinidazole, clofazimine, dapsone, capreomycin, cycloserine, ethambutol, ethionamide, isoniazid, pyrazinamide, rifampicin, rifamycin, rifabutin, rifapentine, and streptomycin.

Antiviral therapies are a class of medication used specifically for treating viral infections. Like antibiotics, specific antivirals are used for specific viruses. They are relatively harmless to the host, and therefore can be used to treat infections. Antiviral therapies may inhibit various stages of the viral life cycle. For example, an antiviral therapy may inhibit attachment of the virus to a cellular receptor. Such antiviral therapies may include agents that mimic the virus associated protein (VAP and bind to the cellular receptors. Other antiviral therapies may inhibit viral entry, viral uncoating (e.g., amantadine, rimantadine, pleconaril), viral synthesis, viral integration, viral transcription, or viral translation (e.g., fomivirsen). In some instances, the antiviral therapy is a morpholino antisense. Antiviral therapies should be distinguished from viricides, which actively deactivate virus particles outside the body.

Many of the antiviral drugs available are designed to treat infections by retroviruses, mostly HIV. Antiretroviral drugs may include the class of protease inhibitors, reverse transcriptase inhibitors, and integrase inhibitors. Drugs to treat HIV may include a protease inhibitor (e.g., invirase, saquinavir, kaletra, lopinavir, lexiva, fosamprenavir, norvir, ritonavir, prezista, duranavir, reyataz, viracept), integrase inhibitor (e.g., raltegravir), transcriptase inhibitor (e.g., abacavir, ziagen, agenerase, amprenavir, aptivus, tipranavir, crixivan, indinavir, fortovase, saquinavir, Intelence™, etravirine, isentress, viread), reverse transcriptase inhibitor (e.g., delavirdine, efavirenz, epivir, hivid, nevirapine, retrovir, AZT, stuvadine, truvada, videx), fusion inhibitor (e.g., fuzeon, enfuvirtide), chemokine coreceptor antagonist (e.g., selzentry, emtriva, emtricitabine, epzicom, or trizivir). Alternatively, antiretroviral therarapies may be combination therapies, such as atripla (e.g., efavirenz, emtricitabine, and tenofovira disoproxil fumarate) and completer (embricitabine, rilpivirine, and tenofovir disoproxil fumarate). Herpes viruses, known for causing cold sores and genital herpes, are usually treated with the nucleoside analogue acyclovir. Viral hepatitis (A-E) are caused by five unrelated hepatotropic viruses and are also commonly treated with antiviral drugs depending on the type of infection. Influenza A and B viruses are important targets for the development of new influenza treatments to overcome the resistance to existing neuraminidase inhibitors such as oseltamivir.

In some instances, the antiviral therapy may comprise a reverse transcriptase inhibitor. Reverse transcriptase inhibitors may be nucleoside reverse transcriptase inhibitors or non-nucleoside reverse transcriptase inhibitors. Nucleoside reverse transcriptase inhibitors may include, but are not limited to, combivir, emtriva, epivir, epzicom, hivid, retrovir, trizivir, truvada, videx ec, videx, viread, zerit, and ziagen. Non-nucleoside reverse transcriptase inhibitors may comprise edurant, intelence, rescriptor, sustiva, and viramune (immediate release or extended release).

Protease inhibitors are another example of antiviral drugs and may include, but are not limited to, agenerase, aptivus, crixivan, fortovase, invirase, kaletra, lexiva, norvir, prezista, reyataz, and viracept. Alternatively, the antiviral therapy may comprise a fusion inhibitor (e.g., enfuviride) or an entry inhibitor (e.g., maraviroc).

Additional examples of antiviral drugs include abacavir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, fusion inhibitors, ganciclovir, ibacitabine, imunovir, idoxuridine, imiquimod, indinavir, inosine, integrase inhibitor, interferons (e.g., interferon type I, II, III), lamivudine, lopinavir, loviride, maraviroc, moroxydine, methisazone, nelfinavir, nevirapine, nexavir, nucleoside analogues, oseltamivir, peginterferon alfa-2a, penciclovir, peramivir, pleconaril, podophyllotoxin, protease inhibitors, raltegravir, reverse transcriptase inhibitors, ribavirin, rimantadine, ritonavir, pyramidine, saquinavir, stavudine, tea tree oil, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

An antifungal drug is medication that may be used to treat fungal infections such as athlete's foot, ringworm, candidiasis (thrush), serious systemic infections such as cryptococcal meningitis, and others. Antifungals work by exploiting differences between mammalian and fungal cells to kill off the fungal organism. Unlike bacteria, both fungi and humans are eukaryotes. Thus, fungal and human cells are similar at the molecular level, making it more difficult to find a target for an antifungal drug to attack that does not also exist in the infected organism.

Antiparasitics are a class of medications which are indicated for the treatment of infection by parasites, such as nematodes, cestodes, trematodes, infectious protozoa, and amoebae. Like antifungals, they may kill the infecting pest without serious damage to the host.

Systems, Kits, and Libraries

Methods of the disclosure can be implemented by way of systems, kits, libraries, or a combination thereof. The methods of the present disclosure may comprise one or more systems. Systems of the disclosure can be implemented by way of kits, libraries, or both. A system may comprise one or more components to perform any of the methods or any of the operations of methods disclosed herein. For example, a system may comprise one or more kits, devices, libraries, or a combination thereof. A system may comprise one or more sequencers, processors, memory locations, computers, computer systems, or a combination thereof. A system may comprise a transmission device.

A kit may comprise various reagents for implementing various operations disclosed herein, including sample processing and/or analysis operations. A kit may comprise instructions for implementing at least some of the operations disclosed herein. A kit may comprise one or more capture probes, one or more beads, one or more labels, one or more linkers, one or more devices, one or more reagents, one or more buffers, one or more samples, one or more databases, or a combination thereof.

A library may comprise one or more capture probes. A library may comprise one or more subsets of nucleic acid molecules. A library may comprise one or more databases. A library may be produced or generated from any of the methods, kits, or systems disclosed herein. A database library may be produced from one or more databases. A method for producing one or more libraries may comprise (a) aggregating information from one or more databases to produce an aggregated data set; (b) analyzing the aggregated data set; and (c) producing one or more database libraries from the aggregated data set.

EXAMPLES

The following examples are provided for the purpose of illustrating various embodiments of the present disclosure and are not meant to limit the present disclosure. These examples, along with the methods described herein, are exemplary and are not intended to limit the scope of the present disclosure.

Example 1. Mendelian Disease Diagnosis

The following illustrates an example of Mendelian disease diagnosis utilizing the methods disclosed herein.

This example involves a family pedigree, in which at least one subject is affected by a medical condition which is suspected of being a rare Mendelian disease. In the first operation, DNA from one of the affected subjects of the pedigree is exome sequenced and the data is analyzed to identify variants relative to the human reference sequence. Several tens of thousands of such variants may be identified. This list is then filtered bioinformatically to identify which of those variants are non-synonymous (i.e., they may be expected to change the amino acid sequence of the protein expressed by this gene). This list is then further filtered bioinformatically to identify variants which have allele frequencies in the population below a cutoff, e.g., 1% (as may be expected for a variant causing a rare disease). This may narrow the list to less than five hundred variants. These are the genetic characteristics we focus on because they are most likely to contain the actual causal variant.

To identify which of these variants may be causal for the suspected Mendelian disease, one may need to know which of these variants exist in other members of the family pedigree, and with what zygosity. In general, the more family pedigree members included in this analysis, the better it is to narrow down the potential list. The list may also be narrowed by manual review of the list of variants, by genetic counselors or similar experts. They seek to rule out one variant at a time by using their judgment as to the phenotypic overlap between cases in the clinical literature and the clinical features of this particular case. This is a time consuming, expensive and somewhat subjective process. If genetic data can be obtained from more members of a family pedigree, the rules of genetic inheritance can be straightforwardly applied, and the list of potential variants may be narrowed less expensively and more definitively.

All of the other family members can be exome sequenced, as was done with the initial (affected) family member. That may involve a considerable amount of sequencing and quite expensive. A much less expensive method, as disclosed herein, is to create a pool of RNA molecules whose sequences are designed to capture the regions containing the 500 variants (e.g., using hybrid capture such as Agilent's Custom SureSelect). This may be done with one capture probe (an RNA molecule with a sequence complimentary to the genomic target) per variant. 500 variants may require the synthesis of at least about 500 sequences. The genomic region captured by each such probe may be at least about 350 bases. Therefore, for at least about 500 sequences, the footprint of this assay may be about 175,000 bases. Compared to an exome, where the footprint of the assay is typically at least 35 million bases, this may result in 200× less sequencing. This dramatic reduction in the amount of sequencing required, per additional family pedigree member, can make it much more affordable to sequence additional pedigree members (e.g., the parents, other children of the same parents, etc).

The saving in sequencing costs described above may be partially or even completely offset by the cost of synthesizing an array of hybrid capture probes. To address this, the capture probes for each of several independent clinical cases can be synthesized on a single array (the arrays used in Agilent's system for example, have a capacity up to about 55,000 probes/array). If twenty clinical cases are combined in a single array synthesis, at 500 probes each, the total may be 10,000 probes, still well within the capacity of the array. This amortizes the cost of array synthesis over the 20 cases. If the probes are not de-multiplexed post-synthesis, their footprints will be additive and thus be approximately 175,000 bases/case×20 cases=3.5 million bases. This is still at least a 10× reduction in sequencing footprint versus performing exome sequencing on each of the other family members of each of the pedigrees.

If the sequences of the capture probes are designed to include a barcode or primer pair, which is different for each clinical case, then it can be used post synthesis to separate out or enrich the capture probes for each clinical case. This can reduce the footprint of each personalized sequencing assay back to approximately 175,000 bases each.

Using the methods of the present disclosure, the cost of sequencing additional samples from a pedigree can be substantially reduced. This can be leveraged to sequence additional family members of the pedigree. It can also be used to sequence additional, potentially informative samples from the original affected family member or other family members.

Some Mendelian disease cases are caused by mosaic variants, i.e., mutations which occurred post-zygotically and which are thus only in a fraction of the cells of the subject. These variants can be in multiple tissues, or just in a single germ layer (i.e., ectoderm, endoderm, mesoderm). Because neural tissues, including the brain, are from the ectodermal germ layer, mosaic variants underlying neurological conditions may be in a larger fraction of ectodermal cells. These may include the cheek cells which may be captured by a buccal swab. In a published study of Cornelia-de-Lange syndrome patients for example, causal variants were found in buccal swabs of a substantial fraction of cases where they were not found in the blood of the same subject. Using method provided herein, the cost of sequencing incremental samples after the first one is relatively low, so it becomes more affordable to sequence both a blood sample and a buccal swab sample from an affected subject.

Moreover, some Mendelian cases, which appear to be due to de novo variants in a child, are actually the result of gonadal mosaicism in one of the parents being passed on to the child. Particularly in cases of advanced paternal age, the spermatogenic stem cells of the father will have undergone many stages of cell division. This can lead to mutations which are only in the sperm of the father, not his blood. These mutations can be passed on to a child who may then be afflicted by a Mendelian condition caused by the mutation. If testing only checks DNA from the blood of the parents and child, such a mutation may appear to be de novo in the child, making the parents feel safe to have a second child without fear that the second child inheriting the mutation. There are an unfortunately large number of cases where this has been proven incorrect and a second child inherits the same mutation from the sperm of the father as the first child did, and is similarly afflicted. Using method provided herein, the cost of sequencing incremental samples after the first one is relatively low, so it becomes more affordable to sequence DNA from both a blood sample and a sperm sample from the father of an affected subject.

Figure 2:
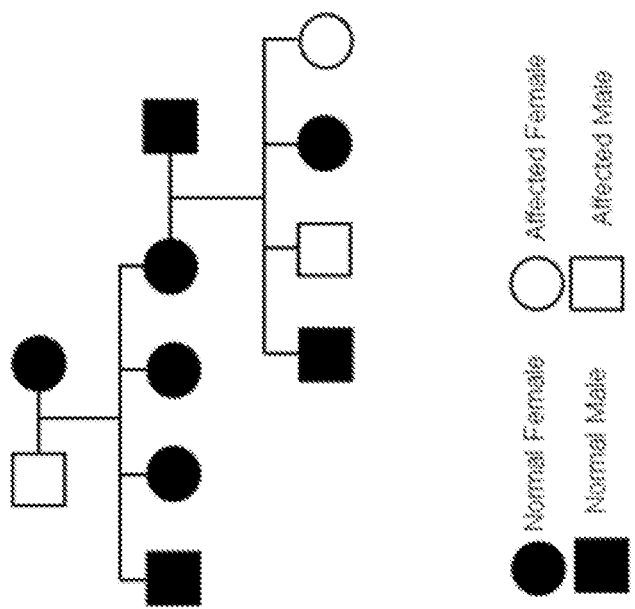
FIG. 2 shows an example of a Mendelian family pedigree.

FIG. 2 illustrates an example of a Mendelian family pedigree. In this pedigree, at least one subject may be affected by a medical condition which is suspected of being a rare Mendelian disease. Of the 11 member Mendelian pedigree, three members are determined to be affected. Mosaic variants may exist in just a small fraction of the cells of a sample taken from a subject. As a result, they can be more difficult to detect. A variant which is mosaic at low percentage in a parent can be inherited by their child, and if that happens, the variant will be in essentially every cell of the child. Thus, a variant which is straightforward to detect by normal sequencing levels in a child, may be more difficult to detect in their parent. This is important to determine because it informs the potential that a second child of the same parents can also inherit the variant and be similarly afflicted by it. Parents of afflicted children often seek genetic testing in part for this guidance. To increase the confidence of detecting a potentially mosaic variant in the parents, they will need to be sequenced at greater depth than the child. If the assay for additional members of a family pedigree is exome sequencing, it may be cost prohibitive to sequence at that depth. Using method provided herein, the footprint of the assay for incremental family members is much smaller (e.g., 175,000 bases vs 35 million bases, as discussed above). This smaller footprint makes it affordable to sequence the incremental samples at much greater depth, thus improving the sensitivity for detection of mosaic variants in the parents.

If the initial (afflicted) subject of a Mendelian pedigree is exome sequenced, the sensitivity to mosaic variants may be limited. An exome with average coverage of 80-100 fold, may have many regions with 20-fold coverage or less. If a mosaic variant is in just 10% of the cells of a sample (5% of the autosomal chromosome copies) then it may be seen in only a few raw sequence reads. To avoid false positive variant detection due to raw sequencing errors, variants are typically only called where they are seen in a number of reads which exceeds a threshold. The higher this threshold is, the lower the false positive rate, but also the lower the sensitivity to mosaic variants. Using methods described herein, the threshold for variant calls from the initial data may be set a lower, if the original sample (or another sample from the same subject) is to be among those sequenced later with the personalized assay. As has been described above, the smaller footprint of the personalized assay makes it much less expensive to sequence at high depths. This can be used to confirm the existence of mosaic variants in small percentages of cells, and to rule out false positives from the original data.

Example 2. Cancer Tumor Analysis, Including Neoantigen Detection

The following illustrates an example of cancer tumor analysis, utilizing the methods disclosed herein.

In this example, the subject is a cancer patient and the initial assay is next generation sequencing of DNA derived from their tumor, e.g., using an Illumina HiSeq-2500 instrument. To detect driver mutations (e.g., those involved in cell-cycle control), it may be sufficient to sequence a panel of genes, but to detect variants which may form neoantigens (and thus impact the response to checkpoint inhibitor drugs, or other immune-modulatory drugs, or combination therapies, personalized cancer vaccines, or CAR-T therapies), in some cases it may be preferable to sequence an exome. The sample can be based on surgical resection of all or part of the tumor or a small sample taken by biopsy procedures, for example. Raw sequence reads may be aligned to the human reference sequence and variants called relative to it. This list of variants can be filtered bioinformatically to select hose variants most likely to be relevant for the analysis of the tumor, or the patient's potential treatment. Alleles may also be reported at loci which determine HLA type.

Figure 6:
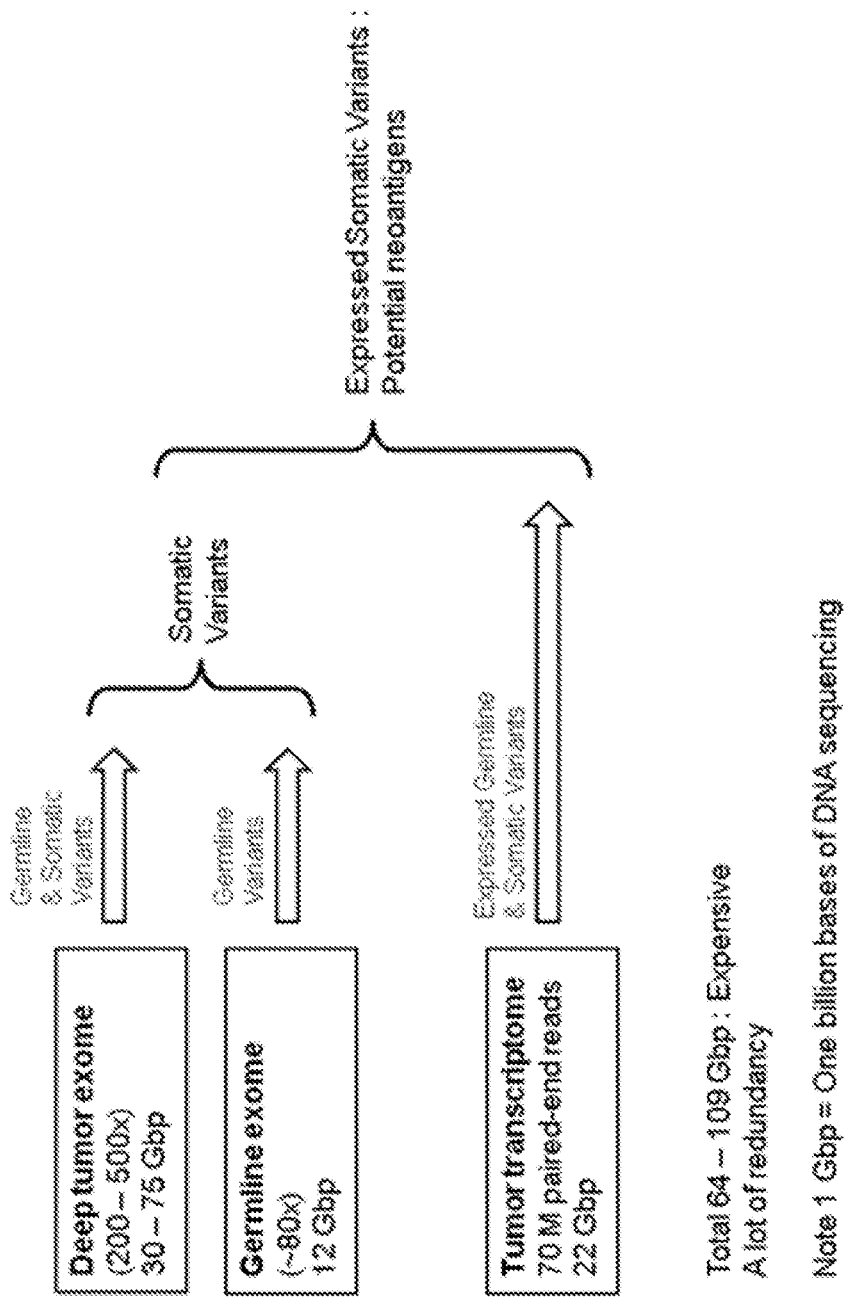
FIG. 6 shows a workflow for cancer sequencing, to detect variants potentially leading to neoantigens, with a summary of the relatively large amount of deoxynucleic acid (DNA) sequencing that may be required.

FIG. 6 illustrates a standard workflow for cancer sequencing. Variants may be detected potentially leading to neoantigens. Not all of the variants detected in a tumor are somatic, and not all are expressed in a tumor. In the standard cancer sequencing process, a deep tumor sample can be exome sequenced (e.g., 30-75 billion bases) and a germline DNA sample can be exome sequenced (e.g., 12 billion bases). The data can be used to determine which variants are somatic. Also, a tumor RNA (e.g., 22 billion bases, e.g., 50-70 million paired-end reads) can be deep transcriptome sequenced. A total of 64-109 billion bases of DNA sequencing for neoantigens may result in a significant cost.

Using methods of the present disclosure, the list of variants determined from sequencing the tumor DNA can be used to design a set of RNA sequences which can be used for hybrid capture of the regions containing the variants of this subject's tumor. These may be the basis of a personalized assay.

The personalized assay can then be used to sequence RNA (or cDNA derived from RNA) in the regions of this subject's tumor variants. A tumor RNA (e.g., 22 billion bases) can be deep transcriptome sequenced. This RNA data can be used to determine which of the variants, seen in the DNA, were expressed in RNA of the subject's tumor. As in the Mendelian example described above, the footprint of the personalized assay will be much smaller than an exome or transcriptome, substantially lowering the amount of sequencing which needs to be done.

The personalized assay can also be used to sequence a germline DNA sample from the subject. This data can be used to determine which variants, originally seen in the DNA or the tumor, are somatic.

The variants of a tumor may change in allele frequency over time, particularly if the tumor is poly-clonal. Observing this can provide information on the progression of the tumor. Frequent biopsies however, can be expensive and medically risky. An alternative is the look for the variants in nucleic acids shed by the tumor into the blood stream, by sequencing them from the blood plasma. Tumor nucleic acids in blood plasma can be at low concentrations, diluted by other sources of nucleic acids not related to the tumor (e.g., turnover of white blood cells). Thus a clonal tumor variant which is at 50% or 100% allele frequency in a sample of pure cancer cells, may be less than 1% in cell-free nucleic acids. Detecting variants at such low allele frequencies can require very deep sequencing (e.g., at least 1,000-fold coverage), which is very expensive, particularly if it is to be repeated at regular time intervals to monitor progression of a patient's tumor. This is particularly true with a generic assay that looks at all the loci where any variant can exist in any cancer patient. Using methods of the present disclosure, a personalized assay is created with a much smaller footprint. It can be applied to sequencing of cell-free nucleic acids of the patient at one or more time points. Because personalizing the assay has dramatically lowered the footprint of the assay relative to a generic one, the costs incurred are much lower and it becomes much more affordable to monitor a patient at multiple time points.

The approach described above provides a way to monitor the allele frequencies of known tumor variants of a subject over time, but it is unlikely to detect new variants that may be in a new sub-clone or metastasis. Many of these will be in cell-cycle control genes or genes which are the focus of targeted therapies. As an example, the drug erlotinib is frequently used for the treatment of late stage lung cancers in which the gene EGFR is mutated. Most of these patients eventually progress though, based on acquiring new mutations. About 50% of those involve acquisition of the T790M mutation in EGFR. A number of these genomic locations have been identified. To take advantage of this knowledge, the personal genomic content described above can be considered variable, and locations such as EGFR T790M can be considered fixed content. Thus, as discuss above, the genomic content of a personalized genetic assay may include a portion which is variable subject to subject, and another portion which is fixed.

Figure 7:
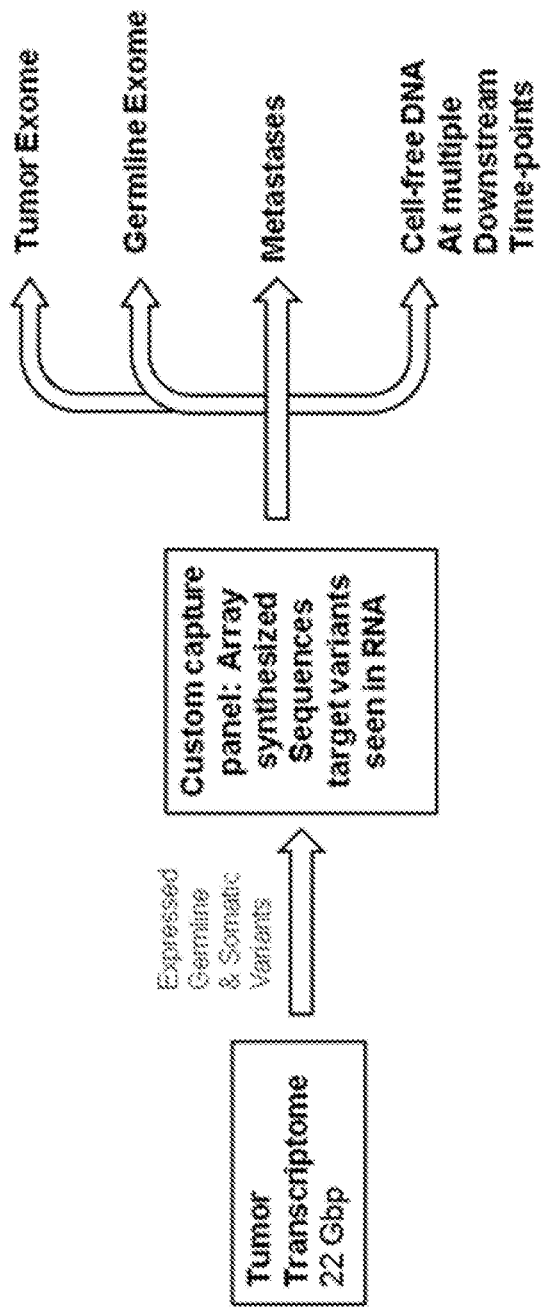
FIG. 7 shows an alternative workflow for cancer sequencing, to detect variants potentially leading to neoantigens, based on the methods of the present disclosure, with a significant reduction in the amount of DNA sequencing that may be required.

FIG. 7 shows an alternative workflow for cancer sequencing using an interactive array-based capture panel synthesis. The sequencing can detect variants potentially leading to neoantigens, with a significant reduction in the amount of DNA sequencing that may be required. The approach begins with DNA sequencing of just the tumor's DNA. Alternatively, a tumor RNA (e.g., 22 billion bases) can be deep transcriptome sequenced. Sequences may be array synthesized on a custom capture panel targeting variants seen in the RNA. In this approach, the tumor and germline exome may be sequenced later using a personalized assay based on variants detected in the tumor. In this case, the personalized assay may include variants which turn out to be germline. Metastases and cell-free DNA at multiple downstream time points may be monitored using the second assay. The custom capture panel, deep sequencing of additional samples and types becomes very inexpensive and can amortize costs over multiple samples.

Another alternative is to begin by sequencing both the tumor and germline DNA samples with a generic assay (e.g., an exome), to determine which variants are somatic. This may lead to a personalized assay with a smaller footprint. That approach may be advantageous when a personalized assay is to be used subsequently with many samples or when each involves sequencing very deeply to detect variants which are only in a small percent of cells in a sample.

In a cases in which variants potentially leading to neoantigens are to be used, it may be better to begin with a generic (i.e., not individualized) assay of tumor RNA (or cDNA derived from the RNA). Variants detected there will only be those which are expressed, thus excluding somatic variants which are not expressed. In at least one data set we have generated (from a Basal Cell Carcinoma) we found that only 20% of variants detected in the DNA were confirmed in the RNA of the same tumor. This does not mean that 80% of the variants detected in the DNA were false positives. It may mean that not all genes are expressed in a tumor, and even in the genes which are expressed, allelic expression and/or splice variation may prevent variants which exist in the DNA from being expressed in the RNA. After using a generic assay to find expressed variants in the RNA, the methods presently disclosed, along with that list of variants, can create a personalized assay. It can be used to look at the germline and tumor DNA, or cell free nucleic acids.

The examples above are based on initial assays which sequence DNA or RNA from the subject's tumor or a germline sample. Variants identified in that data are then used as the basis for designing nucleic acid sequences to be array synthesized to create a personalized assay. Methods of the present disclosure can also be used in a similar flow, but where the start is, or includes, an assay of cell-free DNA or RNA from the patient's blood plasma. Nucleic acids in blood plasma may include molecules derived from the tumor of a patient, but they will also contain molecules from the blood itself (e.g., the regular turnover of the white blood cell population).

In a subject's blood plasma, the ratio of RNA from a tumor to that from blood cells will vary by gene. Some genes, such as the globin genes, are highly expressed in blood cells, so they will create a high background signal in the population of cell-free RNA molecules in the plasma. Although these genes may also be expressed in a tumor, it may be at a lower level. The reverse can be true as well: tumors can express certain genes at a much higher level than blood cells do. This gene-specific tumor/background ratio will vary much less in cell free DNA in the plasma. Both DNA and RNA from a tumor can contain somatic variants, so either can be used to detect them. Given that the concentration ratio of tumor-derived nucleic acids will vary by gene differently for DNA vs RNA, overall sensitivity of tumor variant detection can be improved by assaying some genes in cell free DNA and other in cell free RNA. The choice of which genes to assay (e.g., sequence) in cfDNA vs cfRNA will vary by subject. It will depend on the cell type of the tumor, because different tumor cell types (e.g., lung vs breast) express different genes at different levels. It will also vary by tumor, since the genetic variation of one tumor may activate different pathways from those in another tumor, even if they are in the same type of cancer. It will also vary by the fraction of tumor nucleic acid that makes its way from the tumor to the blood plasma and the clearance rate of DNA vs RNA by the liver (this may also vary by molecule size and sequence). In addition to these factors, the genes expressed by blood cells of one subject, and their degree of expression, will be different from some other subjects. Using methods provided herein, the choice of which genes to assay in cfDNA vs cfRNA on an individual basis can be optimized. To do this, an initial generic assay may measure the expression of genes in the blood cells, thus quantifying by gene the primary background level that a cell-free RNA signal from the tumor will need to compete against. It may also measure the concentration of cell free DNA and/or RNA in the blood plasma by gene. It may also measure the RNA expression by gene in a tumor sample. Using this data, it may be determined an optimized partitioning of genes for subsequent detection in cell free DNA vs RNA. Nucleic acids can then be array synthesized to capture one or (separately) both of those in subsequent cell free assays.

Searching for Potential Neoantigens as Mosaic Variants in Non-cancer Cells:

Somatic variants which appear potentially antigenic, and hence candidates for use in a personalized cancer vaccine, may not be good candidates because they are actually mosaic variants also found elsewhere in the body and thus (a) the body may have become tolerated to them and (b) if the variants are elsewhere in the body and the vaccine is effective, it may lead to T-cell attack of those other parts of the body in addition to the cancer. Thus if these variants are also detected in additional samples of non-cancer cells, they may not be good vaccine candidates.

Given that there are about 1014 cells in an adult human body, almost every position in the human genome will be mosaic at some level in some cells in a human body. Quantifying that at the genomic loci to be specifically targeted by a personalized vaccine, can help assess whether the vaccine is appropriate.

Tumor variants with the highest allele frequencies frequently occurred prior to the initial "driver" mutation, and thus may well exist in other cells of the surrounding tissue. If this is just a few other cells, the impact may be unimportant, but if such a variant is in substantial non-cancer tissue, then it is a poor candidate to be the basis for a personalized cancer vaccine, for the reasons discussed above.

Adjacent normal tissue may be a good place to look for this possible mosaic variation, if it can be obtained uncontaminated by cancer cells. It may also be good to look in the apparent tissue of origin, in the case where the tumor DNA being sampled is from a metastasis, or is cell-free in the plasma (i.e., remote from its origin).

The present disclosure provides methods to inexpensively assay multiple tissue samples from a patient, for the variants seen in the tumor, even if they exist in a small fraction of cells in those tissue samples. Once the variants are identified in an initial assay, a personal assay can be created to look for other occurrences of those variants in other samples.

Example 3. RNA Analysis

The following illustrates an example of RNA analysis utilizing the methods disclosed herein.

Analysis of RNA from a cancer sample can be used to detect somatic variants and determine the levels at which they are expressed. The analysis can also be used to quantify the expression of genes, thus revealing the activation or suppression of specific cancer pathways. It can also be used to detect splicing variants and gene fusion events, which can both impact tumor progression.

Analysis of RNA is challenging due to its huge dynamic range. One gene can be expressed over 100,000-fold more than another. When next generation DNA sequencing is used to characterize expression, large numbers of sequence reads may be needed. In our laboratory, we offer RNA analysis commercially at a level of 50 million sequence read-pairs per sample, or 70 million. This is expensive, but needed to see the signal of genes expressed at a low level. It is also inefficient, as reads which come from the most highly expressed genes consume far more of the sequencing capacity than may be needed to obtain the desired measurement of those genes.

Using methods of the present disclosure, an initial low cost assessment of expression by gene from the sample of the tumor may be made. This does not need to be at a level deep enough to call variants, just enough to determine which genes may benefit from having their relative number of sequencing reads increased or decreased. This initial data can be used to design capture probe sets for genes which are in approximately the same gene expression range in the sample. Those one or more capture probe sets can then be the basis for a personalized RNA (or cDNA) sequencing assay.

The initial data from the subject's sample may be based on an analog method (e.g., fluorescent imaging of a hybridization array, or real-time quantitative PCR) or it may be based on a digital method (digital PCR, or next generation DNA sequencing). If it is based on next generation DNA sequencing, the RNA (or cDNA derived from it) may be selected by hybrid capture, or it may be selected by poly-A or ribo-minus methods, or any other suitable method. If it is based on next generation DNA sequencing, it may be sufficient at a level of five million reads, or even one million reads. The initial data may be of all genes in the human genome, or it may be of a subset of genes. The subset may be those genes known to have high expression in some samples, but much lower expression in other samples.

The personalized aspect of this assay (i.e., the component which varies from subject to subject) may include all of the genes, or it may include just a subset which needs additional coverage in addition to a fixed-content standard assay. (This concept of a personalized assay being comprised of a variable-genomic-content portion plus a fixed-genomic-content portion, was discussed above.) In this case, the initial assay may be designed to determine which genes will need "topping off" by the variable-genomic-content portion of the eventual personalized assay.

The exact algorithms to be used and sequences to be array-synthesized in the example above will be different for an RNA analysis whose primary goal is variant detection versus one whose primary goal is the measurement of gene expression levels. Where the goal is variant detection, the approach may attempt to achieve a minimum sequencing coverage level (e.g., 200×) over the full length of a targeted set of transcripts, at the lowest sequencing cost. Thus sequencing coverage above the target (e.g., 200×) may be avoided, in favor of lower overall costs, a more uniform distribution of reads, or both.

Example 4. Analysis of V(D)J Recombination

The following illustrates an example of V(D)J recombination analysis utilizing the methods disclosed herein.

V(D)J recombination is the mechanism by which the immune system can adapt to a wide range of antigens. Individual T-cells and B-cells of the immune system may contain individual V(D)J combinations. These sequences may lead to the creation of receptors on the outside surfaces of T-cells and B-cells which can very specifically bind to a particular antigen. V(D)J combinations are DNA sequences which can be measured individually, and a collection of these sequences are called a T-Cell repertoire (or correspondingly B-Cell repertoire). When the immune system is mounting a response to an antigen, such as an infection or a tumor, clonal amplification occurs, of the T/B-cells adapted to that antigen, leading to a higher number of copies of the corresponding V(D)J combination. Databases have been developed linking specific antigens (e.g., viruses, peptides, etc) and the V(D)J sequences of the primary T/B-cell response.

Sequencing both the T/B-cell repertoire and the DNA and RNA of a tumor, in an untargeted way, is expensive. Using methods of the present disclosure, one or the other can be sequenced first, a set of sequences can then be designed to create a personalized, targeted assay for the other.

Example 5. Combined Nucleic Acid and Protein/Peptide Analysis

The following illustrates an example of protein/peptide analysis, in some cases combined with nucleic acid analysis utilizing the methods disclosed herein.

This application uses oligo-antibody conjugates to act as transducers between the protein/peptide domains and nucleic acid domain. They are synthetic molecules which each combine an antibody physically linked to a nucleic acid sequence. If these molecules are exposed to a biological sample, their antibody segments can bind to target proteins in the sample. Conjugates which do not bind can then be washed off. As a next operation, the conjugates which did bind the sample can be eluted off and their nucleic acid segments can be sequenced. Quantifying these sequences is a measurement of the presence and quantity of the protein(s) or peptides targeted by the antibodies. This type of experiment can be conducted with a mixture of oligo-antibody conjugates, thus providing a multiplexed protein/peptide assay with nucleic acid sequencing readout.

Using method of the present disclosure, proteins and/or peptides can initially be quantified in a sample using a mixture of oligo-antibody conjugates. This information can then be used to design a set of nucleic acid sequences which are then array-synthesized. Those synthesized sequences can then be used in a personalized assay to target either (i) further measurement of proteins/peptides and/or (ii) measurement of genes (in DNA, RNA or cDNA derived from RNA) corresponding to the proteins detected by the original oligo-antibody assay.

Example 6. Determining Tissue of Origin, Based on Mosaic Variants

The following illustrates an example of determining tissue of origin utilizing the methods disclosed herein.

In the development of a subject from a single cell (the zygote, i.e., a fertilized human egg) there are many stages of cell division. Errors can occur in the DNA replication at each of these stages, leading to mosaic variants. Some of these variants will exist only in certain parts of the subject's body—those derived from the first cell in which the mutation occurred. Later in life, cells from one part of the body may move elsewhere in the body. Tumor metastasis is one such example. It can be useful in determining the optimal medical treatment for a patient, to know the tissue of origin of a sample (e.g., one taken from a metastatic tumor, particularly in cases where the primary tumor has not been identified and may no longer even exist).

U.S. Patent Publication No. 2016/0122831 discloses methods for identifying a tissue of origin of a biological sample. Those methods are based on construction of a mutational map, which links mosaic variants to the tissues in which they are seen. The present disclosure provides efficient methods for identifying a tissue of origin of a biological sample. This method begins by sequencing nucleic acids from a sample of the subject, thought to be located distal to its origin (e.g., a metastatic tumor). From that sequence data we identify post-zygotic mutations (i.e., mosaic or somatic mutations not present in the subject's germline). The genomic locations of the identified post-zygotic mutations become the basis for designing a set of nucleic acid sequences, to be array-synthesized and used in a personalized assay. That personalized assay captures genomic regions of one or more of the loci and sequences or genotypes them. This provides an inexpensive method to determine whether those post-zygotic genetic variants exist in specific other tissues of the subject's body and to quantify them. By knowing where in the subject's body each variant is seen and not seen, evidence is gained narrowing the potential tissue of origin of the original sample.

The original sample for this method may be obtained directly from a tumor (e.g., by a biopsy) or indirectly. If indirectly, it may be from cell-free nucleic acids in blood plasma, RNA from exosomes, or nucleic acids from circulating tumor cells. The original sample may also be from what is thought to be a primary tumor, tested to confirm whether it is actually from the tissue within which it has been found.

Example 7: Synthesis of a Plurality of Probe Molecules Using an Array

The following illustrates an example synthesizing a plurality of probe molecules on an array utilizing the methods disclosed herein.

From a biological sample of a subject, genetic characteristics, e.g., genetic variants, will be identified in the nucleic acid molecules of the sample. Probe sequences will be selected using the methods described herein.

A plurality of nucleic acid probe molecules will be synthesized for further personalized genetic testing. Probe molecules will be synthesized by "printing" or spotting probes onto a microarray surface (e.g., glass). Probe spots will be applied by either contact or non-contact printing. A noncontact printer will use the same technology as computer printers (i.e., bubble jet or inkjet) to expel small droplets of probe solution onto the glass slide. In contact printing, each print pin will directly apply the probe solution onto the microarray surface. The result in both cases is the application of a few nanoliters of probe solution per spot to create an array of 100- to 150-μm features. Multiple droplets of a biopolymer or biomonomer fluid comprising nucleic acid(s) are dispensed from a jet to form an array of droplets on a substrate. Repeated rounds of base-by-base printing will extend the length of specific probes. The final product can be more than 50-mer (e.g. 60 mer) in situ synthesis feature on a microarray containing thousands of specifically synthesized probes.

An assay will be performed using the synthesized array to analyze a biological sample from the individual from whom the sample was collected or biological relative(s) of the subject. The assay will generate data indicative of a presence or absence of at least a subset of genetic variants in a subject or the subject's biological relatives.

Methods of the present disclosure may be combined with methods described in U.S. Pat. Nos. 9,128,861 and 9,183, 496, U.S. Patent Publication No. 2016/0122831, and PCT Patent Publication No. WO/2015/051275, each of which is entirely incorporated herein by reference.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for personalized genetic testing, comprising:
   (a) sequencing nucleic acid molecules from at least one biological sample of a subject to generate sequencing data, wherein said sequencing comprises sequencing 12 gigabases (GB) or more;
   (b) computer processing said sequencing data to identify a plurality of nucleic acid sequences having a set of genetic variants, wherein said set of genetic variants are identified with respect to a reference;
   (c) obtaining a probe set comprising a plurality of nucleic acid probe molecules having said plurality of nucleic acid sequences or complements thereof, wherein said plurality of nucleic acid probe molecules are configured to selectively enrich or amplify sequences comprising said set of genetic variants over other sequences in said at least one biological sample;
   (d) using said probe set to selectively enrich or amplify sequences comprising said set of genetic variants over other sequences in an additional biological sample from said subject or at least one biological relative of said subject, to generate a sequencing library; and
   (e) subjecting said sequencing library to sequencing at a coverage of 175 kilobases (kb) or less to identify a presence or absence of at least a subset of said set of genetic variants in said additional biological sample from said subject or said at least one biological relative, wherein a sequencing depth of said sequencing of (e) is greater than a sequencing depth of said sequencing of (a).

2. The method of claim 1, further comprising outputting a report that is generated at least based on comparison of results from said sequencing of (a) with results from at least said subjecting said sequencing library to said sequencing of (e).

3. The method of claim 1, wherein in said sequencing of (a), said at least one biological sample is obtained from said subject at a first time point, and wherein said additional biological sample is obtained from said subject or said at least one biological relative at a second time point subsequent to said first time point.

4. The method of claim 1, wherein said sequencing of (a) comprises (i) exome sequencing, (ii) sequencing a panel of genes, (iii) whole genome sequencing, and/or (iv) sequencing a population of complementary deoxyribonucleic acid molecules derived from ribonucleic acid molecules.

5. The method of claim 1, wherein each of said plurality of nucleic acid probe molecules includes oligonucleotide-directed genomic content comprising (i) at least one variable portion from a result of said sequencing of (a) and (ii) at least one fixed portion independent of said result of said sequencing of (a).

6. The method of claim 5, wherein said at least one variable portion corresponds to genes which are more highly expressed than genes that correspond to said at least one fixed portion.

7. The method of claim 5, wherein said at least one variable portion corresponds to genes with a first expression profile and said at least one fixed portion corresponds to genes with a second expression profile, wherein said first expression profile has greater sample-to-sample variability than said second expression profile.

8. The method of claim 1, wherein (c) comprises synthesizing said plurality of nucleic acid probe molecules using at least one array.

9. The method of claim 1, further comprising outputting a report that identifies said presence or absence of said at least said subset of said genetic variants in said subject or said at least one biological relative.

10. The method of claim 1, further comprising providing a therapeutic intervention at least based on said presence or absence of said at least said subset of said genetic variants identified in (e).

11. The method of claim 1, wherein said at least one biological sample includes a tumor sample and said nucleic acids molecules are from cells in said tumor sample.

12. The method of claim 1, wherein said plurality of nucleic acid sequences having said set of genetic variants comprises one or more members selected from the group consisting of: (i) single nucleotide polymorphisms, (ii) insertions or deletions, (iii) copy number variations, and (iv) structural variations.

13. The method of claim 1, wherein said plurality of nucleic acid sequences having said set of genetic variants comprises genetic variants in a germline sequence of said subject.

14. The method of claim 1, wherein said plurality of nucleic acid sequences having said set of genetic variants comprises post-zygotic variants from a germline sequence of said subject or recombination of elements from a germline sequence of said subject.

15. The method of claim 1, further comprising, in (b), computer processing said sequencing data to identify a plurality of genetic characteristics of said subject comprising levels of gene expression, sequence counts, or read-depth in said sequencing data generated from ribonucleic acid molecules or complementary deoxyribonucleic acid molecules derived from said at least one biological sample.

16. The method of claim 1, wherein said computer processing of said sequencing data comprises identifying levels of methylation at locations or in specific regions of a genome.

17. The method of claim 1, wherein said plurality of nucleic acid sequences having said set of genetic variants comprise locations in or regions of a genome, and wherein in (d) said probe set enriches or depletes a nucleic acid mixture of nucleic acid molecules from said additional biological sample, which nucleic acid molecules include said locations or regions of said genome or portions thereof.

18. The method of claim 1, wherein subjecting said sequencing library to sequencing in (e) comprises generating nucleic acid sequence data from said additional biological sample.

19. The method of claim 1, wherein computer processing of said sequence data comprises identifying one or more of (i) genetic variants of said nucleic acid sequence with respect to a germline sequence(s), (ii) alleles which match said reference sequence(s) and are correlated with a type of cancer or other disease, (iii) alleles which determine a human leukocyte antigen (HLA) type, (iv) metrics of gene expression or allele-specific expression, and (v) quantification of non-coding ribonucleic acid (RNA) molecules or micro-RNA molecules which are at least partially tissue-type specific or cancer-type specific.

20. The method of claim 1, wherein said at least one biological sample of (a) and said additional biological sample of (d) include the same biological sample.

21. The method of claim 1, wherein in (a), said nucleic acid molecules from said at least one biological sample of said subject are obtained distal to their origin in a body of said subject, and said plurality of nucleic acid sequences having said set of genetic variants includes identified genomic locations of mosaic variants in said at least one biological sample.

22. The method of claim 21, wherein in (e), said subjecting said sequencing library to sequencing is performed on said additional biological sample from one or more other locations in said body of said subject, to determine an extent to which said mosaic variants are observed in said one or more biological samples.

23. The method of claim 1, wherein said probe set is obtained using only said plurality of nucleic acid sequences having a set of genetic variants.

24. The method of claim 1, wherein said additional biological sample is from said at least one biological relative of said subject, and wherein said subjecting said sequencing library to sequencing in (e) generates data indicative of a presence or absence of at least said subset of said set of said genetic variants in said additional biological sample from said at least one biological relative.

25. The method of claim 1, wherein said probe set is obtained using only said plurality of nucleic acid sequences having said set of genetic variants, wherein said additional biological sample is from said at least one biological relative of said subject, and wherein said subjecting said sequencing library to sequencing in (e) generates data indicative of a presence or absence of at least a subset of said set of genetic variants in said additional biological samples from said at least one biological relative.

26. The method of claim 1, wherein said subject is affected by a Mendelian disease, and wherein in (e) said at least one biological relative of said subject is assayed using said probe set from (c), to generate data indicative of said presence or absence of at least said subset of said set of genetic variants in said additional biological sample from said at least one biological relative.

27. The method of claim 1, further comprising prior to (c), filtering said plurality of nucleic acid sequences having a set of genetic variants by one or more factors selected from the group consisting of: non-synonymous variants, minor allele frequency population of at most about 1%, phenotype match, and inheritance.

28. The method of claim 1, further comprising using said presence or absence of said at least said subset of said set of genetic variants identified in (e) to treat said subject or said at least one biological relative for a disorder.

29. The method of claim 1, wherein said reference comprises a human reference sequence.

30. The method of claim 1, wherein said reference is a human reference sequence.

31. The method of claim 1, wherein said sequencing library is generated from a plurality of biological samples comprising said additional biological sample, and wherein (e) comprises sequencing said sequencing library to generate sequencing reads that are compared to generate a report.

* * * * *